United States Patent
Shelton et al.

(10) Patent No.: US 11,814,417 B2
(45) Date of Patent: *Nov. 14, 2023

(54) GIP AGONIST COMPOUNDS AND METHODS

(71) Applicant: Zealand Pharma A/S, Søborg (DK)

(72) Inventors: Anne Pernille Tofteng Shelton, Søborg (DK); Pia Nørregaard, Søborg (DK); Maria Alexandrovna Deryabina, Søborg (DK); Bjarne Due Larsen, Søborg (DK); Jacob Ulrik Fog, Søborg (DK)

(73) Assignee: Zealand Pharma A/S, Søborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/221,287

(22) Filed: Apr. 2, 2021

(65) Prior Publication Data

US 2022/0041676 A1    Feb. 10, 2022

Related U.S. Application Data

(63) Continuation of application No. 16/281,347, filed on Feb. 21, 2019, now Pat. No. 11,001,619, which is a continuation of application No. 15/521,631, filed as application No. PCT/EP2015/075120 on Oct. 29, 2015, now Pat. No. 10,253,078.

(30) Foreign Application Priority Data

Oct. 29, 2014 (DK) .................. 2014 00629
Jul. 20, 2015 (DK) .................. 2015 00381

(51) Int. Cl.
| | | |
|---|---|---|
| A61K 38/00 | (2006.01) | |
| C07K 14/575 | (2006.01) | |
| A61K 38/22 | (2006.01) | |
| A61K 45/06 | (2006.01) | |

(52) U.S. Cl.
CPC ............ C07K 14/575 (2013.01); A61K 38/22 (2013.01); A61K 45/06 (2013.01); *A61K 38/00* (2013.01)

(58) Field of Classification Search
None
See application file for complete search history.

(56) References Cited

U.S. PATENT DOCUMENTS

| | | |
|---|---|---|
| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,795,861 A | 8/1998 | Kolterman et al. |
| 5,846,747 A | 12/1998 | Thorens et al. |
| 5,846,937 A | 12/1998 | Drucker |
| 6,006,753 A | 12/1999 | Efendic |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |
| 6,458,924 B2 | 10/2002 | Knudsen et al. |
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,056,734 B1 | 6/2006 | Egan et al. |
| 7,115,569 B2 | 10/2006 | Beeley et al. |
| 7,138,375 B2 | 11/2006 | Beeley et al. |
| 7,153,825 B2 | 12/2006 | Young et al. |
| 7,157,555 B1 | 1/2007 | Beeley et al. |

(Continued)

FOREIGN PATENT DOCUMENTS

| | | |
|---|---|---|
| AU | 3247799 A | 9/1999 |
| AU | 2008326324 A1 | 5/2009 |

(Continued)

OTHER PUBLICATIONS

U.S. Appl. No. 14/116,268, Just et al.
U.S. Appl. No. 14/516,216, filed Apr. 23, 2015, Riber et al.
U.S. Appl. No. 14/517,497, filed Apr. 23, 2015, Riber et al.
U.S. Appl. No. 14/843,047, filed May 5, 2016, Zealand Pharma A/S.
U.S. Appl. No. 60/132,018, Prickett et al.
U.S. Appl. No. 61/784,294, Tolborg et al.
Abbrecht et al., "Erythrocyte life-span in mice acclimatized to different degrees of hypoxia," J Appl Physiol. 32(4):443-445 (1972).
Action Closing Prosecution in Inter Partes Reexam 95/000,276, mailed Mar. 17, 2011 (25 pages).

(Continued)

*Primary Examiner* — Thomas S Heard
(74) *Attorney, Agent, or Firm* — Clark & Elbing LLP

(57) ABSTRACT

The present invention relates to acylated GIP analogues which have GIP agonist activity, and their use in the treatment of metabolic disorders.

21 Claims, 9 Drawing Sheets
Specification includes a Sequence Listing.

(56) References Cited

U.S. PATENT DOCUMENTS

| | | |
|---|---|---|
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,803,766 B2 | 9/2010 | Cruz |
| 7,858,740 B2 | 12/2010 | Beeley et al. |
| 7,928,065 B2 | 4/2011 | Young et al. |
| 7,935,786 B2 | 5/2011 | Larsen |
| 7,994,122 B2 | 8/2011 | Riber et al. |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,540 B2 | 2/2014 | Meier et al. |
| 8,642,541 B2 | 2/2014 | Meier et al. |
| 8,642,727 B2 | 2/2014 | Larsen et al. |
| 8,680,049 B2 | 3/2014 | Meier et al. |
| 8,685,919 B2 | 4/2014 | Meier et al. |
| RE45,313 E | 12/2014 | Larsen et al. |
| 9,089,538 B2 | 7/2015 | Neerup et al. |
| 9,156,901 B2 | 10/2015 | Riber et al. |
| 9,169,310 B2 | 10/2015 | Riber et al. |
| 9,180,169 B2 | 11/2015 | Tolborg et al. |
| 9,259,477 B2 | 2/2016 | Tolborg et al. |
| 9,403,894 B2 | 8/2016 | Meier et al. |
| 9,453,064 B2 | 9/2016 | Just et al. |
| 9,649,362 B2 | 5/2017 | Neerup et al. |
| 9,750,788 B2 | 9/2017 | Kadereit et al. |
| 9,790,262 B2 | 10/2017 | Shandler et al. |
| 9,896,495 B2 | 2/2018 | Riber et al. |
| 9,969,787 B2 | 5/2018 | Just et al. |
| 9,975,939 B2 | 5/2018 | Tolborg et al. |
| 9,988,429 B2 | 6/2018 | Riber et al. |
| 10,004,786 B2 | 6/2018 | Riber et al. |
| 10,093,713 B2 | 10/2018 | Shelton et al. |
| 10,100,097 B2 | 10/2018 | Just et al. |
| 10,131,702 B2 | 11/2018 | Just et al. |
| 10,253,078 B2 | 4/2019 | Shelton et al. |
| 11,001,619 B2 | 5/2021 | Shelton et al. |
| 2002/0137666 A1 | 9/2002 | Beeley et al. |
| 2004/0106547 A1 | 6/2004 | Larsen et al. |
| 2005/0070469 A1 | 3/2005 | Bloom et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2009/0088369 A1 | 4/2009 | Steiness |
| 2010/0099601 A1 | 4/2010 | Weiss |
| 2010/0190701 A1 | 7/2010 | Day et al. |
| 2010/0240883 A1 | 9/2010 | Wu et al. |
| 2011/0144008 A1 | 6/2011 | Larsen et al. |
| 2011/0230397 A1 | 9/2011 | Camera et al. |
| 2011/0245165 A1 | 10/2011 | Larsen et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2011/0312878 A1 | 12/2011 | Larsen |
| 2012/0178670 A1 | 7/2012 | Riber et al. |
| 2013/0053304 A1 | 2/2013 | Wang et al. |
| 2013/0143793 A1 | 6/2013 | Neerup et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0210722 A1 | 8/2013 | Larsen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2014/0187483 A1 | 7/2014 | Steiness |
| 2014/0336107 A1 | 11/2014 | Tolborg et al. |
| 2014/0336356 A1 | 11/2014 | Larsen et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0210744 A1 | 7/2015 | Riber et al. |
| 2015/0299281 A1 | 10/2015 | Just et al. |
| 2015/0322130 A1 | 11/2015 | Dimarchi et al. |
| 2015/0376257 A1 | 12/2015 | Riber et al. |
| 2016/0000883 A1 | 1/2016 | Fosgerau et al. |
| 2016/0009777 A1 | 1/2016 | Tolborg et al. |
| 2016/0082118 A1 | 3/2016 | Tolborg et al. |
| 2016/0120951 A1 | 5/2016 | Riber et al. |
| 2016/0184400 A1 | 6/2016 | Neerup et al. |
| 2016/0257729 A1 | 9/2016 | Just et al. |
| 2016/0304576 A1 | 10/2016 | Meier et al. |
| 2016/0347813 A1 | 12/2016 | Hamprecht et al. |
| 2017/0107267 A1 | 4/2017 | Larsen et al. |
| 2018/0141990 A1 | 5/2018 | Riber et al. |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 1076066 A1 | 2/2001 |
| EP | 1196444 B1 | 6/2003 |
| EP | 1329458 A2 | 7/2003 |
| EP | 1421950 A1 | 5/2004 |
| EP | 2025684 A1 | 2/2009 |
| EP | 2028192 A1 | 2/2009 |
| EP | 1525219 B1 | 5/2009 |
| EP | 2112161 A2 | 10/2009 |
| EP | 2565205 A1 | 3/2013 |
| JP | H07504670 A | 5/1995 |
| JP | 2001011095 A | 1/2001 |
| JP | 2007-524584 A | 8/2007 |
| JP | 2007-525495 A | 9/2007 |
| JP | 2011-524418 A | 9/2011 |
| JP | 2012-511900 A | 5/2012 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |
| WO | WO-99/43708 A1 | 9/1999 |

(56) References Cited

FOREIGN PATENT DOCUMENTS

| | | |
|---|---|---|
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | WO-00/34331 A2 | 6/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |
| WO | WO-02/34285 A2 | 5/2002 |
| WO | WO-03/022304 A1 | 3/2003 |
| WO | WO-03/053339 A2 | 7/2003 |
| WO | WO-03/053460 A1 | 7/2003 |
| WO | WO-03/082898 A2 | 10/2003 |
| WO | WO-2004/005342 A1 | 1/2004 |
| WO | WO-2004/062685 A2 | 7/2004 |
| WO | WO-2004/096854 A2 | 11/2004 |
| WO | WO-2005/072045 A2 | 8/2005 |
| WO | WO-2005/077072 A2 | 8/2005 |
| WO | WO-2006/051110 A2 | 5/2006 |
| WO | WO-2006/097537 A2 | 9/2006 |
| WO | WO-2006/121860 A2 | 11/2006 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/095737 A1 | 8/2007 |
| WO | WO-2007/100535 A2 | 9/2007 |
| WO | WO-2008/010101 A2 | 1/2008 |
| WO | WO-2008/071010 A1 | 6/2008 |
| WO | WO-2008/071972 A1 | 6/2008 |
| WO | WO-2008/086086 A2 | 7/2008 |
| WO | WO-2008/101017 A2 | 8/2008 |
| WO | WO-2008/152403 A1 | 12/2008 |
| WO | WO-2008/155257 A1 | 12/2008 |
| WO | WO-2009/030738 A1 | 3/2009 |
| WO | WO-2009/067636 A2 | 5/2009 |
| WO | WO-2009/077737 A2 | 6/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/011439 A2 | 1/2010 |
| WO | WO-2010/014946 A2 | 2/2010 |
| WO | WO-2010/016940 A2 | 2/2010 |
| WO | WO-2010/029159 A1 | 3/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2010/096052 A1 | 8/2010 |
| WO | WO-2010/148089 A1 | 12/2010 |
| WO | WO-2011/006497 A1 | 1/2011 |
| WO | WO-2011/080103 A1 | 7/2011 |
| WO | WO-2011/084808 A2 | 7/2011 |
| WO | WO-2011/088837 A1 | 7/2011 |
| WO | WO-2011/094337 A1 | 8/2011 |
| WO | WO-2011/117415 A1 | 9/2011 |
| WO | WO-2011/117416 A1 | 9/2011 |
| WO | WO-2011/117417 A1 | 9/2011 |
| WO | WO-2011/119657 A1 | 9/2011 |
| WO | WO-2011/134471 A1 | 11/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO-2012/153196 A2 | 11/2012 |
| WO | WO-2012/167744 A1 | 12/2012 |
| WO | WO-2013/041678 A1 | 3/2013 |
| WO | WO-2013/092703 A2 | 6/2013 |
| WO | WO-2013/164483 A1 | 11/2013 |
| WO | WO-2013/192131 A1 | 12/2013 |
| WO | WO-2014/016300 A1 | 1/2014 |
| WO | WO-2014/041195 A1 | 3/2014 |
| WO | WO-2014/096150 A1 | 6/2014 |
| WO | WO-2015/067715 A2 | 5/2015 |
| WO | WO-2015/067716 A1 | 5/2015 |
| WO | WO-2015/124612 A1 | 8/2015 |
| WO | WO-2016/066744 A2 | 5/2016 |
| WO | WO-2016/166289 A1 | 10/2016 |

OTHER PUBLICATIONS

Adelhorst et al., "Structure-activity studies of glucagon-like peptide-1," J Biol Chem. 269(9):6275-6278 (1994).

Ali et al., "Cardiomyocyte glucagon receptor signaling modulates outcomes in mice with experimental myocardial infarction," Mol Metab. 4(2):132-143 (2015).

Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).

Altschul et al., "Local alignment statistics," Methods Enzymol. 266:460-480 (1996).

Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).

Authier et al., "Endosomal proteolysis of glucagon at neutral pH generates the bioactive degradation product miniglucagon-(19-29)," Endocrinology. 144(12):5353-5364 (2003).

Bailey et al., "Glucagon-like peptide-1 and the entero-insular axis in obese hyperglycaemic (ob/ob) mice," Life Sci. 40(6):521-525 (1987).

Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008).

Bedford et al., "Amino acid structure and 'difficult sequences' in solid phase peptide synthesis," Int J Peptide Protein Res. 40(3-4):300-7 (1992).

Behme et al., "Glucagon-like peptide 1 improved glycemic control in Type 1 diabetes," BMC Endocr Disord. 3(1):3 (2003) (9 pages).

Bell, "Heart failure: the frequent, forgotten, and often fatal complication of diabetes," Diabetes Care. 26(8):2433-41 (2003).

Bhat et al., "A DPP-IV-resistant triple-acting agonist of GIP, GLP-1 and glucagon receptors with potent glucose-lowering and insulinotropic actions in high-fat-fed mice," Diabetologia. 56(6):1417-24 (2013).

Blache et al., "Endopeptidase from rat liver membranes, which generates miniglucagon from glucagon," J Biol Chem. 268(29):21748-21753 (1993).

Bork, "Powers and pitfalls in sequence analysis: the 70% hurdle," Genome Research 10, 398-400, 2000.

Bowie et al., "Deciphering the message in protein sequences: tolerance to amino acid substitutions," Science. 247(4948):1306-10 (1990).

Burcelin et al., "Long-lasting antidiabetic effect of a dipeptidyl peptidase IV-resistant analog of glucagon-like peptide-1," Metabolism. 48(2):252-258 (1999).

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.

Buse et al., "The effect of epinephrine, glucagon, and the nutritional state on the oxidation of branched chain amino acids and pyruvate by isolated hearts and diaphragms of the rat," J Biol Chem. 248(2):697-706 (1973).

(56) References Cited

OTHER PUBLICATIONS

Buse, "Progressive use of medical therapies in type 2 diabetes," Diabetes Spectrum. 13(4):211-20 (2000).
Byrne et al., "Inhibitory effects of hyperglycaemia on fed jejunal motility: potential role of hyperinsulinaemia," Eur J Clin Invest. 28(1):72-78 (1998).
Carpenter et al., "Rational design of stable lyophilized protein formulations: some practical advice," Pharm Res. 14(8):969-75 (1997).
Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Chabenne et al., "Optimization of the native glucagon sequence for medicinal purposes," J Diabetes Sci Technol. 4(6):1322-31 (2010).
Chan et al., "Suppression of weight gain by glucagon in obese Zucker rats," Exp Mol Path. 40(3):320-327(1984).
Chen et al., "Evidence that the diabetes gene encodes the leptin receptor: identification of a mutation in the leptin receptor gene in db/db mice," Cell. 84(3):491-5 (1996).
Chen et al., "Tissue-specific expression of unique mRNAs that encode proglucagon-derived peptides or exendin 4 in the lizard," J Biol Chem. 272(7):4108-15 (1997).
Christensen et al., "Lixisenatide, a novel GLP-1 receptor agonist for the treatment of type 2 diabetes mellitus," IDrugs. 12(8):503-13 (2009).
Cleland et al., "The development of stable protein formulations: a close look at protein aggregation, deamidation, and oxidation," Crit Rev Ther Drug Carrier Syst. 10(4):307-77 (1993).
Cohen et al., "Oxyntomodulin suppresses appetite and reduces food intake in humans," J Clin Endocrinol Metab. 88(10):4696-4701 (2003).
Coleman, "Effects of parabiosis of obese with diabetes and normal mice," Diabetologia. 9(4):294-8 (1973).
Communication from the European Patent Office for European Patent Application No. 08875673.9, dated Jul. 4, 2012 (6 pages).
Curriculum Vitae (CV) of Keld Fosgerau, Ph.D. (9 pages).
D'Alessio et al., "Glucagon-like peptide 1 enhances glucose tolerance both by stimulation of insulin release and by increasing insulin-independent glucose disposal," J Clin Invest. 93(5):2263-66(1994).
Dakin et al., "Oxyntomodulin inhibits food intake in the rat," Endocrinology. 142(10):4244-4250 (2001).
Dakin et al., "Peripheral oxyntomodulin reduces food intake and body weight gain in rats," Endocrinology. 145(6):2687-2695 (2004).
Day et al., "A new glucagon and GLP-1 co-agonist eliminates obesity in rodents," Nat Chem Biol. 5(10):749-757 (2009).
De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, mailed Nov. 25, 2013 (29 pages).
Delgado et al., "The uses and properties of PEG-linked proteins," Crit Rev Ther Drug Carrier Syst. 9(3,4):249-304 (1992).
Diamant et al., "Diabetic cardiomyopathy in uncomplicated type 2 diabetes is associated with the metabolic syndrome and systemic inflammation," Diabetologia. 48(8):1669-70 (2005).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Druce et al., "Investigation of structure-activity relationships of Oxyntomodulin (Oxm) using Oxm analogs," Endocrinology. 150(4):1712-1721 (2009).
Drucker, "Glucagon-like peptides," Diabetes. 47(2):159-69 (1998).
Ebert et al., "Gastric inhibitory polypeptide," Clin Gastroenterol. 9(3):679-98 (1980).
Edvell et al., "Initiation of increased pancreatic islet growth in young normoglycemic mice (Umeå+/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions, 2006 (11 pages).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
England et al., "Glucagon carboxyl-terminal derivatives: Preparation, purification and characterization," Biochemistry. 21(5):940-950 (1982).
English translation of Notice of Reasons for Rejection of Japanese Patent Application No. 2015-523532, dated Apr. 24, 2018 (8 pages).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
European Search Report for European Patent Application No. 99610043, dated Jan. 18, 2000 (2 pages).
European Search Report from European Patent Application No. 07016032.0, completed Jan. 28, 2008 (8 pages).
Experimental Report provided in response to opposition filed against European Patent No. 1525219, filed Oct. 5, 2011 (4 pages).
Extended European Search Report for European Patent Application No. 08016668, dated Jan. 14, 2009 (4 pages).
Extended European Search Report for European Patent Application No. 11774431.8, dated Sep. 30, 2013 (11 pages).
Fang et al., "Diabetic cardiomyopathy: evidence, mechanisms, and therapeutic implications," Endocr Rev. 25(4):543-67 (2004).
Farah et al., "Studies on the pharmacology of glucagon," J Pharmacol Exp Ther. 129:49-55 (1960).
Finan et al., "Reappraisal of GIP Pharmacology for Metabolic Diseases," Trends Mol Med. 22(5):359-76 (2016).
Fineman et al., "AC2993 (Synthetic Exendin-4) Improved Glycemic Control in Patients With Type 2 Diabetes During 28 Days of Treatment in a Multicenter, Randomized, Triple-Blind, Placebo-Controlled Study," Diabetes 51 (Supplement 2):A85, Abstract 343-OR, Abstract Book 62"d Scientific Sessions. Poster. Jun. 14-18, (2002).
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51 (Supplement 2):A85, Abstract Book, 62nd Scientific Sessions (2002) (3 pages).
First Examination Report for New Zealand Patent Application No. 702333, dated Jun. 2, 2016 (4 pages).
Fosgerau et al., "The novel GLP-1-gastrin dual agonist, ZP3022, increases beta-cell mass and prevents diabetes in db/db mice," Diabetes Obes Metab. 15(1):62-71 (2013).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gault et al., "A Novel Glucagon-like Peptide-1 (GLP-1 )/Glucagon Hybrid Peptide with Triple-acting Agonist Activity at Glucose-dependent Insulinotropic Polypeptide, GLP-1, and Glucagon Receptors and Therapeutic Potential in High Fat-fed Mice," J Biol Chem. 288(49): 35581-91 (2013).

(56) References Cited

OTHER PUBLICATIONS

Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).
Gault et al., "Glucose-dependent insulinotropic polypeptide analogues and their therapeutic potential for the treatment of obesity-diabetes," Biochem Biophys Res Commun. 308(2): 207-13 (2003).
Gelfanov et al., Discovery and structural optimization of high affinity co-agonists at the glucagon and GLP-1 receptors. Understanding Biology Using Peptides. Sylvie E. Blondelle, 763-764 (2005).
Goldstein et al., "Effects of chronic heart failure on the capacity of glucagon to enhance contractility and adenyl cyclase activity of human papillary muscles," Circulation. 44(4):638-648 (1971).
Gombotz et al. "Biodegradable polymers for protein and peptide drug delivery," Bioconjug Chem. 6(4):332-351 (1995).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).
Greig et al., "Once daily injection of exendin-4 to diabetic mice achieves long-term beneficial effects on blood glucose concentrations," Diabetologia. 42(1):45-50 (1999).
Grieve et al., "Emerging cardiovascular actions of the incretin hormone glucagon-like peptide-1: Potential therapeutic benefits beyond glycaemic control?" Br J Pharmacol. 157(8):1340-51 (2009).
Grounds of Appeal by F. Hoffmann-La Roche AG for European Patent No. 1525219, filed Aug. 10, 2012 (35 pages).
Grounds of Appeal by Novo Nordisk A/S for European Patent No. 1525219, filed Aug. 3, 2012 (27 pages).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-90 (1995).
Gutniak et al., "Antidiabetogenic effect of glucagon-like peptide-1 (7-36)amide in normal subjects and patients with diabetes mellitus," N Engl J Med. 326(20):1316-22 (1992).
Göke et al., "Distribution of GLP-1 binding sites in the rat brain: Evidence that exendin-4 is a ligand of brain GLP-1 binding sites," Eur J Neurosci. 7(11):2294-2300 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Haffner et al., "Intensive lifestyle intervention or metformin on inflammation and coagulation in participants with impaired glucose tolerance," Diabetes. 54(5):1566-72 (2005).
Hamad et al., "Pharmacologic therapy of chronic heart failure," Am J Cardiovasc Drugs. 7(4):235-48 (2007).
Hansson, "Inflammation, atherosclerosis, and coronary artery disease," N Engl J Med. 352(16):1685-95 (2005).
Harikae, "The effects of a behavioral program in the obese NIDDM patients-observations on daily activity, degree of obesity and blood sugar control," Bulletin of the School of Nursing, Yamaguchi Prefectural University 2:1-13/E (1998) (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-81 (1984).
Hjorth et al., "Glucagon and glucagon-like peptide 1: Selective receptor recognition via distinct peptide epitopes," J Biol Chem. 269(48):30121-30124 (1994).
Holst, "Enteroglucagon," Annu Rev Physiol. 59:257-71 (1997).
Holst, "Glucagon-like peptide-1, a gastrointestinal hormone with a pharmacological potential," Curr Med Chem. 6(11):1005-17 (1999).
Holst, "The physiology of glucagon-like peptide 1," Physiol Rev. 87(4): 1409-39 (2007).

Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
Hui et al., "The short half-life of glucagon-like peptide-1 in plasma does not reflect its long-lasting beneficial effects," Eur J Endocrinol. 146(6):863-9 (2002).
ICH Harmonised Tripartite Guideline, Feb. 5, 1998 (39 pages).
Igaki et al., "Investigation of effectiveness of low intensity exercise on body fat reduction in diabetics," J.Japan Phys Ther Assoc, 26:270-4 (1999). English abstract included.
Ingwall et al., "Is the failing heart energy starved? On using chemical energy to support cardiac function," Circ Res. 95(2):135-45 (2004).
International Dictionary of Medicine and Biology in Three Volumes: vol. II. John Wiley & Sons, New York, 1328 (1986) (3 pages).
International Preliminary Examination Report for International Application No. PCT/DK03/00463, dated Sep. 20, 2004 (5 pages).
International Preliminary Report on Patentability for International Patent Application No. PCT/EP2014/073970, dated May 10, 2016 (10 pages).
International Preliminary Report on Patentability for International Patent Application No. PCT/EP2014/073971, dated May 10, 2016 (5 pages).
International Preliminary Report on Patentability for PCT/EP2013/069286, completed Jan. 19, 2015 (40 pages).
International Preliminary Reporton Patentability for PCT/GB2008/002041, dated Dec. 17, 2009 (7 pages).
International Search Report and Written Opinion for International Application No. PCT/EP2015/075120, dated Jul. 15, 2016 (13 pages).
International Search Report and Written Opinion for International Application No. PCT/IB2012/001090, dated Jan. 25, 2013 (15 pages).
International Search Report and Written Opinion for International Patent Application No. PCT/EP2012/071766, dated Feb. 15, 2013 (9 pages).
International Search Report and Written Opinion for International Patent Application No. PCT/EP2014/073970, dated Aug. 26, 2015 (15 pages).
International Search Report and Written Opinion for International Patent Application No. PCT/EP2014/073971, dated Mar. 5, 2015 (7 pages).
International Search Report and Written Opinion for PCT/EP2013/059319, dated Sep. 12, 2013 (12 pages).
International Search Report and Written Opinion for PCT/EP2013/065519, dated Dec. 6, 2013 (11 pages).
International Search Report and Written Opinion for PCT/EP2013/069286, dated Dec. 18, 2013 (16 pages).
International Search Report and Written Opinion for PCT/EP2016/058359, dated Jul. 15, 2016 (13 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2010/000099, dated Dec. 2, 2010 (2 pages).
International Search Report for International Application No. PCT/DK2011/000067, dated Dec. 9, 2011 (4 pages).
International Search Report for International Application No. PCT/DK2011/050133, dated Oct. 6, 2011 (5 pages).

(56) References Cited

OTHER PUBLICATIONS

International Search Report for International Application No. PCT/IB2012/000134, dated Jun. 25, 2012 (3 pages).
International Search Report for International Application No. PCT/DK2011/050018, dated May 30, 2011 (6 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 386(7):679-87 (2005).
Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).
Jaya et al., "Mechanism of hypocholesterolemic action of glucagon," J Biosci. 12(2):111-4 (1987).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation.," Circulation. 119(14):1977-2016 (2009).
Joshi et al., "The estimation of glutaminyl deamidation and aspartyl cleavage rates in glucagon," Int J Pharm. 273(1-2):213-219 (2004).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Kawashima et al., "Case of pancreatic diabetes with improvement in carbohydrate and lipid metabolism brought about by injections of a small quantity of glucagon," The Journal of the Japanese Society of Internal Medicine. 88(2):336-8 (1999) (English Abstract Included).
Kitamura, "Is the "drug holiday" harmful?" Keio J Med. 25(3):131-7 (1976).
Kiyose et al., "Glucose tolerance screening method using a combination of fasting plasma glucose and hemoglobin A1c," J. Japan Diab Soc, 30:325-331 (1987). English abstract included.
Knudsen et al., "Potent derivatives of glucagon-like peptide-1 with pharmacokinetic properties suitable for once daily administration," J Med Chem. 43(9):1664-9 (2000).
Korc, "Islet growth factors: curing diabetes and preventing chronic pancreatitis?" J Clin Invest. 92(3):1113-4 (1993).
Krchnák et al., "Aggregation of resin-bound peptides during solid-phase peptide synthesis. Prediction of difficult sequences," Int J Pept Protein Res. 42(5):450-4 (1993).
Larsen et al., "Glucagon-like peptide-1 infusion must be maintained for 24 h/day to obtain acceptable glycemia in type 2 diabetic patients who are poorly controlled on sulphonylurea treatment," Diabetes Care. 24(8):1416-21 (2001).
Larsen et al., "Sequence-assisted peptide synthesis (SAPS)," J Peptide Res. 52(6):470-6 (1998).
Lazar et al., "Transforming growth factor alpha: mutation of aspartic acid 47 and leucine 48 results in different biological activities," Mol. Cell. Biol. 8, 1247-52, 1988.
Lefébvre, "The intriguing diversity of the glucagon gene products," Curr Diab Rep. 2(3):201-2 (2002).
Leiter et al., "Influence of dietary carbohydrate on the induction of diabetes in C57BL/KsJ-db/db diabetes mice," J Nutr. 113(1):184-95 (1983).
Levey et al., "Activation of adenyl cyclase by glucagon in cat and human heart," Circ Res. 24(2):151-6(1969).

Lopaschuk et al., "Measurements of fatty acid and carbohydrate metabolism in the isolated working rat heart," Mol Cell Biochem. 172(1-2):137-47 (1997).
Lorenz et al., "Recent progress and future options in the development of GLP-1 receptor agonists for the treatment of diabesity," Bioorg Med Chem Lett. 23(14):4011-8 (2013).
Loyter et al., "Mechanisms of DNA uptake by mammalian cells: fate of exogenously added DNA monitored by the use of fluorescent dyes," Proc Natl Acad Sci USA. 79(2):422-6 (1982).
Lvoff et al., "Glucagon in heart failure and in cardiogenic shock. Experience in 50 patients," Circulation. 45(3):534-42 (1972).
López-Delgado et al., "Effects of glucagon-like peptide 1 on the kinetics of glycogen synthase a in hepatocytes from normal and diabetic rats," Endocrinology. 139(6):2811-17 (1998).
Madsen et al., "Structure-activity and protraction relationship of long-acting glucagon-like peptide-1 derivatives: importance of fatty acid length, polarity, and bulkiness," J Med Chem. 50(24):6126-32 (2007).
Malde et al., "Understanding interactions of gastric inhibitory polypeptide (GIP) with its G-protein coupled receptor through NMR and molecular modeling," J Pept Sci. 13(5):287-300 (2007).
Manhart et al., "Structure-function analysis of a series of novel GIP analogues containing different helical length linkers," Biochemistry. 42(10):3081-8 (2003).
Manning et al., "Stability of protein pharmaceuticals," Pharm Res. 6(11):903-18 (1989).
Matsumoto et al., "Plasma Incretin Levels and Dipeptidyl Peptidase-4 Activity in Patients with Obstructive Sleep Apnea," Ann Am Thorac Soc. 13(8):1378-87 (2016).
Matsuyama, "Glucagon and diabetes," Shijonawate Gakuen Bulletin of Faculty of Rehabilitation. 7:1-12 (2011) (English Abstract Included).
Matthes et al., "Simultaneous rapid chemical synthesis of over one hundred oligonucleotides on a microscale," EMBO J. 3(4):801-5 (1984).
Mayer et al., "Effect of glucagon on cyclic 3',5'-AMP, phosphorylase activity and contractility of heart muscle of the rat," Circ Res. 26(2):225-33 (1970).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Inti J Pharm Sci Res. 3(10):3565-3576 (2012).
Meier et al., "Absence of a memory effect for the insulinotropic action of glucagon-like peptide 1 (GLP-1) in healthy volunteers," Horm Metab Res. 35(9):551-6 (2003).
Meurer et al., "Properties of native and in vitro glycosylated forms of the glucagon-like peptide-1 receptor antagonist exendin (9-39)," Metabolism. 48(6):716-24 (1999).
Meyer et al., Effects of conformation on the Chemical Stability of Pharmaceutically Relevant Polypeptides. *Rational design of stable protein formulations*. Carpenter and Manning, 85-6 (2002).
Mojsov, "Structural requirements for biological activity of glucagon-like peptide-I," Int J Pept Protein Res. 40(3-4):333-43 (1992).
Nauck et al., "Glucagon-like peptide 1 and its potential in the treatment of non-insulin-dependent diabetes mellitus," Horm Metab Res. 29(9):411-6 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem. 67(5):1982-91 (1996).
NCBI Blast for Accession No. 721913A, retrieved on Dec. 15, 2009 (1 page).
Neubauer et al., "Myocardial phosphocreatine-to-ATP ratio is a predictor of mortality in patients with dilated cardiomyopathy," Circulation. 96(7):2190-6 (1997) (9 pages).
Neumann et al., "Gene transfer into mouse lyoma cells by electroporation in high electric fields," EMBO J. 1(7):841-5(1982).

(56) References Cited

OTHER PUBLICATIONS

Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-8 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-61 (2004).
Notarized Affidavit from the British Library regarding European Journal of Endocrinology, vol. 146, No. 6, Jun. 2002, mailed Apr. 21, 2011 (5 pages).
Notice of Allowance and Allowed Claims for U.S. Appl. No. 13/383,783, dated Jun. 22, 2015 (5 pages).
Notice of Allowance, previously Allowed Claims and Amendment after Allowance for U.S. Appl. No. 13/704,299, dated Jun. 26, 2015 (15 pages).
Notice of Allowance, previously Allowed Claims and Amendment after Allowance for U.S. Appl. No. 14/029,529, dated Jun. 29, 2015 (14 pages).
Notice of Appeal of Opposition Decision for European Patent No. 1525219 by F. Hoffmann-La Roche AG, filed May 21, 2012 (1 page).
Notice of Appeal of Opposition Decision for European Patent No. 1525219 by Novo Nordisk A/S, filed Apr. 23, 2012 (1 page).
Notice of Opposition to a European Patent for European Patent No. 1525219 on behalf of Novo Nordisk A/S, dated Feb. 25, 2010 (24 pages).
O'Shaughnessy et al., "Alpha-difluoromethylornithine as treatment for metastatic breast cancer patients," Clin Cancer Res. 5(11):3438-44 (1999) (8 pages).
Office Action for Colombian U.S. Appl. No. 16/089,238, dated Sep. 13, 2017 (18 pages).
Opposition to European Patent No. 1525219 on behalf of F. Hoffman-La Roche AG, dated Feb. 25, 2010 (34 pages).
Orskov, "Glucagon-like peptide-1, a new hormone of the entero-insular axis," Diabetologia. 35(8):701-11 (1992).
Overgaard et al., "Inotropes and vasopressors: review of physiology and clinical use in cardiovascular disease," Circulation. 118(10):1047-56 (2008).
Owens et al., "Insulins today and beyond," Lancet. 358(9283):739-46 (2001).
Pan et al., "Design of a long acting peptide functioning as both a glucagon-like peptide-1 receptor agonist and a glucagon receptor antagonist," J Biol Chem. 281 (18):12506-12515 (2006).
Parkes et al., "Insulinotropic actions of exendin-4 and glucagon-like peptide-1 in vivo and in vitro," Metabolism. 50(5):583-9 (2001).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Partial European Search Report for European Patent Application No. 03005786, dated Oct. 23, 2003 (6 pages).
Partial European Search Report for European Patent Application No. 99610043, dated Jan. 18, 2000 (4 pages).
Patel et al., "Co-agonist of glucagon and GLP-1 reduces cholesterol and improves insulin sensitivity independent of its effect on appetite and body weight in diet-induced obese C57 mice," Can J Physiol Pharmacol. 91(12):1009-15 (2013).
Patterson et al., "A hydrophobic site on the GLP-1 receptor extracellular domain orients the peptide ligand for signal transduction," Mol Metab. 2(2):86-91 (2013).
PDR Medical Dictionary. Medical Economics, Montvale, New Jersey, p. 522 (1995) (3 pages).
Pederson et al., "Improved glucose tolerance in Zucker Fatty Rats by oral administration of the dipeptidyl peptidase IV inhibitor isoleucine thiazolidide," Diabetes. 47(8):1253-8 (1998).

Perfetti et al., "Glucagon-like peptide-1: a major regulator of pancreatic beta-cell function," Eur J Endocrinol. 143(6):717-25 (2000).
Periasamy et al., "Molecular basis of diastolic dysfunction," available in PMC Jul. 6, 2009, published in final edited form as: Heart Fail Clin. 4(1):13-21 (2008) (13 pages).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447 (2002) (2 pages).
Pocai et al., "Glucagon-like peptide 1/glucagon receptor dual agonism reverses obesity in mice," Diabetes. 58(10):2258-66 (2009).
Pocai, "Glucagon signaling in the heart: activation or inhibition?" Mol Metab. 4(2):81-2 (2015).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).
Poon et al., "Exenatide improves glycemic control and reduces body weight in subjects with type 2 diabetes: a dose-ranging study," Diabetes Technol Ther. 7(3):467-77 (2005).
Pratesi et al., "Poly-L-aspartic acid as a carrier for doxorubicin: a comparative in vivo study of free and polymer-bound drug," Br J Cancer. 52(6):841-848 (1985).
Prescribing information for Victoza, 6 mg/ml solution for injection in pre-filled pen, as submitted on Aug. 13, 2012 as part of a Grounds of Appeal for European Patent No. 1525219 (31 pages).
Pridal et al., "Absorption of glucagon-like peptide-1 can be protracted by zinc or protamine," Int J Pharm. 136(1-2):53-9 (1996).
Protest of U.S. Appl. No. 12/664,534 Pursuant 37 CFR 1.291, dated Jan. 13, 2010 (14 pages).
Raufman et al., "Exendin-3, a novel peptide from *Heloderma horridum* venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).
Raufman et al., "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).
Raufman, "Bioactive peptides from lizard venoms," Regul Pept. 61(1):1-18 (1996).
Ritzel et al., "A synthetic glucagon-like peptide-1 analog with improved plasma stability," J Endocrinol. 159(1):93-102 (1998).
Roach et al., "Improved postprandial glycemic control during treatment with humalog Mix25, a novel protamine-based insulin lispro formulation. Humalog Mix25 Study Group," Diabetes Care. 22(8):1258-61 (1999).
Robberecht et al., "Comparative efficacy of seven synthetic glucagon analogs, modified in position 1,2, and/or 12, on liver and heart adenylate cyclase from rat," Peptides. 7(Suppl 1):109-12 (1986).
Rolin et al., "The long-acting GLP-1 derivative NN2211 ameliorates glycemia and increases beta-cell mass in diabetic mice," Am J Physiol Endocrinol Metab. 283(4):E745-52 (2002).
Rooman et al., "Gastrin stimulates beta-cell neogenesis and increases islet mass from transdifferentiated but not from normal exocrine pancreas tissue," Diabetes. 51(3):686-90 (2002).
Rose et al., "Insulin proteinase liberates from glucagon a fragment known to have enhanced activity against Ca2+ + Mg2+-dependent ATPase," Biochem J. 256(3):847-51 (1988).
Runge et al., "Differential structural properties of GLP-1 and exendin-4 determine their relative affinity for the GLP-1 receptor N-terminal extracellular domain," Biochemistry. 46(19):5830-40 (2007).
Saraceni et al., "Effects of glucagon-like peptide-1 and long-acting analogues on cardiovascular and metabolic function," Drugs R D. 8(3):145-53 (2007).
Sowden et al., "Oxyntomodulin increases intrinsic heart rate in mice independent of the glucagon-like peptide-1 receptor," Am J Physiol Regul Integr Comp Physiol. 292(2): R962-70 (2007) (10 pages).

(56) References Cited

OTHER PUBLICATIONS

Sporn et al., "Chemoprevention of cancer," Carcinogenesis. 21(3):525-530 (2000).
Staffers et al., "Insulinotropic glucagon-like peptide 1 agonists stimulate expression of homeodomain protein IDX-1 and increase islet size in mouse pancreas," Diabetes. 49(5):741-8 (2000).
Sturm et al., "Structure-function studies on positions 17, 18, and 21 replacement analogues of glucagon: the importance of charged residues and salt bridges in glucagon biological activity," J Med Chem. 41(15): 2693-700 (1998) (8 pages).
Suarez-Pinzon et al., "Combination therapy with epidermal growth factor and gastrin increases beta-cell mass and reverses hyperglycemia in diabetic NOD mice," Diabetes. 54(9):2596-601 (2005).
Suarez-Pinzon et al., "Combination therapy with glucagon-like peptide-1 and gastrin induces beta-cell neogenesis from pancreatic duct cells in human islets transplanted in immunodeficient diabetic mice," Cell Transplant. 17(6):631-40 (2008).
Suarez-Pinzon et al., "Combination therapy with glucagon-like peptide-1 and gastrin restores normoglycemia in diabetic NOD mice," Diabetes. 57(12):3281-8 (2008) (10 pages).
Table of Claims anticipated by WO 00/09666, as submitted on Feb. 25, 2010 as part of an Opposition to European Patent No. 1525219 (9 pages).
Tang-Christensen et al., "Central administration of GLP-1-(7-36) amide inhibits food and water intake in rats," Am J. Physiol. 271(4 Pt2):R848-56 (1996).
Thorkildsen et al., "The exendin analogue ZP10 increases insulin mRNA expression in db/db mice," Nedergaard Symposium, Odense, Denmark, Jan. 24, 2002 (Poster presentation) (1 page).
Thorkildsen et al., "ZP10—A New GLP-1 agonist that increases insulin mRNA expression," Nedergaard Symposium, Odense, Denmark, Jan. 24, 2002 (abstract only) (1 page).
Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation (1 page).
Tomita et al., "Pancreatic islets of obese hyperglycemic mice (ob/ob)," Pancreas. 7(3):367-375 (1992).
Tourrel et al., "Glucagon-like peptide-1 and exendin-4 stimulate beta-cell neogenesis in streptozotocin-treated newborn rats resulting in persistently improved glucose homeostasis at adult age," Diabetes 50(7):1562-70 (2001).
Tourrel et al., "Persistent improvement of type 2 diabetes in the Goto-Kakizaki rat model by expansion of the beta-cell mass during the prediabetic period with glucagon-like peptide-1 or exendin-4," Diabetes. 51(5):1443-52 (2002).
Transition Therapeutics Inc., "Lilly and Transition Therapeutics announce licensing and collaboration agreement. Lilly to acquire exclusive rights to gastrin based therapies program for diabetes," <http://www.transitiontherapeutics.com/media/news.php>, retrieved May 28, 2015 (2 pages).
Transition Therapeutics Inc., "Positive preclinical data with Novo Nordisk A/S long-acting GLP-1 analog and gastrin combination presented at American Diabetes Association Meeting," <http://www.transitiontherapeutics.com/media/news.php>, retrieved on May 28, 2015 (1 page).
Translation of Office Action for Japanese Patent Application No. 2004-518465, dated Nov. 24, 2009 (6 pages).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Turton et al., "A role for glucagon-like peptide-1 in the central regulation of feeding," Nature 379(6560):69-72(1996).
U.S. Appl. No. 14/095,667, filed Dec. 3, 2013 (99 pages).
U.S. Appl. No. 14/116,268, filed Nov. 7, 2013 (164 pages).
U.S. Appl. No. 15/852,458, filed Dec. 22, 2017 (57 pages).
U.S. Appl. No. 60/132,018, filed Apr. 30, 1999 (101 pages).
U.S. Appl. No. 61/784,294, filed Mar. 14, 2013 (54 pages).

Uesaka et al., "Glucagon-like peptide isolated from the eel intestine: Effects on atrial beating," J Exp Bio. 204(Pt 17):3019-26 (2001).
Underwood et al., "Crystal structure of glucagon-like peptide-1 in complex with the extracellular domain of the glucagon-like peptide-1 receptor," J Biol Chem. 285(1):723-30 (2010).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Uttenthal et al., "Molecular forms of glucagon-like peptide-1 in human pancreas and glucagonomas," J Clin Endocrinol Metabol. 61(3):472-479 (1985).
Villa-Komaroff et al., "A bacterial clone synthesizing proinsulin," Proc Natl Acad Sci USA. 75(8):3727-31 (1978).
Wang et al., "Glucagon-like peptide-1 treatment delays the onset of diabetes in 8 week-old db/db mice," Diabetologia. 45(9):1263-73 (2002).
Warnica, "Acute coronary syndromes (Heart Attack; Myocardial Infarction; Unstable Angina)," <http://www.merckmanuals.com/home/heart_and_blood_vessel_disorders/coronary_artery_disease/acute_coronary_syndromes_heart_attack_myocardial_infarction_unstable_angina.html?qt=congestive heart failure&alt=sh>, retrieved on Feb. 8, 2015 (8 pages).
Wermuth et al., "Glossary of terms used in medicinal chemistry," Pure & Appl Chem. 70(5):1129-43 (1998).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21)7287-7302 (1983).
Wodarz et al., "Specific therapy regimes could lead to long-term immunological control of HIV," Proc Natl Acad Sci U.S.A. 96(25):14464-9 (1999).
Written Opinion for PCT/DK2011/000072, dated Dec. 6, 2011 (6 pages).
Written Opinion for Singapore Application No. 201209089-0, dated Nov. 8, 2013 (10 pages).
Written Opinion for Singapore Patent Application No. 2012078382, dated Feb. 17, 2015 (12 pages).
Written Opinion of the International Searching Authority for PCT/GB2008/002041, dated Sep. 9, 2008 (6 pages).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes. 48(5):1026-34 (1999).
Young et al., "Physiological and genetic factors affecting transformation of Bacillus subtilis," J Bacteriol. 81:823-9 (1961).
Zalipsky, "Functionalized poly(ethylene glycol) for preparation of biologically relevant conjugates," Bioconjug Chem. 6(2):150-165 (1995).
Zander et al., "Additive glucose-lowering effects of glucagon-like peptide-1 and metformin in type 2 diabetes," Diabetes Care. 24(4):720-5 (2001).

(56) References Cited

OTHER PUBLICATIONS

Zhao et al., "Direct effects of glucagon-like peptide-1 on myocardial contractility and glucose uptake in normal and postischemic isolated rat hearts," J Pharmacol Exp Ther. 317(3):1106-13 (2006).

Zhou et al., "Glucagon-like peptide 1 and exendin-4 convert pancreatic AR42J cells into glucagon- and insulin-producing cells," Diabetes. 48(12): 2358-66 (1999).

Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).

Fernando et al., "Identifying novel agonists for the glucagon receptor," ACS Spring 2022 Conference, Mar. 20-24, 2022 (Abstract only).

Ng et al., "Predicting the effects of amino acid substitutions on protein function," Annu Rev Genomics Hum Genet. 7:61-80 (2006).

Pospisilik et al., "Metabolism of glucagon by dipeptidyl peptidase IV (CD26)," Regul Pept. 96(3):133-41 (Jan. 12, 2001).

Carbone et al., "Modern criteria to establish human cancer etiology," Cancer Res. 64(15):5518-24 (Aug. 1, 2004).

"Glucagon (Injection Route)," Mayo Clinic, last updated Feb. 1, 2022 (11 pages).

Figures 1A-1D
FIG. 1A
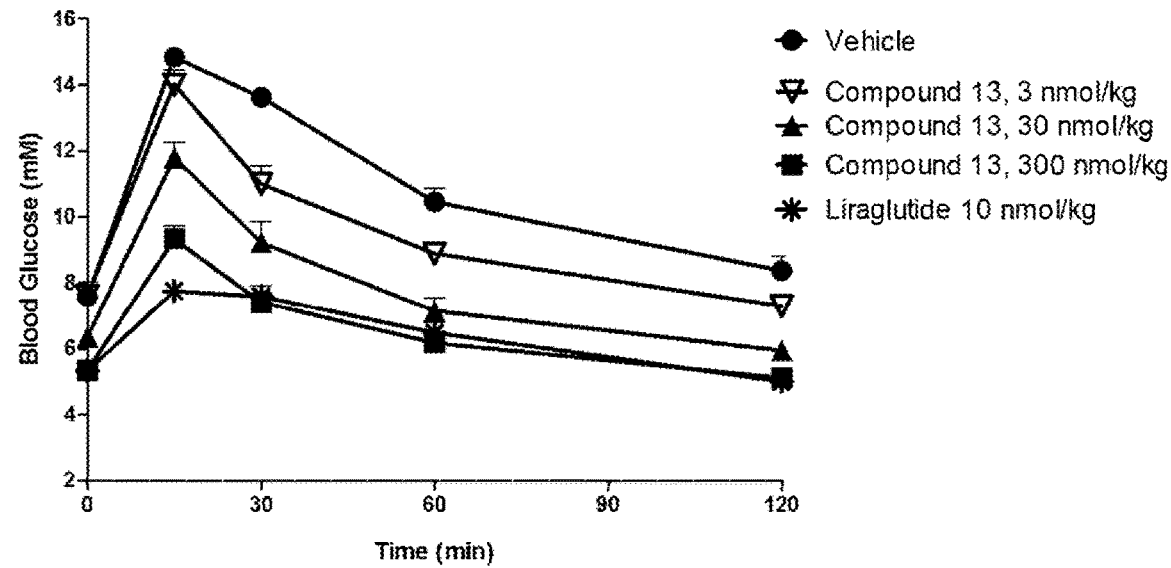
FIG. 1B
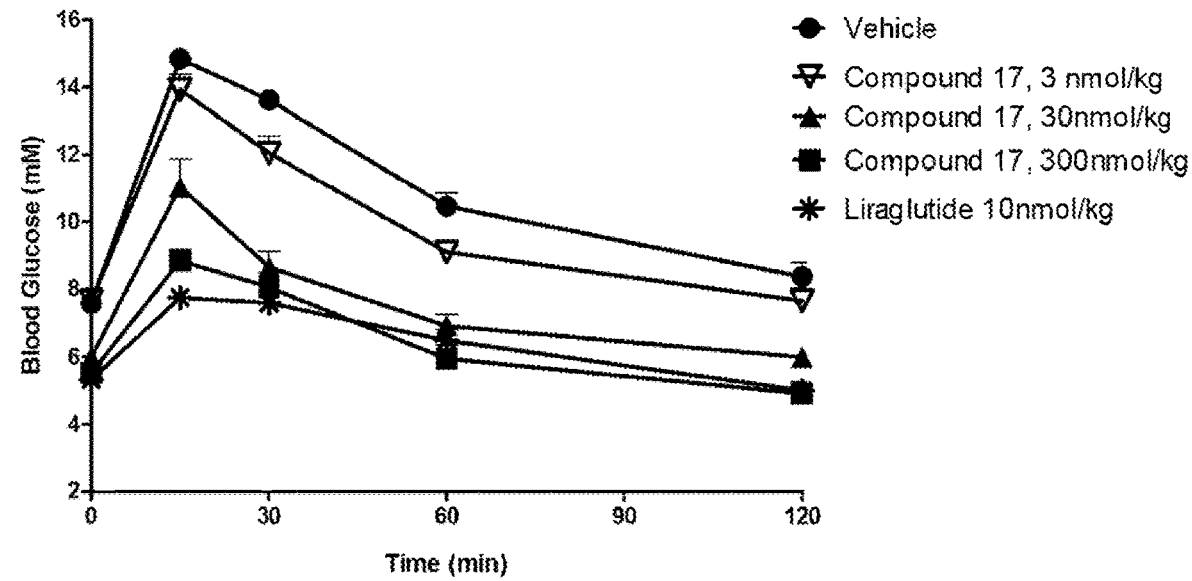

Figures 2A-2E
FIG. 2A
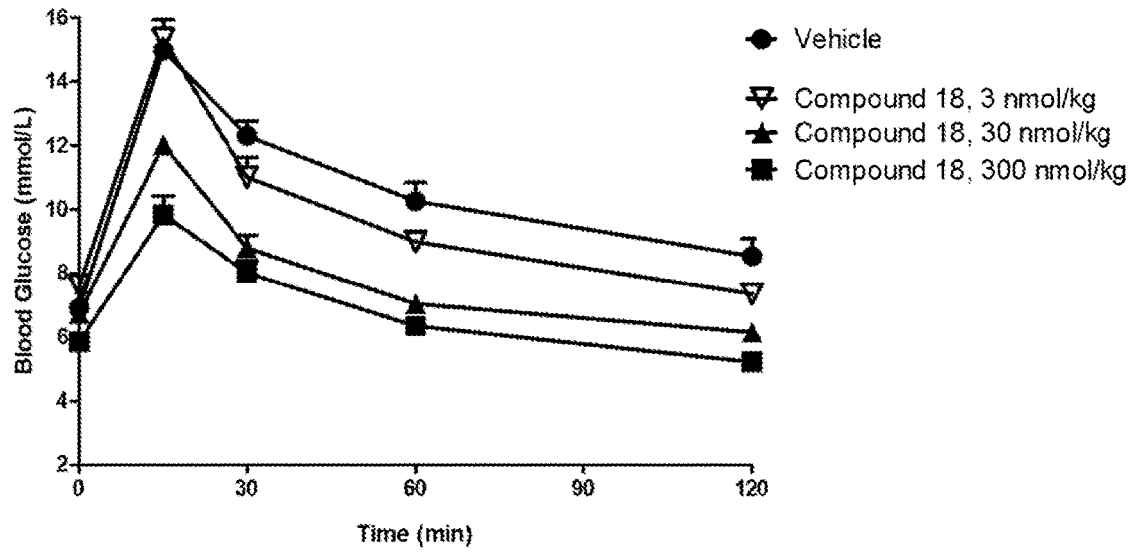
FIG. 2B
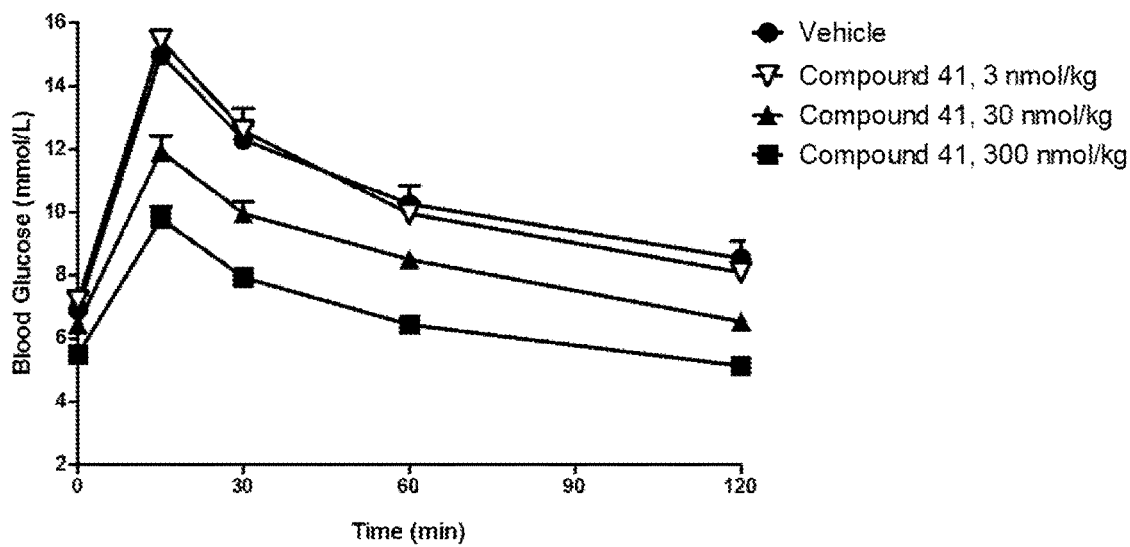

Figures 4A-4E
FIG. 4A
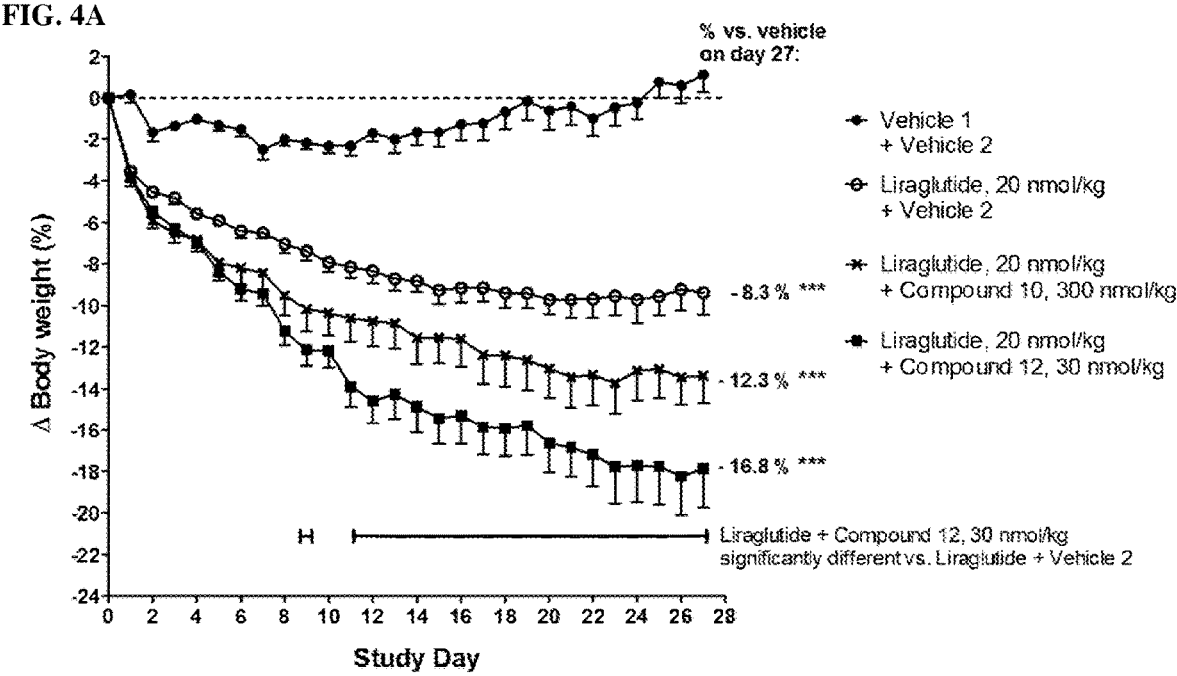
FIG. 4B
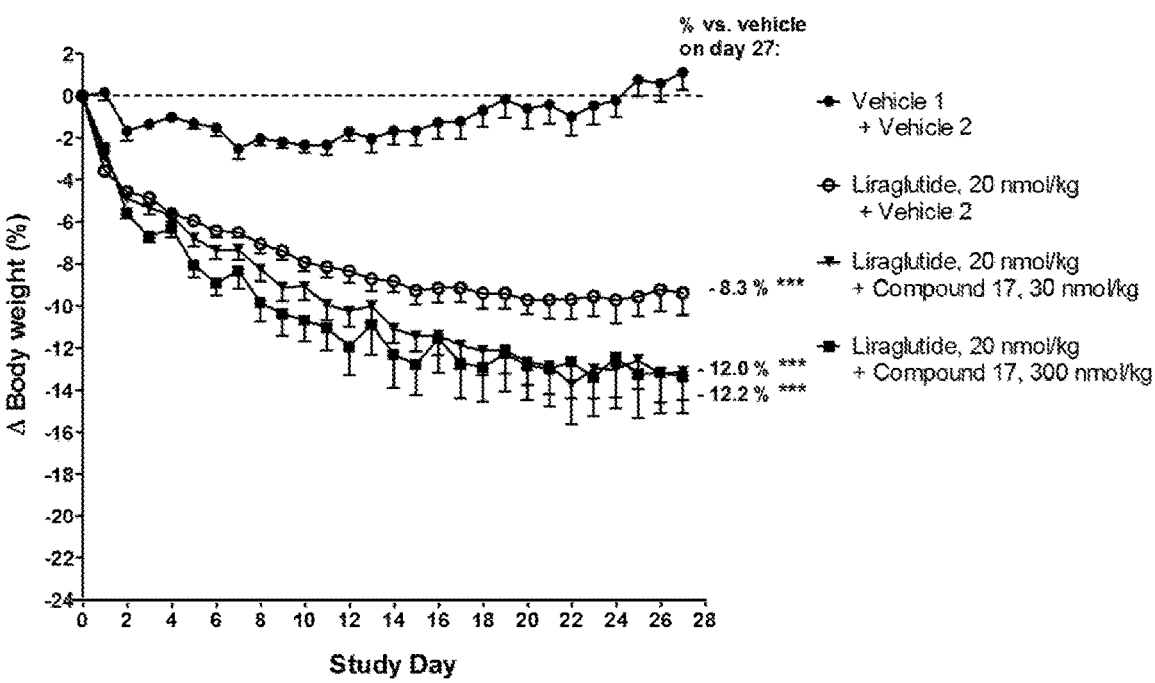

GIP AGONIST COMPOUNDS AND METHODS

FIELD OF THE INVENTION

The invention relates to compounds having agonist activity at the GIP receptor, and to their use in the treatment of metabolic disorders.

SEQUENCE LISTING

The instant application contains a Sequence Listing which has been submitted electronically in ASCII format and is hereby incorporated by reference in its entirety. Said ASCII copy, created on Apr. 1, 2021 is named "50412-100003 Sequence Listing" and is 70,389 bytes in size.

BACKGROUND OF THE INVENTION

Diabetes and obesity are increasing health problems globally and are associated with various other diseases, particularly cardiovascular diseases (CVD), obstructive sleep apnea, stroke, peripheral artery disease, microvascular complications and osteoarthritis. There are 246 million people worldwide with diabetes, and by 2025 it is estimated that 380 million will have diabetes. Many have additional cardiovascular risk factors including high/aberrant LDL and triglycerides and low HDL. Cardiovascular diseases account for about 50% of the mortality in people with diabetes, and the morbidity and mortality rates relating to obesity and diabetes underscore the medical need for efficacious treatment options.

Glucose-dependent insulinotropic polypeptide ("GIP", also known as "gastric inhibitory polypeptide") is a 42-residue peptide secreted by enteroendocrine K-cells of the small intestine into the bloodstream in response to oral nutrient ingestion. GIP inhibits the secretion of gastric acid, and it has been shown to be a potent stimulant for the secretion of insulin from pancreatic beta cells after oral glucose ingestion (the "incretin effect") (Creutzfeldt, W., et al, 1979, Diabetologia, 16:75-85).

Insulin release induced by the ingestion of glucose and other nutrients is due to both hormonal and neural factors (Creutzfeldt, W., et al, 1985, Diabetologia, 28:565-573). Several gastrointestinal regulatory peptides have been proposed as incretins, and among these candidates, only GIP and glucagon-like peptide 1 ("GLP-1") appear to fulfill the requirements to be considered physiological stimulants of postprandial insulin release (Nauck, et al, 1989, J. Clin. Endocrinol Metab., 69:654-662). It has been shown that the combined effects of GIP and GLP-1 are sufficient to explain the full incretin effect of the enteroinsular axis (Fehmann, H. C, et al, 1989, FEBS Lett, 252: 109-112).

As is well known to those skilled in the art, the known and potential uses of GIP are varied and multitudinous. Thus, the administration of the compounds of this invention for purposes of eliciting an agonist effect can have the same effects and uses as GIP itself. These varied uses of GIP may be summarized as follows: treating a disease selected from the group consisting of type 1 diabetes, type 2 diabetes (Visboll, T., 2004, Dan. Med. Bull, 51:364-70), insulin resistance (WO 2005/082928), obesity (Green, B. D., et al, 2004, Current Pharmaceutical Design, 10:3651-3662), metabolic disorder (Gault, V. A., et al, 2003, Biochem. Biophys. Res. Commun., 308:207-213), central nervous system disease, neurodegenerative disease, congestive heart failure, hypoglycemia, and disorders wherein the reduction of food intake and weight loss are desired. In pancreatic islets, GIP not only enhances insulin secretion acutely, but it also stimulates insulin production through enhancement of proinsulin transcription and translation (Wang, et al, 1996, Mol Cell. Endocrinol, 116:81-87) and enhances the growth and survival of pancreatic beta cells (Trumper, et al, 2003, Diabetes, 52:741-750). In addition to effects on the pancreas to enhance insulin secretion, GIP also has effects on insulin target tissues directly to lower plasma glucose: enhancement of glucose uptake in adipose (Eckel, et al, 1979, Diabetes, 28: 1141-1142) and muscle (O'Harte, et al, 1998, J. Endocrinol, 156:237-243), and inhibition of hepatic glucose production (Elahi, D., et al, 1986, Can. J. Physiol. Pharmacol, 65:A18).

Recently, it has been reported that body weight loss associated with GLP-1 agonist treatment, is enhanced when GLP-1 and GIP are co-administered (Finan, Sci Transl Med. 2013; 5(209):209ra151. Irwin N et al, 2009, Regul Pept; 153: 7076. Gault et al, 2011, Clin Sci (Lond); 121:107-117). For instance, Finan and colleges demonstrated significant body weight loss in diet-induced obese (DIO) mice after sub-chronic co-administration with an acylated GIP agonist and an acylated GLP-1 agonist. The co-administration decreased body weight and fat mass to a greater extent than either mono-agonist alone. Evidence also suggests that GLP-1 and GIP have additive effects on glycemic control (Gault et al, 2011, Clin Sci (Lond); 121:107-117). A study by Gault et al showed that sub-chronic co-administration with a GLP-1 analogue, and an acylated GIP analogue resulted in greater glucose-lowering and insulinotropic actions during an intraperitoneal glucose tolerance test in ob/ob mice than injection with the GLP-1 agonist or the GIP agonist alone. Thus, GIP agonists may be particular effective in improving glycaemic control and reducing body weight when they are administered in combination with a GLP-1 receptor agonist (as part of the same pharmaceutical formulation or as separate formulations).

The use of unmodified GIP as a therapeutic, however, is limited by the short in vivo half-life of about 2 minutes (Said and Mutt, 1970, Science, 169:1217-1218). In serum, both incretins, GIP and GLP-1, are degraded by dipeptidyl peptidase IV ("DPPIV"). Improving the stability of GIP to proteolysis not only maintains the activity of GIP at its receptor but, more importantly, prevents the production of GIP fragments, some of which act as GIP receptor antagonists (Gault, et al., 2002, J. Endocrinol, 175:525-533). Reported modifications have included protection of the N-terminus of GIP from proteolysis by DPPIV through modification of the N-terminal tyrosine (O'Harte, et al, 2002, Diabetologia, 45: 1281-1291), mutation of the alanine at position 2 (Hinke, et al, 2002, Diabetes, 51:656-661), mutation of glutamic acid at position 3 (Gault, et al, 2003, Biochem. Biophys. Res. Commun., 308:207-213), and mutation of alanine at position 13 (Gault, et al, 2003, Cell Biol. International, 27:41-46), The following patent applications have been filed related to the effects of GIP analogues on the function of various target organs and their potential use as therapeutic agents:

PCT publication WO 00/58360 discloses peptidyl analogues of GIP which stimulate the release of insulin. In particular, this application discloses specific peptidyl analogues comprising at least 15 amino acid residues from the N-terminal end of GIP(I 42.

PCT publication WO 03/082898 discloses C-terminal truncated fragments and N-terminal modified analogues of GIP, as well as various GIP analogues with a reduced peptide bond or alterations of the amino acids close to the DPPFVspecific cleavage site. This application further discloses analogues with different linkers between potential receptor binding sites of GIP. The compounds of this application are alleged to be useful in treating GIP-receptor mediated conditions, such as non-insulin dependent diabetes mellitus and obesity. Moreover, among other therapeutic effects of the compounds of the present invention as illustrated herein, tighter control of plasma glucose levels may prevent long-term diabetic complications, thereby providing an improved quality of life for patients. In addition to improving blood glucose control, GIP may also enhance GLP-1-mediated body weight loss.

Conjugation of GIP analogues to e.g, PEG(poly ethylene glycol) has been shown to extent in vivo half-life, but potential side-effects of pegylated pharmaceutical products such as inteferon-beta and ribavirin has been reported (J Clin Gastroenterol. 2004 September; 38(8):717-22, *Gut* 2006; 55:1350-1359 doi:10.1136/gut.2005.076646).

Thus, there still exists a need for improved and safe analogues of GIP, which are stable in formulation and have long in vivo half-life, resulting from decreased susceptibility to proteolysis and decreased clearance, while maintaining binding affinity to a GIP receptor to elicit agonistic effects.

SUMMARY OF THE INVENTION

The present invention concerns GIP analogues which may have the property of an altered GIP activity, as assessed in in vitro efficacy assays and an altered, preferably increased terminal elimination half-life (T½), as assessed in in vivo studies in mice.

It has been found that GIP receptor agonists of the present invention are superior to existing GIP analogues because the GIP agonists offer long terminal half-lifes. The GIP analogues may thus be used as therapeutics for metabolic disorders including, but not limited to, type 2 diabetes mellitus, obesity and related disorders.

The invention provides in a first aspect a GIP analogue represented by the general Formula I:

(SEQ ID NOs: 42 & 86)
R¹-Tyr-X2-Glu-Gly-Thr-Phe-Ile-Ser-Asp-X10-

X11-X12-Glu-Leu-X15-X16-X17-X18-X19-X20-X21-

Phe-X23-X24-X25-Leu-X27-X28-X29-Y1-Y2-R²
(I)

wherein
R¹ is H—, Ac or pGlu pyroglutamic acid (pGlu; (S)-(–)-2-pyrrolidone-5-carboxylic acid), $C_{1-4}$ alkyl, acetyl, formyl, benzoyl and trifluoroacetyl,
X2 is Aib, Ala, D-Ala, Gly, Ser, N-Me-Ser, Ac3c, Ac4c or Ac5c;
X10 is Tyr, Leu or Ser;
X11 is Ser or Leu;
X12 is Lys, ψ or Ile;
X15 is Asp or Glu;
X16 is Ser, Glu, Lys or ψ;
X17 is Ile, Lys, Gln, Arg or ψ;
X18 is His, Arg or Ala;
X19 is Gln, Lys, Ala or Glu;
X20 is Gln, Lys, Ala, His or Arg;
X21 is Ala, Leu, Asp or Glu;
X23 is Val or Ile;
X24 is Asn or Glu;
X25 is Tyr or Trp;
X27 is Leu, Glu, Ser, Lys or Val;
X28 is Ala, Ser or Arg;
X29 is Aib, Gly, Ala, Gln, Thr, Ser or Lys or is absent;
Y1 is Lys-Gly, Gly-Pro-Ser-Ser-Gly-Ala-Pro-Pro-Pro-Ser (SEQ ID NO: 43), Gly-Pro-Ser-Ser-Gly-Ala-Pro-Pro-Ser (SEQ ID NO: 44), Pro-Ser-Ser-Gly-Ala-Pro-Pro-Pro-Ser (SEQ ID NO: 45), Pro-Ser-Ser-Gly-Ala-Pro-Pro-Ser (SEQ ID NO: 46), Gly-Lys-Lys-Asn-Asp-Trp-Lys-His-Asn-Ile-Thr-Gln (SEQ ID NO: 47) or absent;
Y2 is ψ or is absent;
R² is —NH₂ or —OH;
wherein ψ is a residue independently selected from Lys, Arg, Orn and Cys and wherein the side chain of said residue is conjugated to a lipophilic substituent;
and wherein the GIP analogue contains one and only one residue ψ;
or a pharmaceutically acceptable salt or solvate thereof.

In one aspect, R¹ is H—, Ac or pGlu.

Combinations of residues which may be present at some of the variable positions of Formula I include:
Aib2, Asp15, Lys20;
Aib2, Asp15, Arg20;
Aib2, Asp15, Arg20, Ile23;
Aib2, Ile12, Asp15, Arg20, Ile23, Glu24;
Ile12, Asp15, Ile23;
Ile12, Asp15, Ile23, Glu24;
Ile12, Asp15, Ala21, Ile23;
Aib2, Ala21, Ile23, Glu24;
Aib2, Asp15, Ile23;
Aib2, Asp15, Arg20, Ile23, Gln29;
Aib2, Asp15, Arg20, Gly29;
Aib2, Asp15, Ile17, Arg20, Gly29;
Aib2, Asp15, Ile17, Lys20, Gly29;
DAla2, Asp15, Ile23;
DAla2, Asp15, Ile23, Ala28;
Aib2, Asp15, Ile17, Lys20, Ala28;
Asp15, Ile23, Glu24;
N-Me-Ser2, Asp15, Lys20;
N-Me-Ser2, Asp15, Arg20;
N-Me-Ser2, Asp15, Arg20, Ile23;
N-Me-Ser2, Ile12, Asp15, Arg20, Ile23, Glu24;
N-Me-Ser2, Ala21, Ile23, Glu24;
N-Me-Ser2, Asp15, Ile23;
N-Me-Ser2, Asp15, Arg20, Ile23, Gln29;
N-Me-Ser2, Asp15, Arg20, Gly29;
N-Me-Ser2, Asp15, Ile17, Arg20, Gly29;
N-Me-Ser2, Asp15, Ile17, Lys20, Gly29;
N-Me-Ser2, Asp15, Ile23;
N-Me-Ser2, Asp15, Ile23, Ala28;
Ac3c2, Asp15, Lys20;
Ac3c2, Asp15, Arg20;
Ac3c2, Asp15, Arg20, Ile23;
Ac3c2, Ile12, Asp15, Arg20, Ile23, Glu24;
Ac3c2, Ala21, Ile23, Glu24;
Ac3c2, Asp15, Ile23;
Ac3c2, Asp15, Arg20, Ile23, Gln29;
Ac3c2, Asp15, Arg20, Gly29;
Ac3c2, Asp15, Ile17, Arg20, Gly29;
Ac3c2, Asp15, Ile17, Lys20, Gly29;
Ac3c2, Asp15, Ile23;
Ac3c2, Asp15, Ile23, Ala28;
Ac4c2, Asp15, Lys20;
Ac4c2, Asp15, Arg20;
Ac4c2, Asp15, Arg20, Ile23;
Ac4c2, Ile12, Asp15, Arg20, Ile23, Glu24;
Ac4c2, Ala21, Ile23, Glu24;
Ac4c2, Asp15, Ile23;

Ac4c2, Asp15, Arg20, Ile23, Gln29;
Ac4c2, Asp15, Arg20, Gly29;
Ac4c2, Asp15, Ile17, Arg20, Gly29;
Ac4c2, Asp15, Ile17, Lys20, Gly29;
Ac4c2, Asp15, Ile23;
Ac4c2, Asp15, Ile23, Ala28;
Ac5c2, Asp15, Lys20;
Ac5c2, Asp15, Arg20;
Ac5c2, Asp15, Arg20, Ile23;
Ac5c2, Ile12, Asp15, Arg20, Ile23, Glu24;
Ac5c2, Ala21, Ile23, Glu24;
Ac5c2, Asp15, Ile23;
Ac5c2, Asp15, Arg20, Ile23, Gln29;
Ac5c2, Asp15, Arg20, Gly29;
Ac5c2, Asp15, Ile17, Arg20, Gly29;
Ac5c2, Asp15, Ile17, Lys20, Gly29;
Ac5c2, Asp15, Ile23; or
Ac5c2, Asp15, Ile23, Ala28.

The invention provides in a further aspect a GIP analogue represented by the general Formula II:

(SEQ ID NOs: 48 & 87)
R¹-Tyr-X2-Glu-Gly-Thr-Phe-Ile-Ser-Asp-Tyr-

Ser-X12-Glu-Leu-X15-X16-X17-X18-X19-X20-X21-

Phe-X23-X24-X25-Leu-X27-X28-X29-Y1-Y2-R²
(II)

wherein
R¹ is H—, Ac or pGlu;
X2 is Aib, Ala, D-Ala or Gly;
X12 is Lys, ψ or Ile;
X15 is Asp or Glu;
X16 is Ser, Glu, Lys or ψ
X17 is Ile, Lys, Gln, Arg or ψ
X18 is His, Arg or Ala;
X19 is Gln or Ala;
X20 is Gln, Lys, Ala, His or Arg;
X21 is Ala, Asp or Glu;
X23 is Ile or Val;
X24 is Asn or Glu;
X25 is Tyr or Trp;
X27 is Leu, Glu, Ser, Lys or Val;
X28 is Ala, Ser or Arg;
X29 is Aib, Gly, Ala, Gln, Thr, Ser or Lys or is absent;
Y1 is Lys-Gly, Gly-Pro-Ser-Ser-Gly-Ala-Pro-Pro-Pro-Ser (SEQ ID NO: 43), Gly-Pro-Ser-Ser-Gly-Ala-Pro-Pro-Ser (SEQ ID NO: 44), Pro-Ser-Ser-Gly-Ala-Pro-Pro-Pro-Ser (SEQ ID NO: 45), Pro-Ser-Ser-Gly-Ala-Pro-Pro-Ser (SEQ ID NO: 46), Gly-Lys-Lys-Asn-Asp-Trp-Lys-His-Asn-Ile-Thr-Gln (SEQ ID NO: 47) or absent;
Y2 is ψ or is absent;
R² is —NH₂ or —OH;
wherein ψ is a Lys residue wherein the side chain of said Lys residue is conjugated to a lipophilic substituent;
and wherein the GIP analogue contains one and only one residue ψ;
or a pharmaceutically acceptable salt or solvate thereof.

Combinations of residues which may be present at some of the variable positions of Formula II include:
Aib2, Lys12, Asp15, Lys20;
Aib2, Lys12, Asp15, Arg20;
Aib2, Asp15, Arg20;
Aib2, Ile12, Asp15, Arg20, Glu24;
Ile12, Asp15, Ile23;
Ile12, Asp15, Glu24;
Ile12, Asp15, Ala21;
Aib2, Lys12, Ala21, Glu24;
Aib2, Lys12, Asp15;
Aib2, Lys, 12, Asp15, Arg20, Gln29;
Aib2, Lys, 12, Asp15, Arg20, Gly29;
Aib2, Lys12, Asp15, Ile17, Arg20, Gly29;
Aib2, Asp15, Ile17, Lys20, Gly29;
DAla2, Asp15;
DAla2, Asp15, Ala28;
Aib2, Asp15, Ile17, Lys20, Ala28;
Asp15, Glu24;
Ala2, Lys12, Asp15, Lys20;
Ala2, Lys12, Asp15, Arg20;
Ala2, Asp15, Arg20;
Ala2, Ile12, Asp15, Arg20, Glu24;
Ala2, Ile12, Asp15, Ile23;
Ala2, Ile12, Asp15, Glu24;
Ala2, Ile12, Asp15, Ala21;
Ala2, Lys12, Ala21, Glu24;
Ala2, Lys12, Asp15;
Ala2, Lys12, Asp15, Arg20, Gln29;
Ala2, Lys12, Asp15, Arg20, Gly29;
Ala2, Lys12, Asp15, Ile17, Arg20, Gly29;
Ala2, Asp15, Ile17, Lys20, Gly29;
Ala2, Asp15;
Ala2, Asp15, Ala28;
Ala2, Asp15, Ile17, Lys20, Ala28;
Gly2, Lys12, Asp15, Lys20;
Gly2, Lys12, Asp15, Arg20;
Gly2, Asp15, Arg20;
Gly2, Ile12, Asp15, Arg20, Glu24;
Gly2, Ile12, Asp15, Ile23;
Gly2, Ile12, Asp15, Glu24;
Gly2, Ile12, Asp15, Ala21;
Gly2, Lys12, Ala21, Glu24;
Gly2, Lys12, Asp15;
Gly2, Lys12, Asp15, Arg20, Gln29;
Gly2, Lys12, Asp15, Arg20, Gly29;
Gly2, Lys12, Asp15, Ile17, Arg20, Gly29;
Gly2, Asp15, Ile17, Lys20, Gly29;
Gly2, Asp15;
Gly2, Asp15, Ala28;
Gly2, Asp15, Ile17, Lys20, Ala28; or
Gly2, Asp15, Glu24.

The invention provides in a further aspect a GIP analogue represented by the general Formula III:

(SEQ ID NOs: 50 & 88)
R¹-Tyr-Aib-Glu-Gly-Thr-Phe-Ile-Ser-Asp-Tyr-

Ser-Ile-Glu-Leu-X15-X16-X17-X18-X19-X20-X21-

Phe-Val-X24-X25-Leu-Leu-Ala-X29-Y1-Y2-R²
(III)

wherein
R¹ is H—, Ac or pGlu;
X15 is Asp or Glu;
X16 is Lys or ψ;
X17 is Ile or ψ;
X18 is His or Ala;
X19 is Gln or Ala;
X20 is Gln, Lys or Arg;
X21 is Ala, Asp or Glu;
X24 is Asn or Glu;
X25 is Tyr or Trp;

X28 is Ala, Ser or Arg;
X29 is Gln or is absent;
Y1 is Lys-Gly, Gly-Pro-Ser-Ser-Gly-Ala-Pro-Pro-Pro-Ser (SEQ ID NO: 43), Gly-Pro-Ser-Ser-Gly-Ala-Pro-Pro-Ser (SEQ ID NO: 44), Pro-Ser-Ser-Gly-Ala-Pro-Pro-Pro-Ser (SEQ ID NO: 45), Pro-Ser-Ser-Gly-Ala-Pro-Pro-Ser (SEQ ID NO: 46), Gly-Lys-Lys-Asn-Asp-Trp-Lys-His-Asn-Ile-Thr-Gln (SEQ ID NO: 47) or absent;
Y2 is ψ or is absent;
$R^2$ is —NH$_2$ or —OH;
wherein ψ is a residue independently selected from Lys, Arg, Orn and Cys and wherein the side chain of said residue is conjugated to a lipophilic substituent;
and wherein the GIP analogue contains one and only one residue ψ;
or a pharmaceutically acceptable salt or solvate thereof.

Combinations of residues which may be present at some of the variable positions of Formula III include:
Asp15, Lys20;
Asp15, Arg20;
Asp15, Arg20, Glu24;
Asp15, Lys 16;
Asp15, Lys 16, Glu24;
Asp15, ψ16, Ala21;
Ala21, Glu24;
Asp15, Arg20, Gln29;
Asp15, Arg20, Gly29;
Asp15, Ile17, Arg20, Gly29;
Asp15, Ile17, Lys20, Gly29;
Asp15Ala28;
Asp15, Ile17, Lys20, Ala28;
Asp15, Ile23, Glu24;
Asp15, ψ17, Lys20;
Asp15, ψ17, Arg20;
Asp15, ψ17, Arg20;
Asp15, ψ17, Arg20, Glu24;
Asp15, Lys16, ψ17;
Asp15, Lys16, ψ17, Glu24;
Asp15, ψ17, Ala21;
Ala21, ψ17, Glu24;
Asp15, Asp15, ψ17, Arg20, Gln29;
Asp15, ψ17, Arg20, Gly29;
Asp15, Ile17, Arg20, Gly29;
Asp15, Ile17, Lys20, Gly29;
Asp15; ψ17;
Asp15, ψ17, Ala28;
Asp15, Ile17, Lys20, Ala28; or
Asp15, ψ17, Ile23, Glu24.

The GIP-analogue may have the formula R1-Z—R2 where R1 and R2 are as defined above and Z has the sequence:

```
                                              (SEQ ID NO: 51)
Y-Aib-EGTFISDYSIELDKΨHQQDFVNWLLAQGPSSGAPPPS;

(SEQ ID NO: 52)
Y-Aib-EGTFISDYSIELDΨIHQQDFVNWLLAQGPSSGAPPPS;

(SEQ ID NO: 53)
Y-Aib-EGTFISDYSIELEKΨHQQDFVNWLLAQGPSSGAPPPS;

(SEQ ID NO: 54)
Y-Aib-EGTFISDYSIELDKIHQQDFVNWLLAQGPSSGAPPPSΨ;

Y-Aib-EGTFISDYSIELDKIHQQDFVNWLLAQGPSSGAPPPSΨ

(SEQ ID NO: 55)
Y-Aib-EGTFISDYSIELDKIHQQDFVNWLLAQΨ;

(SEQ ID NO: 56)
Y-Aib-EGTFISDYSIELDKIHQQDFVNWLLAQKGΨ;

(SEQ ID NO: 57)
Y-Aib-EGTFISDYSIELDKΨHQQDFVNYLLAQGPSSGAPPPS;

(SEQ ID NO: 58)
Y-Aib-EGTFISDYSIELDKΨHQQDFVNWLLAQGPSSGAPPPS;

(SEQ ID NO: 59)
Y-Aib-EGTFISDYSIELDKΨAAQDFVNWLLAQGPSSGAPPPS;

(SEQ ID NO: 60)
Y-Aib-EGTFISDYSIELEKΨAAKEFVNWLLAQGPSSGAPPPS;

(SEQ ID NO: 61)
Y-Aib-EGTFISDYSIELEKΨAQRAFVEWLLAQGPSSGAPPPS;

(SEQ ID NO: 62)
Y-Aib-EGTFISDYSIELEKIAQRAFVEWLLAQGPSSGAPPPSΨ;

(SEQ ID NO: 63)
Y-Aib-EGTFISDYSIELEKIAQRAFVEWLLAQΨ;

(SEQ ID NO: 64)
Y-Aib-EGTFISDYSIELDKΨAAQDFVNWLLAGPSSGAPPPS;

(SEQ ID NO: 65)
Y-Aib-EGTFISDYSIELDKIAAQDFVNWLLAGPSSGAPPPSΨ;

(SEQ ID NO: 66)
Y-Aib-EGTFISDYSIELDKΨPAQRAFVEWLLAQGPSSGAPPPS;

(SEQ ID NO: 67)
Y-Aib-EGTFISDYSIELDKΨPAQRAFIEWLLAQGPSSGAPPPS;

(SEQ ID NO: 68)
Y-Aib-EGTFISDYSIELDKIAQRAFIEWLLAGPSSGAPPPSKΨ;

(SEQ ID NO: 69)
Y-Aib-EGTFISDYSIELDKIAQKEFIEWLLAGPSSGAPPPSKΨ;

(SEQ ID NO: 70)
Y-Aib-EGTFISDYSIELDKIAAQDFIEWLLAGPSSGAPPPSKΨ;

(SEQ ID NO: 71)
Y-Aib-EGTFISDYSIELDKIAAQDFVEWLLAGPSSGAPPPSKΨ;

(SEQ ID NO: 72)
Y-Aib-EGTFISDYSIELDKIAQRAFIEWLLAQGPSSGAPPPSKΨ;

(SEQ ID NO: 73)
Y-Aib-EGTFISDYSIELDKΨAAQAFVNWLLAGPSSGAPPPS;

(SEQ ID NO: 74)
Y-Aib-EGTFISDYSIELDKΨAAQDFVNWLLAAGPSSGAPPPS;

(SEQ ID NO: 75)
Y-Aib-EGTFISDYSIELDKΨAAQDFINWLLAGPSSGAPPPS;

(SEQ ID NO: 76)
Y-Aib-EGTFISDYSIELDKΨAAQDFIEWLLAGPSSGAPPPS;

(SEQ ID NO: 77)
Y-Aib-EGTFISDYSIELDKΨAAQDFIEWLLAGPSSGAPPPS;

(SEQ ID NO: 78)
Y-Aib-EGTFISDYSIELDKΨIAQRAFIEWLLAQGPSSGAPPPS;

(SEQ ID NO: 79)
Y-Aib-EGTFISDYSΨELDKIAQRAFIEWLLAQGPSSGAPPPS;

(SEQ ID NO: 80)
Y-DAlA-EGTFISDYSIELDKΨAQRAFIEWLLAQGPSSGAPPPS;

(SEQ ID NO: 81)
Y-DAlA-EGTFISDYSIELDKIAAQDFIEWLLAGPSSGAPPPSKΨ;

(SEQ ID NO: 82)
Y-Aib-EGTFISDYSIELDKΨAAQDFIEWLLAQGPSSGAPPPS;
```

-continued

```
                                               (SEQ ID NO: 83)
Y-Aib-EGTFISDYSIELDKΨAAQDFINWLLAQGPSSGAPPPS;
or (SEQ ID NO: 84)
Y-Aib-EGTFISDYSIELDKΨAAQAFIEWLLAQGPSSGAPPPS.
```

The GIP-analogue may have the formula R1-Z—R2 where R1 and R2 are as defined above and Z has the sequence

```
                                               (SEQ ID NO: 1)
Y-Aib-EGTFISDYSIELDK-K(Hexadecanoyl-isoGlu)-
HQQDFVNWLLAQGPSSGAPPPS;

(SEQ ID NO: 2)
Y-Aib-EGTFISDYSIELD-K(Hexadecanoyl-isoGlu)-
IHQQDFVNWLLAQGPSSGAPPPS;

(SEQ ID NO: 3)
Y-Aib-EGTFISDYSIELEK-K(Hexadecanoyl-isoGlu)-
HQQDFVNWLLAQGPSSGAPPPS;

(SEQ ID NO: 4)
Y-Aib-EGTFISDYSIELDKIHQQDFVNWLLAQGPSSGAPPPS-
K([19-carboxy-nonadecanoyl]-isoGlu-Peg3-Peg3);

(SEQ ID NO: 5)
Y-Aib-EGTFISDYSIELDKIHQQDFVNWLLAQGPSSGAPPPS-
K(Hexadecanoyl-isoGlu);

(SEQ ID NO: 6)
Y-Aib-EGTFISDYSIELDKIHQQDFVNWLLAQ-K
(Hexadecanoyl-isoGlu);

(SEQ ID NO: 7)
Y-Aib-EGTFISDYSIELDKIHQQDFVNWLLAQKG-
K(Hexadecanoyl-isoGlu);

(SEQ ID NO: 8)
Y-Aib-EGTFISDYSIELDK-K([19-carboxy-nonadecanoyl]-
isoGlu-Peg3-Peg3)-HQQDFVNYLLAQGPSSGAPPPS;

(SEQ ID NO: 9)
Y-Aib-EGTFISDYSIELDK-K([19-carboxy-nonadecanoyl]-
isoGlu-Peg3-Peg3)-HQQDFVNWLLAQGPSSGAPPPS;

(SEQ ID NO: 10)
Y-Aib-EGTFISDYSIELDK-K([19-carboxy-nonadecanoyl]-
isoGlu-Peg3-Peg3)-AAQDFVNWLLAQGPSSGAPPPS;

(SEQ ID NO: 11)
Y-Aib-EGTFISDYSIELEK-K([19-carboxy-nonadecanoyl]-
isoGlu-Peg3-Peg3)-AAKEFVNWLLAQGPSSGAPPPS;

(SEQ ID NO: 12)
Y-Aib-EGTFISDYSIELEK-K([19-carboxy-nonadecanoyl]-
isoGlu-Peg3-Peg3)-AQRAFVEWLLAQGPSSGAPPPS;

(SEQ ID NO: 13)
Y-Aib-EGTFISDYSIELEKIAQRAFVEWLLAQGPSSGAPPPS-
K([19-carboxy-nonadecanoyl]-isoGlu-Peg3-Peg3);

(SEQ ID NO: 14)
Y-Aib-EGTFISDYSIELEKIAQRAFVEWLLAQ-K([19-carboxy-
nonadecanoyl]-isoGlu-Peg3-Peg3);

(SEQ ID NO: 15)
H-Y-Aib-EGTFISDYSIELDK-K([19-carboxy-nonadecanoyl]-
isoGlu-Peg3-Peg3)-AAQDFVNWLLAGPSSGAPPPS;

(SEQ ID NO: 16)
Y-Aib-EGTFISDYSIELDKIAAQDFVNWLLAGPSSGAPPPS-
K([19-carboxy-nonadecanoyl]-isoGlu-Peg3-Peg3);

(SEQ ID NO: 17)
Y-Aib-EGTFISDYSIELDK-K([19-Carboxy-nonadecanoyl]-
isoGlu-Peg3-Peg3)-AQRAFVEWLLAQGPSSGAPPPS;

(SEQ ID NO: 18)
Y-Aib-EGTFISDYSIELDK-K([19-Carboxy-nonadecanoyl]-
isoGlu-Peg3-Peg3)-AQRAFIEWLLAQGPSSGAPPPS;

(SEQ ID NO: 19)
Y-Aib-EGTFISDYSIELDK-K((19-Carboxy-nonadecanoyl)-
[(Piperazine-1-yl)-acetyl]-Peg3-Peg3)-
AQRAFIEWLLAQGPSSGAPPPS;

(SEQ ID NO: 20)
Y-Aib-EGTFISDYSIELDK-K((19-Carboxy-nonadecanoyl)-
[(Piperazine-1-yl)-acetyl]-Peg3-Peg3)-
AQRAFVEWLLAQGPSSGAPPPS;

(SEQ ID NO: 21)
Y-Aib-EGTFISDYSIELDK-K((19-Carboxy-nonadecanoyl)-
[(Piperazine-1-yl)-acetyl]-Peg3-Peg3)-
AQKEFVEWLLAAGPSSGAPPPS;

(SEQ ID NO: 22)
Y-Aib-EGTFISDYSIELDK-K([19-Carboxy-nonadecanoyl]-
isoGlu-Peg3-Peg3)-AQKEFVEWLLAAGPSSGAPPPS;

(SEQ ID NO: 23)
Y-Aib-EGTFISDYSIELDKIAQRAFIEWLLAGPSSGAPPPS-
K([19-Carboxy-nonadecanoyl]-isoGlu-Peg3-Peg3);

(SEQ ID NO: 24)
Y-Aib-EGTFISDYSIELDKIAQKEFIEWLLAGPSSGAPPPS-
K([19-Carboxy-nonadecanoyl]-isoGlu-Peg3-Peg3);

(SEQ ID NO: 25)
Y-Aib-EGTFISDYSIELDKIAAQDFIEWLLAGPSSGAPPPS-
K([19-Carboxy-nonadecanoyl]-isoGlu-Peg3-Peg3);

(SEQ ID NO: 26)
Y-Aib-EGTFISDYSIELDKIAAQDFIEWLLAGPSSGAPPPS-
K((19-Carboxy-nonadecanoyl)-[(Piperazine-1-yl)-
acetyl]-Peg3-Peg3);

(SEQ ID NO: 27)
Y-Aib-EGTFISDYSIELDKIAAQDFVEWLLAGPSSGAPPPS-
K([19-Carboxy-nonadecanoyl]-isoGlu-Peg3-Peg3);
```

-continued

```
                                        (SEQ ID NO: 28)
Y-Aib-EGTFISDYSIELDKIAQRAFIEWLLAQGPSSGAPPPS-
K([19-Carboxy-nonadecanoyl]-isoGlu-Peg3-Peg3);

(SEQ ID NO: 29)
Y-Aib-EGTFISDYSIELDK-K([19-Carboxy-nonadecanoyl]-
isoGlu-Peg3-Peg3)-AAQAFVNWLLAGPSSGAPPPS;

(SEQ ID NO: 30)
Y-Aib-EGTFISDYSIELDK-K([19-Carboxy-nonadecanoyl]-
isoGlu-Peg3-Peg3)-AAQDFVNWLLAAGPSSGAPPPS;

(SEQ ID NO: 31)
Y-Aib-EGTFISDYSIELDK-K([19-Carboxy-nonadecanoyl]-
isoGlu-Peg3-Peg3)-AAQDFINWLLAGPSSGAPPPS;

(SEQ ID NO: 32)
Y-Aib-EGTFISDYSIELDK-K([19-Carboxy-nonadecanoyl]-
isoGlu-Peg3-Peg3)-AAQDFIEWLLAGPSSGAPPPS;

(SEQ ID NO: 33)
Y-Aib-EGTFISDYSIELDK-K((19-Carboxy-nonadecanoyl)-
[(Piperazine-1-yl)-acetyl]-Peg3-Peg3)-
AAQDFIEWLLAGPSSGAPPPS;

(SEQ ID NO: 34)
Y-Aib-EGTFISDYSIELD-K([19-Carboxy-nonadecanoyl]-
isoGlu-Peg3-Peg3)-IAQRAFIEWLLAQGPSSGAPPPS;

(SEQ ID NO: 35)
Y-Aib-EGTFISDYS-K([19-Carboxy-nonadecanoyl]-
isoGlu-Peg3-Peg3)-ELDKIAQRAFIEWLLAQGPSSGAPPPS;

(SEQ ID NO: 36)
Y-DAla-EGTFISDYSIELDK-K([19-Carboxy-nonadecanoyl]-
isoGlu-Peg3-Peg3)-AQRAFIEWLLAQGPSSGAPPPS;

(SEQ ID NO: 37)
Y-DAla-EGTFISDYSIELDKIAAQDFIEWLLAGPSSGAPPPS-
K((19-Carboxy-nonadecanoyl)-[(Piperazine-1-yl)
-acetyl]-Peg3-Peg3);

(SEQ ID NO: 38)
Y-Aib-EGTFISDYSIELDK-K([19-Carboxy-nonadecanoyl]-
isoGlu-Peg3-Peg3)-AAQDFIEWLLAQGPSSGAPPPS;

(SEQ ID NO: 39)
Y-Aib-EGTFISDYSIELDK-K([19-Carboxy-nonadecanoyl]-
isoGlu-Peg3-Peg3)-AAQDFINWLLAQGPSSGAPPPS;

(SEQ ID NO: 40)
Y-Aib-EGTFISDYSIELDK-K([19-Carboxy-nonadecanoyl]-
isoGlu-Peg3-Peg3)-AAQAFIEWLLAQGPSSGAPPPS;
or (SEQ ID NO: 41)
Y-Aib-EGTFISDYSIELDK-K((19-Carboxy-nonadecanoyl)-
[(Piperazine-1-yl)-acetyl]-Peg3-Peg3)-
AAQAFIEWLLAQGPSSGAPPPS.
```

The GIP-analogue may be

```
                                        (SEQ ID NO: 1)
H-Y-Aib-EGTFISDYSIELDK-K(Hexadecanoyl-isoGlu)-
HQQDFVNWLLAQGPSSGAPPPS-NH₂;
(Compound 1)

(SEQ ID NO: 2)
H-Y-Aib-EGTFISDYSIELD-K(Hexadecanoyl-isoGlu)-
IHQQDFVNWLLAQGPSSGAPPPS-NH₂;
(Compound 2)

(SEQ ID NO: 3)
H-Y-Aib-EGTFISDYSIELEK-K(Hexadecanoyl-isoGlu)-
HQQDFVNWLLAQGPSSGAPPPS-NH₂;
(Compound 3)

(SEQ ID NO: 4)
H-Y-Aib-EGTFISDYSIELDKIHQQDFVNWLLAQGPSSGAPPPS-
K([19-carboxy-nonadecanoyl]-
isoGlu-Peg3-Peg3)-NH₂ (Compound 4);

(SEQ ID NO: 5)
H-Y-Aib-EGTFISDYSIELDKIHQQDFVNWLLAQGPSSGAPPPS-
K(Hexadecanoyl-isoGlu)-NH₂;
(Compound 5)

(SEQ ID NO: 6)
H-Y-Aib-EGTFISDYSIELDKIHQQDFVNWLLAQ-
K(Hexadecanoyl-isoGlu)-NH₂;
(Compound 6);

(SEQ ID NO: 7)
H-Y-Aib-EGTFISDYSIELDKIHQQDFVNWLLAQKG-
K(Hexadecanoyl-isoGlu)-NH₂;
(Compound 7)

(SEQ ID NO: 8)
H-Y-Aib-EGTFISDYSIELDK-K([19-carboxy-
nonadecanoyl]-isoGlu-Peg3-Peg3)-
HQQDFVNYLLAQGPSSGAPPPS-NH₂;
(Compound 8)

(SEQ ID NO: 9)
H-Y-Aib-EGTFISDYSIELDK-K([19-carboxy-
nonadecanoyl]-isoGlu-Peg3-Peg3)-
HQQDFVNWLLAQGPSSGAPPPS-NH₂;
(Compound 9)

(SEQ ID NO: 10)
H-Y-Aib-EGTFISDYSIELDK-K([19-carboxy-
nonadecanoyl]-isoGlu-Peg3-Peg3)-
AAQDFVNWLLAQGPSSGAPPPS-NH₂;
(Compound 10)

(SEQ ID NO: 11)
H-Y-Aib-EGTFISDYSIELEK-K([19-carboxy-
nonadecanoyl]-isoGlu-Peg3-Peg3)-
AAKEFVNWLLAQGPSSGAPPPS-NH₂;
(Compound 11)
```

-continued (SEQ ID NO: 12)
H-Y-Aib-EGTFISDYSIELEK-K([19-carboxy-nonadecanoyl]-isoGlu-Peg3-Peg3)-AQRAFVEWLLAQGPSSGAPPPS-NH$_2$;
(Compound 12)

(SEQ ID NO: 13)
H-Y-Aib-EGTFISDYSIELEKIAQRAFVEWLLAQGPSSGAPPPS-K([19-carboxy-nonadecanoyl]-isoGlu-Peg3-Peg3)-NH$_2$;
(Compound 13)

(SEQ ID NO: 14)
H-Y-Aib-EGTFISDYSIELEKIAQRAFVEWLLAQ-K([19-carboxy-nonadecanoyl]-isoGlu-Peg3-Peg3)-NH$_2$;
(Compound 14)

(SEQ ID NO: 15)
H-Y-Aib-EGTFISDYSIELDK-K([19-carboxy-nonadecanoyl]-isoGlu-Peg3-Peg3)-AAQDFVNWLLAGPSSGAPPPS-NH$_2$;
(Compound 15)

(SEQ ID NO: 16)
H-Y-Aib-EGTFISDYSIELDKIAAQDFVNWLLAGPSSGAPPPS-K([19-carboxy-nonadecanoyl]-isoGlu-Peg3-Peg3)-NH$_2$;
(Compound 16)

(SEQ ID NO: 17)
H-Y-Aib-EGTFISDYSIELDK-K([19-Carboxy-nonadecanoyl]-isoGlu-Peg3-Peg3)-AQRAFVEWLLAQGPSSGAPPPS-NH$_2$;
(Compound 17)

(SEQ ID NO: 18)
H-Y-Aib-EGTFISDYSIELDK-K([19-Carboxy-nonadecanoyl]-isoGlu-Peg3-Peg3)-AQRAFIEWLLAQGPSSGAPPPS-NH$_2$;
(Compound 18)

(SEQ ID NO: 19)
H-Y-Aib-EGTFISDYSIELDK-K((19-Carboxy-nonadecanoyl)-[(Piperazine-1-yl)-acetyl]-Peg3-Peg3)-AQRAFIEWLLAQGPSSGAPPPS-NH$_2$;
(Compound 19)

(SEQ ID NO: 20)
H-Y-Aib-EGTFISDYSIELDK-K((19-Carboxy-nonadecanoyl)-[(Piperazine-1-yl)-acetyl]-Peg3-Peg3)-AQRAFVEWLLAQGPSSGAPPPS-NH$_2$;
(Compound 20)

(SEQ ID NO: 21)
H-Y-Aib-EGTFISDYSIELDK-K((19-Carboxy-nonadecanoyl)-[(Piperazine-1-yl)-acetyl]-Peg3-Peg3)-AQKEFVEWLLAAGPSSGAPPPS-NH$_2$;
(Compound 21)

(SEQ ID NO: 22)
H-Y-Aib-EGTFISDYSIELDK-K([19-Carboxy-nonadecanoyl]-isoGlu-Peg3-Peg3)-AQKEFVEWLLAAGPSSGAPPPS-NH$_2$;
(Compound 22)

(SEQ ID NO: 23)
H-Y-Aib-EGTFISDYSIELDKIAQRAFIEWLLAGPSSGAPPPS-K([19-Carboxy-nonadecanoyl]-isoGlu-Peg3-Peg3)-NH$_2$;
(Compound 23)

(SEQ ID NO: 24)
H-Y-Aib-EGTFISDYSIELDKIAQKEFIEWLLAGPSSGAPPPS-K([19-Carboxy-nonadecanoyl]-isoGlu-Peg3-Peg3)-NH$_2$;
(Compound 24)

(SEQ ID NO: 25)
H-Y-Aib-EGTFISDYSIELDKIAAQDFIEWLLAGPSSGAPPPS-K([19-Carboxy-nonadecanoyl]-isoGlu-Peg3-Peg3)-NH$_2$;
(Compound 25)

(SEQ ID NO: 26)
H-Y-Aib-EGTFISDYSIELDKIAAQDFIEWLLAGPSSGAPPPS-K((19-Carboxy-nonadecanoyl)-[(Piperazine-1-yl)-acetyl]-Peg3-Peg3)-NH$_2$;
(Compound 26)

(SEQ ID NO: 27)
H-Y-Aib-EGTFISDYSIELDKIAAQDFVEWLLAGPSSGAPPPS-K([19-Carboxy-nonadecanoyl]-isoGlu-Peg3-Peg3)-NH$_2$;
(Compound 27)

(SEQ ID NO: 28)
H-Y-Aib-EGTFISDYSIELDKIAQRAFIEWLLAQGPSSGAPPPS-K([19-Carboxy-nonadecanoyl]-isoGlu-Peg3-Peg3)-NH$_2$;
(Compound 28)

(SEQ ID NO: 29)
H-Y-Aib-EGTFISDYSIELDK-K([19-Carboxy-nonadecanoyl]-isoGlu-Peg3-Peg3)-AAQAFVNWLLAGPSSGAPPPS-NH$_2$;
(Compound 29)

(SEQ ID NO: 30)
H-Y-Aib-EGTFISDYSIELDK-K([19-Carboxy-nonadecanoyl]-isoGlu-Peg3-Peg3)-AAQDFVNWLLAAGPSSGAPPPS-NH$_2$;
(Compound 30)

(SEQ ID NO: 31)
H-Y-Aib-EGTFISDYSIELDK-K([19-Carboxy-nonadecanoyl]-isoGlu-Peg3-Peg3)-AAQDFINWLLAGPSSGAPPPS-NH$_2$;
(Compound 31)

(SEQ ID NO: 32)
H-Y-Aib-EGTFISDYSIELDK-K([19-Carboxy-nonadecanoyl]-isoGlu-Peg3-Peg3)-AAQDFIEWLLAGPSSGAPPPS-NH$_2$;
(Compound 32)

(SEQ ID NO: 33)
H-Y-Aib-EGTFISDYSIELDK-K((19-Carboxy-nonadecanoyl)-[(Piperazine-1-yl)-acetyl]-Peg3-Peg3)-AAQDFIEWLLAGPSSGAPPPS-NH$_2$;
(Compound 33)

(SEQ ID NO: 34)
H-Y-Aib-EGTFISDYSIELD-K([19-Carboxy-nonadecanoyl]-isoGlu-Peg3-Peg3)-IAQRAFIEWLLAQGPSSGAPPPS-NH$_2$;
(Compound 34)

(SEQ ID NO: 35)
H-Y-Aib-EGTFISDYS-K([19-Carboxy-nonadecanoyl]-isoGlu-Peg3-Peg3)-ELDKIAQRAFIEWLLAQGPSSGAPPPS-NH$_2$;;
(Compound 35)

(SEQ ID NO: 36)
H-Y-DAlA-EGTFISDYSIELDK-K([19-Carboxy-nonadecanoyl]-isoGlu-Peg3-Peg3)-AQRAFIEWLLAQGPSSGAPPPS-NH$_2$;
(Compound 36)

(SEQ ID NO: 37)
H-Y-DAlA-EGTFISDYSIELDKIAAQDFIEWLLAGPSSGAPPPS-K((19-Carboxy-nonadecanoyl)-[(Piperazine-1-yl)-acetyl]-Peg3-Peg3)-NH$_2$;
(Compound 37)

(SEQ ID NO: 38)
H-Y-Aib-EGTFISDYSIELDK-K([19-Carboxy-nonadecanoyl]-isoGlu-Peg3-Peg3)-AAQDFIEWLLAQGPSSGAPPPS-NH$_2$;
(Compound 38)

(SEQ ID NO: 39)
H-Y-Aib-EGTFISDYSIELDK-K([19-Carboxy-nonadecanoyl]-isoGlu-Peg3-Peg3)-AAQDFINWLLAQGPSSGAPPPS-NH$_2$;
(Compound 39)

(SEQ ID NO: 40)
H-Y-Aib-EGTFISDYSIELDK-K([19-Carboxy-nonadecanoyl]-isoGlu-Peg3-Peg3)-AAQAFIEWLLAQGPSSGAPPPS-NH$_2$;
(Compound 40)
and
or (SEQ ID NO: 41)
H-Y-Aib-EGTFISDYSIELDK-K((19-Carboxy-nonadecanoyl)-[(Piperazine-1-yl)-acetyl]-Peg3-Peg3)-AAQAFIEWLLAQGPSSGAPPPS-NH$_2$.
(Compound 41)

The invention further provides a pharmaceutical composition comprising a GIP analogue as described herein, or a pharmaceutically acceptable salt or solvate thereof, in admixture with a carrier, preferably a pharmaceutically acceptable carrier. The GIP analogue may, for example, be a pharmaceutically acceptable acid addition salt.

The pharmaceutical composition may be formulated as a liquid suitable for administration by injection or infusion. The pharmaceutical composition may be formulated to cause controlled, e.g., slow release of said GIP analogue.

The invention further provides a therapeutic kit comprising a GIP analogue as described herein, and a device comprising a GIP analogue as described herein.

The invention further provides a GIP analogue as described herein, or a pharmaceutically acceptable salt or solvate thereof, for use in a method of medical treatment, e.g. for use in the treatment and/or prevention of a metabolic disorder.

The invention further provides the use of a GIP analogue as described herein, or a pharmaceutically acceptable salt or solvate thereof, in the preparation of a medicament for the treatment and/or prevention of a metabolic disorder.

The invention further provides a method of prevention and or/treatment of a metabolic disorder in a subject, comprising administering a GIP analogue as described herein, or a pharmaceutically acceptable salt or solvate thereof, to the subject.

The metabolic disorder may be diabetes or a diabetes related disorder, or obesity or an obesity related disorder. The link between obesity and diabetes is well known, so these conditions may be but are not necessarily separate or mutually exclusive.

Diabetes related disorders include insulin resistance, glucose intolerance, increased fasting glucose, pre-diabetes, type 1 diabetes, type 2 diabetes, gestational diabetes hypertension, dyslipidemia, and combinations thereof.

Diabetes related disorders also include atherosclerosis, arteriosclerosis, coronary heart disease, peripheral artery disease and stroke; or conditions associated with atherogenic dyslipidemia, blood fat disorders, elevated blood pressure, hypertension, a prothrombotic state, a proinflammatory state, and bone related disorders such as osteoporosis.

The blood fat disorder may be selected from high triglycerides, low HDL cholesterol, high LDL cholesterol, and plaque buildup in artery walls, or a combination thereof.

The prothrombotic state may be selected from high fibrinogen levels in the blood and high plasminogen activator inhibitor-1 levels in the blood.

The proinflammatory state may be an elevated C-reactive protein level in the blood.

Obesity related disorders include obesity linked inflammation, obesity linked gallbladder disease and obesity induced sleep apnea, or may be associated with a condition selected from atherogenic dyslipidemia, blood fat disorders, elevated blood pressure, hypertension, a prothrombotic state, and a proinflammatory state, or a combination thereof.

BRIEF DESCRIPTION OF THE DRAWINGS

FIGS. 1A-1D: Blood glucose levels (1A-1C) and area under the blood glucose curves (AUC) (1D) in an OGTT in 5-hour fasted mice. The mice were injected s.c. with vehicle, the GLP-1 analogue liraglutide (10 nmol/kg), and GIP receptor agonists (compound 12, 13, 17, and 21 at 3-300 nmol/kg) 4 hours prior to the oral gavage of glucose (t=0). Data are means±SEM; n=6. Statistical differences vs vehicle: *p<0.05, p<0.01, *p<0.001.

FIGS. 2A-2E: Blood glucose levels (2A-2D) and area under the blood glucose curves (AUC) (2E) in an OGTT in 5-hour fasted mice. The mice were injected s.c. with vehicle and GIP receptor agonists (compounds 12, 18, 41, 33, and 35 at 3300 nmol/kg) 4 hours prior to the oral gavage of glucose (t=0). Data are means±SEM; n=6. Statistical differences vs vehicle: ***p<0.001.

FIGS. 4A-4E: Relative body weight changes (delta Δ body weight=body weight at each study day–body weight at day 0) in DIO mice during four weeks of treatment with vehicle, GLP-1 analogue liraglutide, liraglutide+Compound 10 or 12 (FIG. 4A), liraglutide+Compound 17 (FIG. 4B), liraglutide+Compound 18 (FIG. 4C), liraglutide+compound 35 (FIG. 4D) or liraglutide+Compound 41 (FIG. 4E). Animals were treated once daily with two separate s.c. injections. The first injection was with vehicle 1 or liraglutide (20 nmol/kg). The second injection was with vehicle 2 or GIP agonists (30 and/or 300 nmol/kg). The GIP agonists were only dosed every third day of the study (starting on day 0). On other days, GIP agonists were replaced with vehicle 2. Data are means±SEM; n=9. Statistical differences vs vehicle on day 27: ***p<0.001. Statistical differences (p<0.05) between liraglutide and liraglutide co-treated with GIP agonist are shown with lines.

DETAILED DESCRIPTION OF THE INVENTION

Figure 1C:
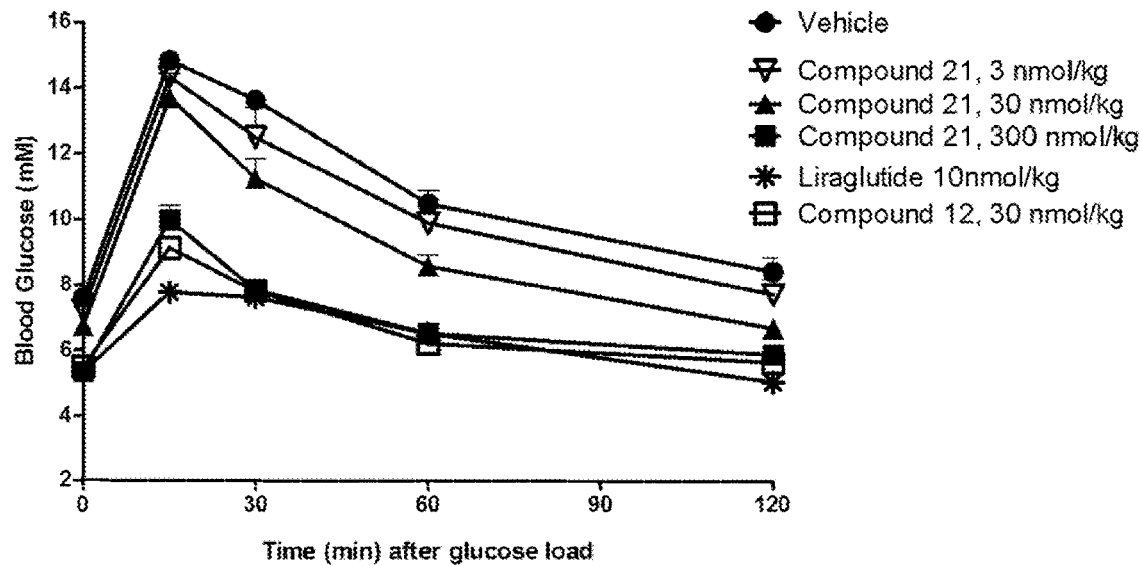

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

Definitions

Unless specified otherwise, the following definitions are provided for specific terms, which are used in the above written description.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "solvate" in the context of the present invention refers to a complex of defined stoichiometry formed between a solute (in casu, a peptide conjugate or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that activates signaling by the receptor type in question. The term "antagonist" as employed in the context of the invention refers to a substance (ligand) that decreases signaling by the receptor type in question.

Throughout the description and claims the conventional one-letter and three-letter codes for natural (or "proteinogenic") amino acids are used, as well as generally accepted three letter codes for other (non-natural or "non-proteinogenic") α-amino acids, such as Aib (α-aminoisobutyric acid), Orn (ornithine) and D-Ala (D-alanine). All amino acid residues in peptides of the invention are preferably of the L-configuration except where explicitly stated.

Among sequences disclosed herein are sequences incorporating an "H—" moiety at the amino terminus (N-terminus) of the sequence, and either an "—OH" moiety or an "—NH$_2$" moiety at the carboxy terminus (C-terminus) of the sequence. In such cases, and unless otherwise indicated, an "H—" moiety at the N-terminus of the sequence in question indicates a hydrogen atom (i.e. $R^1$=H), corresponding to the presence of a free primary or secondary amino group at the N-terminus, while an "—OH" or an "—NH$_2$" moiety at the C-terminus of the sequence (i.e. $R^2$=OH or NH$_2$) indicates a carboxy (COOH) group or an amido (CONH$_2$) group at the C-terminus, respectively.

The compounds of the present invention have GIP biological activity, in particular in treatment of metabolic diseases such as diabetes and obesity. This can be assessed, e.g., in in vivo assays, in which the blood glucose level or another biological activity is determined after a test animal has been treated or exposed to a GIP analogue. The compounds of the present invention may be particular effective in improving glycaemic control and reducing body weight when administered together with a GLP-1 receptor agonist to a diabetic patient and/or an overweight or obese subject. The effect obtained with this combination therapy may be superior to that obtained with the administration of a GLP-1 receptor agonist alone in comparable subjects when given according to a comparable dosing regime. The compounds of the present invention may also be capable of improving glycaemic control and reducing bodyweight when administered alone. The Y1 and Y2 group has a stabilizing effect on the GIP analogues. Without being bound to any theory it is believed that group comprising the C-terminus part of exendin-4 and GIP compounds has impact on the folding of the peptide.

In either the treatment of a diabetic subject or an overweight subject, the effect of treating with a GIP analogue of the present invention may be superior to that obtained with an equivalent quantity (by mass, or molar ratio) of wild type human GIP in comparable subjects when given according to a comparable dosing regime, alone or in combination with another anti-diabetic or anti-obesity agent.

Activity in in vitro assays may also be used as a measure of the compounds' activity. Typically the compounds have activity (i.e. agonist activity) at the GIP receptor (designated GIP-R). $EC_{50}$ values may be used as a numerical measure of agonist potency at a given receptor. An $EC_{50}$ value is a measure of the concentration of a compound required to achieve half of that compound's maximal activity in a particular assay. In any given assay, the $EC_{50}$ value of a compound in a given assay may be assessed relative to the $EC_{50}$ of human GIP. Thus, the ratio of the $EC_{50}$ value of the test compound to the $EC_{50}$ value of wild type human GIP ($EC_{50}$[test compound]/$EC_{50}$[GIP]) at the human GIP receptor may be less than 10, less than 5, less than 1, less than 0.1, less than 0.05 or less than 0.01. $EC_{50}$ values may be determined using the human GIP receptor assay described in the Examples below. In such an assay, the compounds may, for example, have an $EC_{50}$ value of 0.001-0.050 nM, 0.001-0.030 nM, 0.001-0.020 nM, or 0.001-0.010 nM.

The compounds typically have minimal or no agonist activity at the GLP-1 receptor. For example, the ratio of the $EC_{50}$ value of the test compound to the $EC_{50}$ value of the GLP-1 agonist Exendin-4 ($EC_{50}$[test compound]/$EC_{50}$[Ex4]) at the human GIP receptor may be at least about 100, at least about 250, at least about 500, at least about 750, at least about 1000, at least about 5000, or at least about 10,000. ("About" is used here to signify+−10%.) $EC_{50}$ values may be determined using the human GLP-1 receptor assay described in the Examples below. In such an assay, the compounds may, for example, have an $EC_{50}$ value of at least 1 nM, at least 3 nM, at least 5 nM or at least 10 nM.

Lipophilic Group

The compound of the invention comprises a residue ψ, i.e. a residue selected from Lys, Arg, Orn and Cys in which the side chain is conjugated to a lipophilic substituent.

Without wishing to be bound by any particular theory, it is thought that the substituent binds plasma proteins (e.g. albumin) in the blood stream, thus shielding the compounds of the invention from enzymatic degradation and thereby enhancing the half-life of the compounds. It may also modulate the potency of the compound, e.g. with respect to the GIP receptor.

The substituent is conjugated to the functional group at the distal end of the side chain from the alpha-carbon. The normal ability of the Lys, Arg, Orn or Cys side chain to participate in interactions mediated by that functional group (e.g. intra- and inter-molecular interactions) may therefore be reduced or completely eliminated by the presence of the substituent. Thus, the overall properties of the compound may be relatively insensitive to changes in the actual amino acid present as residue ψ. Consequently, it is believed that any of the residues Lys, Arg, Orn and Cys may be present at any position where ψ is permitted. However, in certain embodiments, it may be advantageous that the amino acid component of ψ is Lys.

Thus, ψ is a residue of Lys, Arg, Orn or Cys in which the side chain is conjugated to a substituent having the formula —$Z^1$ or —$Z^2$—$Z^1$.

—$Z^1$ is a fatty chain having at a terminus a connection —X— to ψ or to $Z^2$;
wherein
—X— is a bond, —CO—, —SO—, or —$SO_2$—;
and, optionally, $Z^1$ has a polar group at the end of the chain distal from connection —X—; said polar group comprising a carboxylic acid or a carboxylic acid bioisostere, a phosphonic acid, or a sulfonic acid group;
and wherein —$Z^2$—, if present, is a spacer of formula:

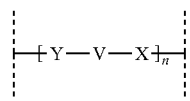

connecting $Z^1$ to ψ;
wherein:
each Y is independently —NH, —NR, —S or —O, where R is alkyl, a protecting group or forms a linkage to another part of the spacer $Z^2$;
each X is independently a bond, CO—, SO—, or $SO_2$—;
with the proviso that when Y is —S, the X to which it is bound is a bond;
each V is independently a bivalent organic moiety linking Y and X;
and n is 1-10.

The group $Z^1$ $Z^1$ is a fatty chain having a connection to ψ or to $Z^2$, referred to herein as —X—. —X— may be, for example, a bond, acyl (—CO—), sulfinyl (—SO—), or sulfonyl (—$SO_2$—). When $Z^1$ is bound directly to ψ, that is, when $Z^2$ is not present, preferably —X— is acyl (—CO—), sulfinyl (—SO—), or sulfonyl (—$SO_2$—). Most preferably, —X— is acyl (—CO—).

$Z^1$ may further have a polar group, said polar group being located at the end of the chain distal from the connection —X—. In other words, the connection is located at the ω-position with respect to the polar group. The polar group may be bound directly to the terminus of the fatty chain, or may be bound via a linker.

Preferably, the polar group is an acidic or weakly acid group, for example a carboxylic acid or a carboxylic acid bioisostere, a phosphonate, or a sulfonate. The polar group may have a $pK_a$ of between −2 and 12 in water, more preferably between 1 and 7, more preferably between 3 and 6. Certain preferred polar groups have a $pK_a$ of between 4 and 5.

For example, and not by way of limitation, the polar group may comprise a carboxylic acid (—COOH) or a carboxylic acid bioisostere, a phosphonic acid (—P(O)(OH)$_2$), or a sulfonic acid (—$SO_2OH$) group.

Preferably the polar group, if present, comprises a carboxylic acid or carboxylic acid bioisostere. Suitable carboxylic acid bioisosteres are known in the art. Preferably the bioisostere has a proton having a $pK_a$ similar to the corresponding carboxylic acid. Examples of suitable bioisoteres may include, not by way of limitation, tetrazole, acylsulfomides, acylhydroxylarmne, and squaric acid derivatives, as shown below ( - - - indicates the point of attachment):

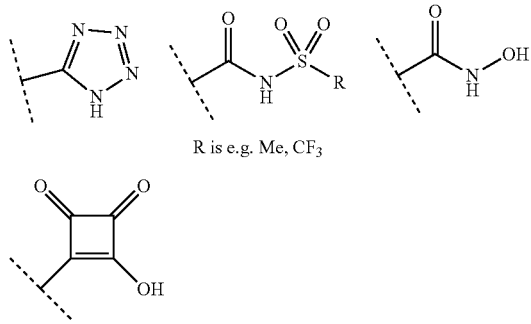

R is e.g. Me, CF$_3$

Fatty chain as used herein refers to a moiety comprising a chain of carbon atoms, the carbon atoms being predominantly substituted with hydrogen or hydrogen-like atoms, for example, a hydrocarbon chain. Such fatty chains are often referred to as lipophilic, although it will be appreciated that substitution may alter the lipophilic properties of the overall molecule.

The fatty chain may by aliphatic. It may be entirely saturated or may include one or more double or triple bonds. Each double bond, if present, may be in the E or Z configuration. The fatty chain may also have one or more cycloalkylene or heterocycloalkylene moieties in its length, and additionally or alternatively may have one or more arylene or heteroarylene moieties in its length. For example, the fatty chain may incorporate a phenylene or piperazinylene moiety in its length as, for example, shown below (wherein - - - represents the points of attachment within the chain).

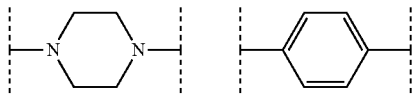

The fatty chain may be derived from a fatty acid, for example, it may be derived from a medium-chain fatty acid (MCFA) with an aliphatic tail of 6-12 carbon atoms, a long-chain fatty acid (LCFA) with an aliphatic tail of 13-21 carbon atoms, or a very long-chain fatty acid (LCFA) with an aliphatic tail of 22 carbon atoms or more. Examples of linear saturated fatty acids from which suitable fatty chains may be derived include tridecylic (tridecanoic) acid, myristic (tetradecanoic) acid, pentadecylic (pentadecanoic) acid, palmitic (hexadecanoic) acid, and margaric (heptadecanoic) acid. Examples of linear unsaturated fatty acids from which suitable fatty chains may be derived include myristoleic acid, palmitoleic acid, sapienic acid and oleic acid.

The fatty chain may be connected to ψ or to $Z^2$ by an amide linkage, a sulfinamide linkage, a sulfonamide linkage, or by an ester linkage, or by an ether, thioether or amine linkage. Accordingly, the fatty chain may have, a bond to ψ or to $Z^2$ or an acyl (—CO—), sulfinyl (—SO—), or sulfonyl (—SO$_2$—) group. Preferably, the fatty chain has a terminus having an acyl (—CO—) group and is connected to ψ or $Z^2$ by an amide or ester linkage.

In some embodiments, $Z^1$ is a group of formula:

A-B-Alk-X— wherein
A is hydrogen or a carboxylic acid, a carboxylic acid bioisostere, a phosphonic acid, or a sulfonic acid group;
B is a bond or a linker;
X is a bond, acyl (—CO—), sulfinyl (—SO—), or sulfonyl (—SO$_2$—); and
Alk is a fatty chain that may be optionally substituted with one or more substituents. The fatty chain is preferably 6 to 28 carbon atoms in length (e.g. a C$_{6-28}$alkylene), more preferably, 12 to 26 carbons in length (e.g. a C$_{12-26}$alkylene), more preferably, 16 to 22 carbons in length (e.g. C$_{16-22}$alkylene), and may be saturated or unsaturated. Preferably, Alk is saturated, that is, preferably Alk is alkylene.

Optional substituents on the fatty chain may be independently selected from fluoro, C$_{1-4}$alkyl, preferably methyl; trifluoromethyl, hydroxymethyl, amino, hydroxyl, C$_{1-4}$alkoxy, preferably methoxy; oxo, and carboxyl, and may be independently located at any point along the chain. In some embodiments, each optional substituent is selected from fluoro, methyl, and hydroxyl. Where more than one substituent is present, substituents may be the same or different. Preferably, the number of substituents is 0 to 3; more preferably the fatty chain is unsubstituted. B may be a bond or a linker. When B is a linker, it may be a cycloalkylene, heterocycloalkylene, C$_6$arylene, or C$_{5-6}$heteroarylene, or C$_6$arylene-O— or C$_{5-6}$heteroarylene-O—.

When B is phenylene it may, for example, be selected from 1,2-phenylene, 1,3-phenylene, 1,4-phenylene, preferably 1,4-phenylene (so that A-B— is a 4-benzoic acid substituent or 4-benzoic acid bioisostere). When B is phenylene-O—, it may, for example, be selected from 1,2-phenylene-O—, 1,3-phenylene-O—, 1,4-phenylene-O—, preferably 1,4-phenylene-O. Each phenylene of B may be optionally substituted with one or more substituents selected from fluoro, methyl, trifluoromethyl, amino, hydroxyl, and C$_{1-4}$alkoxy, preferably methoxy. It will be appreciated that substituent identity and position may be selected to subtly alter the pK$_a$ of the polar group. Suitable inductively or mesomerically electron-withdrawing or donating groups and their positional effects are known in the art. In some embodiments, B may be C$_{5-6}$heteroarylene, for example, pyridinylene or thiofuranylene, and may be optionally substituted as described.

For example, in some embodiments, A-B— may be selected from:

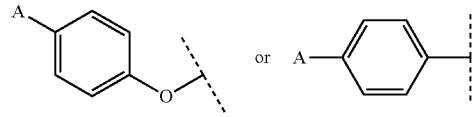

Preferably, A is H— or HOOC— and B is a bond.
It will be understood that when A is hydrogen, B is a bond and Alk is unsubstituted alkylene, A-B-Alk- is an alkyl chain of formula H$_3$C—(CH$_2$)$_n$—.

In some embodiments, $Z^1$ is an acyl group of formula:

A-B-Alk-(CO)— or a sulfonyl group of formula:

A-B-Alk-(SO$_2$)—.

Preferably, $Z^1$ is an acyl group of formula:

A-B-alkylene-(CO)— where A and B are as defined above.

In some embodiments, A is —COOH and B is a bond. Accordingly, certain preferred $Z^1$ are derived from long-chain saturated αω-dicarboxylic acids of formula HOOC—$(CH_2)_{12-22}$—COOH, preferably, long-chain saturated α,ω-dicarboxylic acids having an even number of carbon atoms in the aliphatic chain. In some other embodiments, A is H and B is a bond. Accordingly, certain preferred $Z^1$ are derived from long-chain saturated carboxylic acids of formula HOOC—$(CH_2)_{12-22}$—$CH_3$, preferably, long-chain saturated carboxylic acids having an even number of carbon atoms in the aliphatic chain.

For example, and not by way of limitation, $Z^1$ may be:
A-B-$C_{16-20}$alkylene-(CO)— wherein A is H or —COOH and B is a bond, for example:
17-carboxy-heptadecanoyl HOOC—$(CH_2)_{16}$—(CO)—;
19-carboxy-nonadecanoyl HOOC—$(CH_2)_{18}$—(CO)—;
Octadecanoyl $H_3C$—$(CH_2)_{16}$—(CO)—;
Eicosanoyl $H_3C$—$(CH_2)_{18}$—(CO)—;

The carboxylic acid group, if present, may be replaced by a bioisotere as detailed herein.

The group $Z^2$ $Z^2$ is an optional spacer that connects $Z^1$ to the side chain of the amino acid component of ψ. At its most general, $Z^2$, if present, is a spacer bound at one terminus by Y, which may be a nitrogen, oxygen or sulfur atom, and at the other terminus by X, which may be a bond or an acyl (—CO—), sulfinyl (—SO—), sulfonyl (—$SO_2$—) or absent. Accordingly, $Z^2$ may be a spacer of formula ( - - - indicate points of attachment):

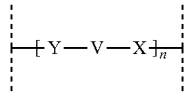

wherein:
Y may be —NH, —NR, —S or —O, where R may be alkyl, a protecting group or may form a linkage to another part of the spacer, with the remaining valency forming a linkage to $Z^1$;
X may be a bond, CO—, SO—, or $SO_2$—, with the remaining valency forming a linkage to the side chain of the amino acid component of ψ;
V is a bivalent organic moiety linking Y and X;
and n may be 1, 2, 3, 4, 5, 6, 7, 8, 9 or 10. Where n is 2 or more, each Y, V, and X is independent of every other Y, V, and X.

Accordingly, $Z^2$ may be bound at each side by amide, sulfinamide, sulfonamide, or ester linkages or by amino, ether, or thioether linkages depending upon the nature of Y and X and the corresponding linking groups on $Z^1$ and the side chain. Where n is 2 or greater, each V may also be bound to each adjacent V by linkages as described. Preferably, linkages are amides, esters or sulfonamides, most preferably amides. Accordingly, in some embodiments, each Y is —NH or —NR and each X is CO— or $SO_2$—. Most preferably, —X— is acyl (—CO—).

In some embodiments, $Z^2$ is a spacer of formula —$S_A$—, —$S_B$—, —$S_A$—$S_B$— or —$S_B$—$S_A$—, wherein $S_A$ and $S_B$ are as defined below.

In some embodiments, $Z^2$ is selected from —$S_A$— or —$S_B$—$S_A$—, that is, [side chain]-$Z^2Z^1$ is [side chain]-$S_A$—$Z^1$ or [side chain]-$S_B$—$S_A$—$Z^1$.

The group $S_A$ $S_A$ may be a single amino acid residue or a residue of an amino acid derivative, especially an amino acid derivative residue having a sulfinyl or sulfonyl in place of the carboxy moiety at the C terminus. Additionally or alternatively, the single amino acid residue may have an oxygen or sulfur atom in place of the nitrogen atom at the N terminus.

$S_A$ may be or may comprise a nitrogen-containing heterocycle, said nitrogen-containing heterocycle being bound within the lipophilic group at one end via a bond, a carboxy, a sulfinyl, or a sulfonyl group and at the other via a ring nitrogen atom. For example, $S_A$ may comprise a piperazine ring.

Suitably, $S_A$ is a 58-membered heterocycle having 1 or 2 nitrogen atoms and substituted with an X group, where X is a bond, CO—, SO—, or $SO_2$—, and where L, if present, is $C_{1-4}$alkylene (— denotes a point of attachment within the lipophilic group).

Preferably, $S_A$ is a 6-membered heterocycle having 1 or 2 nitrogen atoms, preferably 2, and substituted with a —$CH_2CO$—, —$CH_2SO$—, or —$CH_2SO_2$— group.

For example, $S_A$ may be:

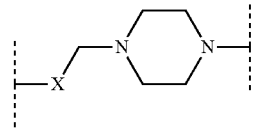

For example, $S_A$ may be:

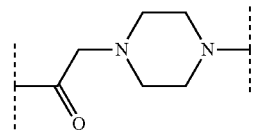

(referred to herein as piperazine-1-yl-acetyl).

Preferably, $S_A$ is a single amino acid residue or piperazine-1-yl-acetyl. More preferably $S_A$ is a single amino acid residue.

In some embodiments, the amino acid may be selected from γ-Glu, α-Glu, α-Asp, β-Asp, Ala, β-Ala (3-aminopropanoic acid), Dapa (2,3-diaminopropanoic acid), Dab (2,4-diaminobutanoic acid), and Gaba (4-aminobutanoic acid). It will be understood that where more than one carboxylic acid or amino moiety is present, connection may be at any moiety as appropriate. Any carboxylic acid or amino resides not bound within the residue may be free, that is, present as a free carboxylic acid or primary amine, or may be derivatised. Suitable derivatisation is known in the art. For example, carboxylic acid moieties may be present in $S_A$ amino acid residues as esters, for example, as methyl esters. Amino moieties may be present as alkylated amines, for example, methylated, or may be protected as amide or carbamate moieties. Other suitable amino acids include β-Ala (3-aminopropanoic acid) and Gaba (4-aminobutanoic acid) and similar ω amino acids.

It will be understood that amino acids may be D or L, or a racemic or enantioenriched mixture. In some embodiments, the amino acid is an L-amino acid. In some embodiments, the amino acid is a D-amino acid.

In some preferred embodiments, $S_A$ has a carboxylic acid substituent, with γ-Glu, α-Glu, α-Asp, and β-Asp, and sulfinyl and sulfonyl derivatives thereof, being preferred. Accordingly, in some embodiments, the amino acid residue is:

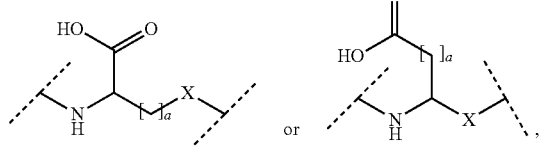

where —X— is —CO—, —SO—, —SO$_2$—, preferably —CO—, and a is 1 or 2, preferably 2. In some embodiments, the carboxylic acid is an ester, and the amino acid residue is:

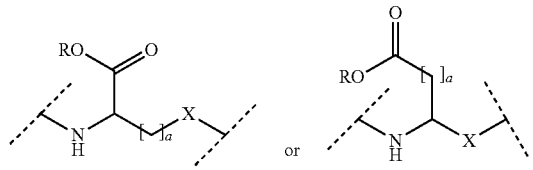

where —X— is —CO—, —SO—, —SO$_2$—, preferably —CO—, and a is 1 or 2, preferably 2, and R is $C_{1-4}$alkyl or $C_6$aryl. Preferably R is $C_{1-4}$alkyl, preferably methyl or ethyl, more preferably ethyl.

A preferred $S_A$ group bearing a carboxylic acid is γ-Glu.

Preferably, $S_A$ is selected from Dapa or γ-Glu. Most preferably, $S_A$ is γ-Glu.

The group $S_B$ $S_B$ may be a linker of general formula:

wherein $P_U$ is a polymeric unit and n is 1, 2, 3, 4, 5, 6, 7, 8, 9 or 10. One terminus of the linker $S_B$ is an —NH, —NR, —S or —O, wherein R may be alkyl, a protecting group or may form a linkage to another part of the polymeric unit; while the other is a bond or CO—, SO— or SO$_2$—. Accordingly, each polymeric unit $P_U$ may be bound at each side by amide, sulfinamide, sulfonamide, or ester linkages or by amino, ether, or thioether linkages depending upon the nature of Y and X and the corresponding linking groups on $Z^1$, $S_A$, and Lys.

In some embodiments, each $P_U$ may be independently a unit of formula:

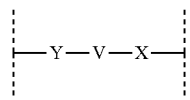

wherein:

Y may be —NH, —NR, —S or —O, wherein R may be alkyl, a protecting group or may form a linkage to another part of the spacer, with the remaining valency forming a linkage to $Z^1$;

X may be a bond, CO—, SO—, or SO$_2$—, with the remaining valency forming a linkage to the ψ side chain;

and V is a bivalent organic moiety linking Y and X.

In some embodiments, V is the α-carbon of a natural or unnatural amino acid, that is V is —CHR$^{AA}$—, wherein R$^{AA}$ is an amino acid side chain; or V is an optionally substituted $C_{1-6}$alkylene, or V is a chain comprising one or more units of ethylene glycol in series, also known as PEG chain, for example, —CH$_2$CH$_2$—(OCH$_2$CH$_2$)$_m$—O—(CH$_2$)$_p$—, where m is 0, 1, 2, 3, 4, or 5, and p is 1, 2, 3, 4, or 5; when X is CO—, p is preferably 1, 3, 4, or 5. Optional alkylene substituents include fluoro, methyl, hydroxy, hydroxymethy, and amino.

Preferred $P_U$ units include:

(i). Single amino acid residues: $P_U^i$;

(ii). Dipeptide residues: $P_U^{ii}$; and (iii). Amino-(PEG)m-carboxylic acid residues: $P_U^{iii}$, and may be present in any combination or order. For example, $S_B$ may comprise one or more of each of $P_U^i$, $P_U^{ii}$, and $P_U^{iii}$ in any order, or may comprise one or more units of $P_U^i$, $P_U^{ii}$, and $P_U^{iii}$ only, or one of more units selected from $P_U^i$ and $P_U^{ii}$, $P_U^i$ and $P_U^{iii}$, or $P_U^{ii}$ and $P_U^{iii}$.

(i). $P_U^i$ single amino acid residues

Each $P_U^i$ may be independently selected from any natural or unnatural amino acid residue and, for example, may be selected from Gly, Pro, Ala, Val, Leu, Ile, Met, Cys, Phe, Tyr, Trp, His, Lys, Arg, Gln, Asn, α-Glu, γ-Glu, Asp, Ser Thr, Dapa, Gaba, Aib, β-Ala, 5-aminopentanoyl, 6-aminohexanoyl, 7-aminoheptanoyl, 8-aminooctanoyl, 9-aminononanoyl, and 10-aminodecanoyl. Preferably, $P_U^i$ amino acid residues are selected from Gly, Ser, Ala, Thr, and Cys, more preferably from Gly and Ser.

In some embodiments, $S_B$ is —(P$_U^i$)$_n$—, wherein n is 1 to 8, more preferably 5 to 7, most preferably 6. In some preferred embodiments, $S_B$ is —(P$_U^i$)$_n$—, n is 6 and each $P_U^i$ is independently selected from Gly or Ser, with a preferred sequence being -Gly-Ser-Gly-Ser-Gly-Gly-.

(ii). $P_U^{ii}$ dipeptide residues

Each $P_U^{ii}$ may be independently selected from any dipeptide residue comprising two natural or unnatural amino acid residues bound by an amide linkage. Preferred $P_U^{ii}$ dipeptide residues include Gly-Gly, Gly-Ser, Ser-Gly, Gly-Ala, Ala-Gly, and Ala-Ala, more preferably Gly-Ser and Gly-Gly.

In some embodiments, $S_B$ is —(P$_U^{ii}$)$_n$—, wherein n is 2 to 4, more preferably 3, and each $P_U^{ii}$ is independently selected from Gly-Ser and Gly-Gly. In some preferred embodiments $S_B$ is —(P$_U^{ii}$)$_n$—, n is 3 and each $P_U^{ii}$ is independently selected from Gly-Ser and Gly-Gly, with a preferred sequence being -(Gly-Ser)-(Gly-Ser)-(Gly-Gly) (SEQ ID NO: 85).

Amino acids having stereogenic centres within $P_U^i$ and $P_U^{ii}$ may be racemic, enantioenriched, or enantiopure. In some embodiments, the or each amino acid is independently an L-amino acid. In some embodiments, the or each amino acid is independently a D-amino acid.

(iii). $P_U^{iii}$ amino-(PEG)m-carboxylic acid residues

Each $P_U^{iii}$ may be independently a residue of general formula:

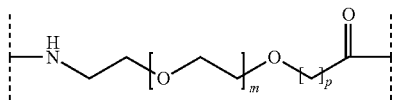

wherein m is 0, 1, 2, 3, 4, or 5, preferably 1 or 2, and p is 1, 3, 4, or 5, preferably 1.

In some embodiments, m is 1 and p is 1, that is, $P_U^{iii}$ is a residue of 8-amino-3,6-dioxaoctanoic acid (also known as {2[2-aminoethoxy]ethoxy}acetic acid and $H_2N$-$PEG_3$-COOH). This residue is referred to herein as -$PEG_3$-.

Other, longer, PEG chains are also known in the art. For example, 11-amino-3,6,9-trioxaundecanoic acid (also known as $H_2N$-$PEG_4$-COOH or -$PEG_4$-).

In some embodiments, $S_B$ is —$(P_U^{iii})_n$—, wherein n is 1 to 3, more preferably 2.

Most preferably, $S_B$ is -$PEG_3$-$PEG_3$-.

Preferred Combinations

It will be understood that the above preferences may be independently combined to give preferred —$Z^1$ and —$Z^2$—$Z^1$ moieties.

Some preferred —$Z^1$ and —$Z^2$—$Z^1$ moieties are shown below (in each case, - - - indicates the point of attachment to the side chain of the amino acid component of ψ:

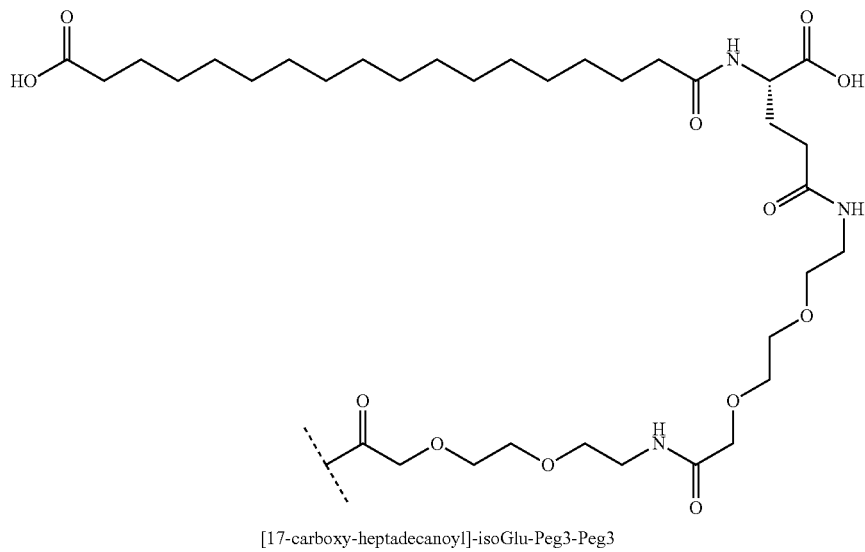

(i)

[17-carboxy-heptadecanoyl]-isoGlu-Peg3-Peg3

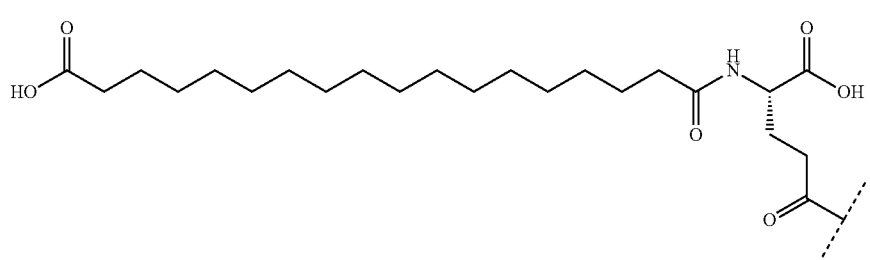

(ii)

[17-carboxy-heptadecanoyl]-isoGlu

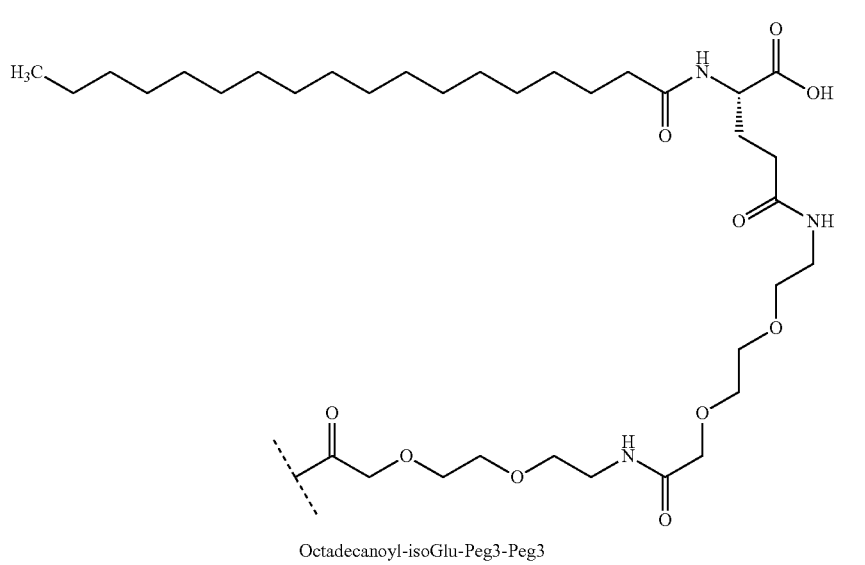

(iii)

Octadecanoyl-isoGlu-Peg3-Peg3

-continued
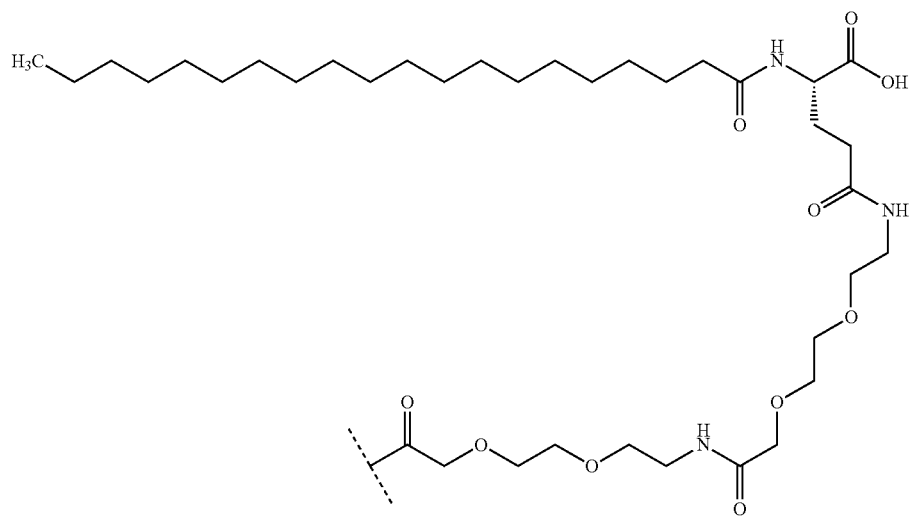
Eicosanoyl-isoGlu-Peg3-Peg3
(iv)
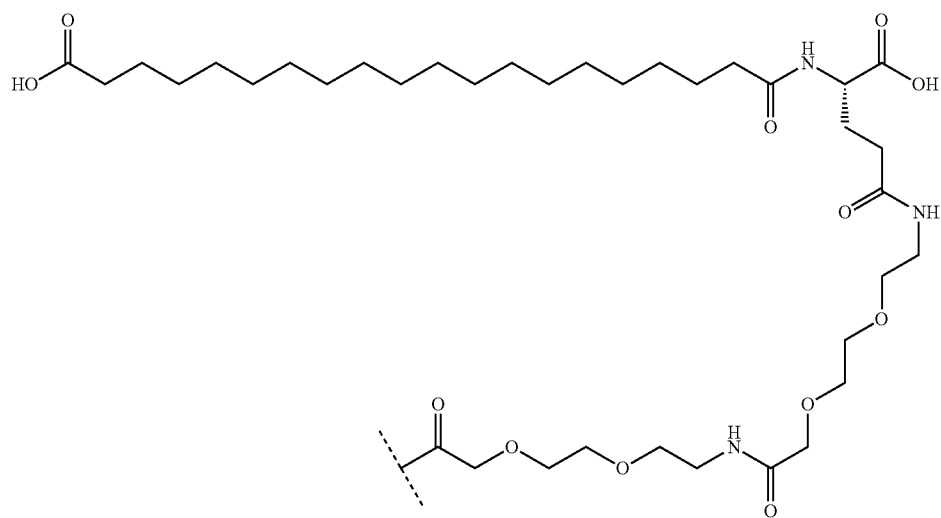
[19-carboxy-nonadecanoyl]-isoGlu-Peg3-Peg3
(v)
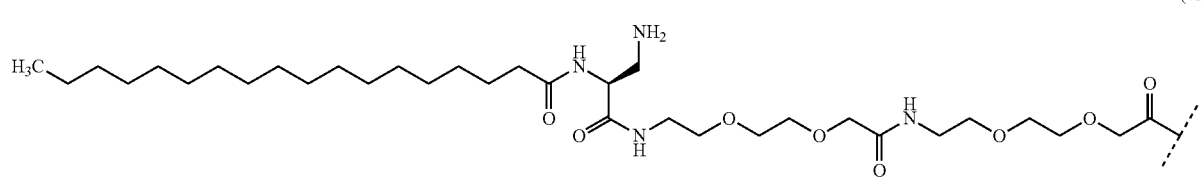
Octadecanoyl-Dapa-Peg3-Peg3
(vi)
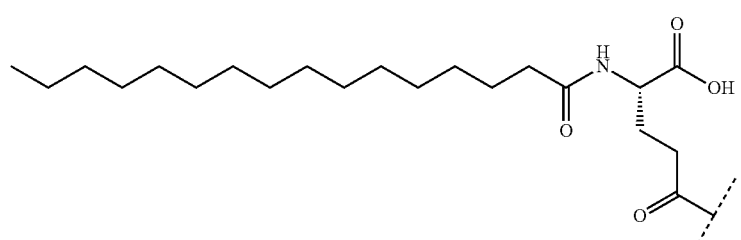
Hexadecanoyl-isoGlu
(vii)

-continued

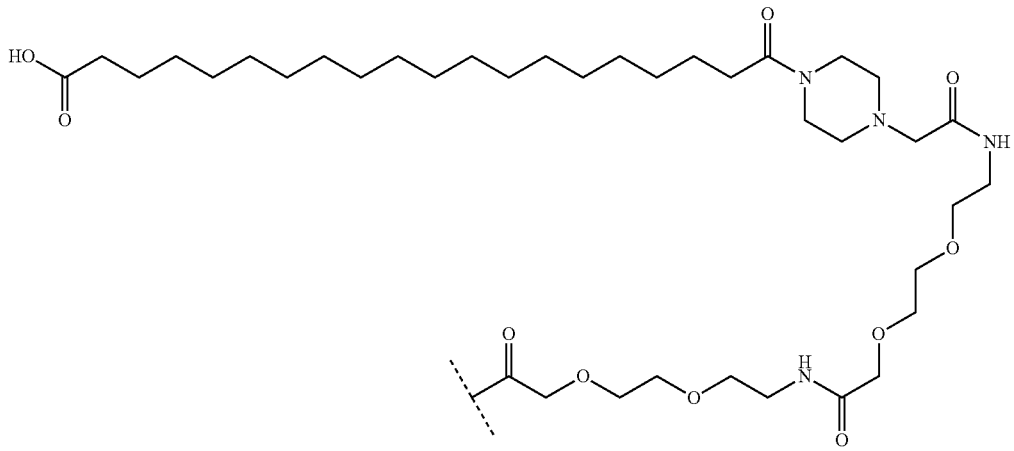

(19-Carboxy-nonadecanoyl)-[(Piperazine-1-yl)-acetyl]-Peg3-Peg3

The skilled person will be well aware of suitable techniques for preparing the compounds employed in the context of the invention. For examples of suitable chemistry, see, e.g., WO98/08871, WO00/55184, WO00/55119, Madsen et al. (*J Med. Chem.* 2007, 50, 6126-32), and Knudsen et al. 2000 (J. Med Chem. 43, 1664-1669).

Clinical Utility

The GIP analogue compounds employed in the context of the invention may provide an attractive treatment option for metabolic diseases including obesity, diabetes mellitus (diabetes), obesity-related disorders, and diabetes-related disorders. The GIP analogue compounds of the present invention may be particular effective in improving glycaemic control and reducing body weight when they are administered in combination with a GLP-1 receptor agonist (as part of the same pharmaceutical formulation or as separate formulations). Glucagon-like peptide-1 receptor agonists also known as GLP-1 receptor agonists or incretin mimetics are agonists of the GLP-1 receptor. One of their advantages over older insulin secretagogues, such as sulfonylureas or meglitinides, is that they have a lower risk of causing hypoglycemia.

Examples of GLP-1 agonists include but are not limited to exenatide (BYETTA®/BYDUREON®), liraglutide (VICTOZA®), semaglutide, lixisenatide (LYXUMIA®), albiglutide (TANZENUM®) and Taspoglutide.

Diabetes comprises a group of metabolic diseases characterized by hyperglycemia resulting from defects in insulin secretion, insulin action, or both. Diabetes is classified into type 1 diabetes, type 2 diabetes and gestational diabetes on the basis on pathogenic characteristics. Type 1 diabetes accounts for 510% of all diabetes cases and is caused by auto-immune destruction of insulin-secreting pancreatic β-cells. Acute signs of diabetes include excessive urine production, resulting compensatory thirst and increased fluid intake, blurred vision, unexplained weight loss, lethargy, and changes in energy metabolism. However, in type 2 diabetes symptoms are often not severe or may be absent. The chronic hyperglycemia of diabetes is associated with long-term damage, dysfunction, and failure of various organs, notably the eyes, kidneys, nerves, heart and blood vessels.

Type 2 diabetes accounts for 9095% of diabetes cases and is a result of a complex set of metabolic disorders. However, symptoms are often not severe or may be absent. Type 2 diabetes is the consequence of endogenous insulin production becoming insufficient to maintain plasma glucose levels below diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors, including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor-1 in the blood), and/or a proinflammatory state (e.g., elevated C-reactive protein in the blood). Conversely, obesity confers an increased risk of developing pre-diabetes, type 2 diabetes as well as, e.g., certain types of cancer, obstructive sleep apnea and gallbladder disease. Dyslipidemia is associated with increased risk of cardiovascular disease. High Density Lipoprotein (HDL) is of clinical importance since an inverse correlation exists between plasma HDL concentrations and risk of atherosclerotic disease. The majority of cholesterol stored in atherosclerotic plaques originates from LDL and hence an elevated concentration of Low Density Lipoproteins (LDL) is closely associated with atherosclerosis. The HDL/LDL ratio is a clinical risk indictor for atherosclerosis and coronary atherosclerosis in particular.

The GIP analogues of the present invention may be used as pharmaceutical agents for preventing weight gain, promoting weight loss, reducing excess body weight or treating obesity (e.g., by control of appetite, feeding, food intake, calorie intake, and/or energy expenditure and lipolysis), including morbid obesity, as well as associated diseases and health conditions including but not limited to obesity linked inflammation, obesity linked gallbladder disease and obesity induced sleep apnea. The GIP analogues employed in the context of the invention may also be used for treatment of insulin resistance, glucose intolerance, pre-diabetes, increased fasting glucose, type 2 diabetes, hypertension, dyslipidemia (or a combination of these metabolic risk factors), atherosclerosis, arteriosclerosis, coronary heart disease, peripheral artery disease and stroke. These are all conditions which may be associated with obesity. However, the effects of the compounds employed in the context of the invention on these conditions may be mediated in whole or in part via an effect on body weight, or may be independent thereof.

The GIP analogues of the present invention may thus be used for the treatment and/or prevention of any of the diseases, disorders, or conditions described herein, including insulin resistance, glucose intolerance, increased fasting glucose, pre-diabetes, type 1 diabetes, type 2 diabetes, gestational diabetes hypertension, dyslipidemia, or a combination thereof. In certain embodiments, the diabetes related disorder is selected from atherosclerosis, arteriosclerosis, coronary heart disease, peripheral artery disease and stroke; or associated with a condition selected from atherogenic dyslipidemia, blood fat disorders, elevated blood pressure, hypertension, a prothrombotic state, and proinflammatory state, or a combination thereof. In certain embodiments, the blood fat disorder is selected from high triglycerides, low HDL cholesterol, high LDL cholesterol, plaque buildup in artery walls, or a combination thereof. In certain embodiments, the prothrombotic state is selected from high fibrinogen levels in the blood and high plasminogen activator inhibitor-1 levels in the blood. In certain embodiments, the proinflammatory state is an elevated C-reactive protein level in the blood. In certain embodiments, the obesity related disorder is selected from obesity linked inflammation, obesity linked gallbladder disease and obesity induced sleep apnea.

The GIP analogues of the present invention may also be used for the treatment and/or prevention of any of the diseases, disorders, or conditions associated with diabetes related osteoporosis including increased risk of bone fractures (Khazai N. B. et al, 2009, Current Opinion in Endocrinology, Diabetes and Obesity, vol. 16, no. 6, 435-145). The increase in fracture risk is likely to be related to impaired bone quality rather than to bone mineral density. The related mechanisms, due at least in part to hyperglycemia, neuropathy, and higher incidence of hypovitaminosis D, are not yet fully understood (Takiishi T et al, 2010, Endocrinology and Metabolism Clinics of North America, vol. 39, no. 2, 419-446).

In some embodiments, the invention also provides a therapeutic kit comprising a GIP analogue (e.g., GIP agonist compound) of the present invention, optionally in combination with a pharmaceutically acceptable carrier. In some embodiments, the invention provides a device comprising a GIP analogue of the invention for delivery of the GIP analogue to a subject.

Pharmaceutical Compositions

The GIP analogues (e.g., GIP agonist compounds) of the present invention, or salts or solvates thereof, may be formulated as pharmaceutical compositions prepared for storage or administration, which typically comprise a therapeutically effective amount of a compound employed in the context of the invention, or a salt or solvate thereof, in a pharmaceutically acceptable carrier. In some embodiments, the pharmaceutical composition is formulated as a liquid suitable for administration by injection or infusion, or which is formulated to cause slow release of the GIP analogue.

The therapeutically effective amount of a compound of the present invention will depend, e.g., on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Suitable pH buffering agents may be, e.g., phosphate, citrate, acetate, lactate, maleate, tris/hydroxymethyl)aminomethane (TRIS), N-Tris(hydroxymethyl)methyl-3-aminopropanesulphonic acid (TAPS), ammonium bicarbonate, diethanolamine, histidine, which in certain embodiments is a preferred buffer, arginine, lysine, or acetate or mixtures thereof. The term further encompasses any agents listed in the US Pharmacopeia for use in animals, including humans.

The term "pharmaceutically acceptable salt" refers to a salt of the compound. Salts include pharmaceutically acceptable salts, such as, e.g., acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences"17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" may also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms (e.g. weight gain, hyperglycemia) when compared to the absence of treatment, and is not necessarily meant to imply complete cessation of the relevant condition.

The pharmaceutical compositions of the invention may be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of an injection pen. Compositions may be formulated for any suitable route and means of administration. Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for certain of the compounds described herein.

Combination Therapy

In certain embodiments, a GIP-analogue employed in the context of the invention may be administered as part of a combination therapy with at least one other agent for treatment of diabetes, obesity, dyslipidemia, or hypertension.

In such cases, the at least two active agents may be given together or separately, and as part of the same pharmaceutical formulation or as separate formulations. Thus, the GIP analogue employed in the context of the invention (or the salt or solvate thereof) may be used in combination with an antidiabetic agent including but not limited to a glucagon-like peptide receptor 1 agonist, metformin, a sulfonylurea, a glinide, a DPP-IV inhibitor, a glitazone, or insulin. In certain embodiments, the compound or salt or solvate thereof is used in combination with insulin, DPP-IV inhibitor, sulfonylurea or metformin, particularly sulfonylurea or metformin, for achieving adequate glycemic control. In certain preferred embodiments, the compound or salt or solvate thereof is used in combination with insulin or an insulin analogue for achieving adequate glycemic control. Examples of insulin analogues include but are not limited to LANTUS®, NOVORAPID®, HUMALOG®, NOVOMIX®, ACTRAPHANE HM®, LEVEMIR®, and APIDRA®.

In certain embodiments, the GIP analogue or salt or solvate thereof may further be used in combination with one or more of an anti-obesity agent, including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

In certain embodiments, the GIP analogue or salt or solvate thereof may be used in combination with an anti-hypertension agent, including but not limited to an angiotensin-converting enzyme inhibitor, angiotensin II receptor blocker, diuretics, beta-blocker, or calcium channel blocker.

In certain embodiments, the GIP analogue or salt thereof may be used in combination with an anti-dyslipidemia agent, including but not limited to a statin, a fibrate, a niacin and/or a cholesterol absorption inhibitor.

Synthesis of Compounds of the Invention

A nucleic acid molecule may encode the amino acid sequence of any of Formula I to III or a precursor thereof. The amino acid sequence encoded can be regarded as a precursor of a compound of the invention.

Typically, such nucleic acid sequences will be provided as expression constructs wherein the encoding nucleic acid is in functional linkage with appropriate control sequences to direct its expression. The expression construct may be provided in the context of a host cell capable of expressing (and optionally also secreting) the amino acid precursor, or in a cell-free expression system.

The invention provides a method of producing a GIP analogue of the invention, the method comprising expressing an amino acid precursor of the GIP analogue and modifying the precursor to provide the GIP analogue. The modification may comprise chemical modification of a Lys, Arg or Cys residue present at position 17 to introduce the lipophilic moiety, modification of the N- or C-terminus, and/or modification of any other amino acid side chains in the molecule (e.g. to introduce a non-naturally occurring amino acid residue).

The compounds of the invention may also be manufactured by standard peptide synthetic methods, e.g. by standard solid-phase or liquid-phase methodology, either stepwise or by fragment assembly, and isolating and purifying the final peptide compound product, or by any combinations of recombinant and synthetic methods.

It may be preferable to synthesize the peptide compounds of the invention by means of solid-phase or liquid-phase peptide synthesis. In this context, reference may be made to WO 98/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

EXAMPLES

The following examples demonstrate certain embodiments of the present invention. However, it is to be understood that these examples neither purport nor are they intended to be wholly definitive as to conditions and scope of this invention. The examples were carried out using standard techniques, which are well known and routine to those of skill in the art, except where otherwise described in detail. The following examples are presented for illustrative purposes only, and should not be construed in any way as limiting the scope of this invention.

Disclosed are GIP analogues that exhibit signaling selectivity, and methods for screening these compounds. Signaling selectivity may be, for example, preferential pathway activation or preferential pathway inhibition, or both. The analogue, administered alone or in combination with a GLP-1 agonist, may be useful for the treatment and/or prevention of diseases or conditions caused or characterized by excess body weight, including, but not limited to, obesity, morbid obesity, obesity linked inflammation, obesity linked gallbladder disease, obesity induced sleep apnea, metabolic syndrome, pre-diabetes, insulin resistance, glucose intolerance, type 2 diabetes, type I diabetes, hypertension, atherogenic dyslipidaemia, atherosclerosis, arteriosclerosis, coronary heart disease, peripheral artery disease, and stroke or microvascular disease.

While some embodiments of the invention have been described by way of illustration, it will be apparent that the invention can be put into practice with many different modifications, variations and adaptations, and with the use of numerous equivalents or alternative solutions that are within the scope of persons skilled in the art, without departing from the spirit of the invention or exceeding the scope of the claims.

All publications, patents, and patent applications referred to herein are herein incorporated by reference in their entirety to the same extent as if each individual publication, patent or patent application was specifically and individually indicated to be incorporated by reference in its entirety.

The methods used in the instant invention are described below, except where expressly indicated otherwise.

Example 1

General Synthesis of Acylated GIP Analogues

Solid phase peptide synthesis was performed on a CEM Liberty Peptide Synthesizer using standard Fmoc chemistry. TentaGel S Ram resin (1 g; 0.25 mmol/g) was swelled in NMP (10 ml) prior to use and transferred between tube and reaction vessel using DCM and NMP.

Coupling

An Fmoc-amino acid in DMF/DCM (2:1; 0.2 M; 5 ml) was added to the resin in a CEM Discover microwave unit together with HATU/DMF or COMU/DMF (0.5 M; 2 ml) and DIPEA-DMF/DCM (2:1) (2.0 M; 1 ml). The coupling mixture was heated to 75° C. for 5 min while nitrogen was bubbled through the mixture. The resin was then washed with DMF (4×10 ml).

Deprotection

Piperidine/DMF (20%; 10 ml) was added to the resin for initial deprotection and the mixture was heated by microwaves (30 sec; 40° C.). The reaction vessel was drained and a second portion of piperidine/NMP (20%; 10 ml) was added and heated (75° C.; 3 min.) again. The resin was then washed with DMF (6×10 ml).

Side Chain Acylation

Fmoc-Lys(ivDde)-OH or alternatively another amino acid with an orthogonal side chain protective group was introduced at the position of the acylation. The N-terminal of the peptide backbone was then Boc-protected using Boc2O or alternatively by using a Boc-protected amino acid in the last coupling. While the peptide was still attached to the resin, the orthogonal side chain protective group was selectively cleaved using freshly prepared hydrazine hydrate (24%) in NMP for 2×15 min. The unprotected lysine side chain was first coupled with Fmoc-Glu-OtBu or another spacer amino acid, which was deprotected with piperidine and acylated with a lipophilic moiety using the peptide coupling methodology as described above.

Abbreviations employed are as follows:
COMU: 1[(1-(cyano-2-ethoxy-2-oxoethylideneaminooxy)-dimethylamino-morpholinomethylene)]methanaminium hexaflourophosphate
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane Cleavage The resin was washed with EtOH (3×10 ml) and Et$_2$O (3×10 ml) and dried to constant weight at room temperature (r.t.). The crude peptide was cleaved from the resin by treatment with TFA/TIS/water (95/2.5/2.5; 40 ml, 2 h; r.t.). Most of the TFA was removed at reduced pressure and the crude peptide was precipitated and washed three times with diethylether and dried to constant weight at room temperature.

HPLC Purification of the Crude Peptide

The crude peptide was purified to greater than 90% by preparative reverse phase HPLC using a PerSeptive Biosystems VISION Workstation equipped with a C-18 column (5 cm; 10 μm) and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The final product was characterized by HPLC and MS.

The synthesized compounds are shown in Table 1.

TABLE 1

| Compound No. | Sequence |
|---|---|
| 1 | H-Y-Aib-EGTFISDYSIELDK-K(Hexadecanoyl-isoGlu)-HQQDFVNWLLAQGPSSGAPPPS-NH$_2$ |
| 2 | H-Y-Aib-EGTFISDYSIELD-K(Hexadecanoyl-isoGlu)-IHQQDFVNWLLAQGPSSGAPPPS-NH$_2$ |
| 3 | H-Y-Aib-EGTFISDYSIELEK-K(Hexadecanoyl-isoGlu)-HQQDFVNWLLAQGPSSGAPPPS-NH$_2$ |
| 4 | H-Y-Aib-EGTFISDYSIELDKIHQQDFVNWLLAQGPSSGAPPPS-K([19-carboxy-nonadecanoyl]-isoGlu-Peg3-Peg3)-NH$_2$ |
| 5 | H-Y-Aib-EGTFISDYSIELDKIHQQDFVNWLLAQGPSSGAPPPS-K(Hexadecanoyl-isoGlu)-NH$_2$ |
| 6 | H-Y-Aib-EGTFISDYSIELDKIHQQDFVNWLLAQ-K(Hexadecanoyl-isoGlu)-NH$_2$ |
| 7 | H-Y-Aib-EGTFISDYSIELDKIHQQDFVNWLLAQKG-K(Hexadecanoyl-isoGlu)-NH$_2$ |
| 8 | H-Y-Aib-EGTFISDYSIELDK-K([19-carboxy-nonadecanoyl]-isoGlu-Peg3-Peg3)-HQQDFVNYLLAQGPSSGAPPPS-NH$_2$ |
| 9 | H-Y-Aib-EGTFISDYSIELDK-K([19-carboxy-nonadecanoyl]-isoGlu-Peg3-Peg3)-HQQDFVNWLLAQGPSSGAPPPS-NH$_2$ |

TABLE 1-continued

| Compound No. | Sequence |
|---|---|
| 10 | H-Y-Aib-EGTFISDYSIELDK-K([19-carboxy-nonadecanoyl]-isoGlu-Peg3-Peg3)-AAQDFVNWLLAQGPSSGAPPPS-NH$_2$ |
| 11 | H-Y-Aib-EGTFISDYSIELEK-K([19-carboxy-nonadecanoyl]-isoGlu-Peg3-Peg3)-AAKEFVNWLLAQGPSSGAPPPS-NH$_2$ |
| 12 | H-Y-Aib-EGTFISDYSIELEK-K([19-carboxy-nonadecanoyl]-isoGlu-Peg3-Peg3)-AQRAFVEWLLAQGPSSGAPPPS-NH$_2$ |
| 13 | H-Y-Aib-EGTFISDYSIELEKIAQRAFVEWLLAQGPSSGAPPPS-K([19-carboxy-nonadecanoyl]-isoGlu-Peg3-Peg3)-NH$_2$ |
| 14 | H-Y-Aib-EGTFISDYSIELEKIAQRAFVEWLLAQ-K([19-carboxy-Nonadecanoyl]-isoGlu-Peg3-Peg3)-NH$_2$ |
| 15 | H-Y-Aib-EGTFISDYSIELDK-K([19-carboxy-nonadecanoyl]-isoGlu-Peg3-Peg3)-AAQDFVNWLLAGPSSGAPPPS-NH$_2$ |
| 16 | H-Y-Aib-EGTFISDYSIELDKIAAQDFVNWLLAGPSSGAPPPS-K([19-carboxy-nonadecanoyl]-isoGlu-Peg3-Peg3)-NH$_2$ |
| 17 | H-Y-Aib-EGTFISDYSIELDK-K([19-Carboxy-nonadecanoyl]-isoGlu-Peg3-Peg3)-AQRAFVEWLLAQGPSSGAPPPS-NH$_2$ |
| 18 | H-Y-Aib-EGTFISDYSIELDK-K([19-Carboxy-nonadecanoyl]-isoGlu-Peg3-Peg3)-AQRAFIEWLLAQGPSSGAPPPS-NH$_2$ |
| 19 | H-Y-Aib-EGTFISDYSIELDK-K((19-Carboxy-nonadecanoyl)-[(Piperazine-1-yl)-acetyl]-Peg3-Peg3)-AQRAFIEWLLAQGPSSGAPPPS-NH$_2$ |
| 20 | H-Y-Aib-EGTFISDYSIELDK-K((19-Carboxy-nonadecanoyl)-[(Piperazine-1-yl)-acetyl]-Peg3-Peg3)-AQRAFVEWLLAQGPSSGAPPPS-NH$_2$ |
| 21 | H-Y-Aib-EGTFISDYSIELDK-K((19-Carboxy-nonadecanoyl)-[(Piperazine-1-yl)-acetyl]-Peg3-Peg3)-AQKEFVEWLLAAGPSSGAPPPS-NH$_2$ |
| 22 | H-Y-Aib-EGTFISDYSIELDK-K([19-Carboxy-nonadecanoyl]-isoGlu-Peg3-Peg3)-AQKEFVEWLLAAGPSSGAPPPS-NH$_2$ |
| 23 | H-Y-Aib-EGTFISDYSIELDKIAQRAFIEWLLAGPSSGAPPPS-K([19-Carboxy-nonadecanoyl]-isoGlu-Peg3-Peg3)-NH$_2$ |
| 24 | H-Y-Aib-EGTFISDYSIELDKIAQKEFIEWLLAGPSSGAPPPS-K([19-Carboxy-nonadecanoyl]-isoGlu-Peg3-Peg3)-NH$_2$ |
| 25 | H-Y-Aib-EGTFISDYSIELDKIAAQDFIEWLLAGPSSGAPPPS-K([19-Carboxy-nonadecanoyl]-isoGlu-Peg3-Peg3)-NH$_2$ |
| 26 | H-Y-Aib-EGTFISDYSIELDKIAAQDFIEWLLAGPSSGAPPPS-K((19-Carboxy-nonadecanoyl)-[(Piperazine-1-yl)-acetyl]-Peg3-Peg3)-NH$_2$ |
| 27 | H-Y-Aib-EGTFISDYSIELDKIAAQDFVEWLLAGPSSGAPPPS-K([19-Carboxy-nonadecanoyl]-isoGlu-Peg3-Peg3)-NH$_2$ |
| 28 | H-Y-Aib-EGTFISDYSIELDKIAQRAFIEWLLAQGPSSGAPPPS-K([19-Carboxy-nonadecanoyl]-isoGlu-Peg3-Peg3)-NH$_2$ |
| 29 | H-Y-Aib-EGTFISDYSIELDK-K([19-Carboxy-nonadecanoyl]-isoGlu-Peg3-Peg3)-AAQAFVNWLLAGPSSGAPPPS-NH$_2$ |
| 30 | H-Y-Aib-EGTFISDYSIELDK-K([19-Carboxy-nonadecanoyl]-isoGlu-Peg3-Peg3)-AAQDFVNWLLAAGPSSGAPPPS-NH$_2$ |
| 31 | H-Y-Aib-EGTFISDYSIELDK-K([19-Carboxy-nonadecanoyl]-isoGlu-Peg3-Peg3)-AAQDFINWLLAGPSSGAPPPS-NH$_2$ |
| 32 | H-Y-Aib-EGTFISDYSIELDK-K([19-Carboxy-nonadecanoyl]-isoGlu-Peg3-Peg3)-AAQDFIEWLLAGPSSGAPPPS-NH$_2$ |
| 33 | H-Y-Aib-EGTFISDYSIELDK-K((19-Carboxy-nonadecanoyl)-[(Piperazine-1-yl)-acetyl]-Peg3-Peg3)-AAQDFIEWLLAGPSSGAPPPS-NH$_2$ |
| 34 | H-Y-Aib-EGTFISDYSIELD-K([19-Carboxy-nonadecanoyl]-isoGlu-Peg3-Peg3)-IAQRAFIEWLLAQGPSSGAPPPS-NH$_2$ |
| 35 | H-Y-Aib-EGTFISDYS-K([19-Carboxy-nonadecanoyl]-isoGlu-Peg3-Peg3)-ELDKIAQRAFIEWLLAQGPSSGAPPPS-NH$_2$ |
| 36 | H-Y-DAla-EGTFISDYSIELDK-K([19-Carboxy-nonadecanoyl]-isoGlu-Peg3-Peg3)-AQRAFIEWLLAQGPSSGAPPPS-NH$_2$ |
| 37 | H-Y-DAla-EGTFISDYSIELDKIAAQDFIEWLLAGPSSGAPPPS-K((19-Carboxy-nonadecanoyl)-[(Piperazine-1-yl)-acetyl]-Peg3-Peg3)-NH$_2$ |

TABLE 1-continued

| Compound No. | Sequence |
|---|---|
| 38 | H-Y-Aib-EGTFISDYSIELDK-K([19-Carboxy-nonadecanoyl]-isoGlu-Peg3-Peg3)-AAQDFIEWLLAQGPSSGAPPPS-NH$_2$ |
| 39 | H-Y-Aib-EGTFISDYSIELDK-K([19-Carboxy-nonadecanoyl]-isoGlu-Peg3-Peg3)-AAQDFINWLLAQGPSSGAPPPS-NH$_2$ |
| 40 | H-Y-Aib-EGTFISDYSIELDK-K([19-Carboxy-nonadecanoyl]-isoGlu-Peg3-Peg3)-AAQAFIEWLLAQGPSSGAPPPS-NH$_2$ |
| 41 | H-Y-Aib-EGTFISDYSIELDK-K((19-Carboxy-nonadecanoyl)-[(Piperazine-1-yl)-acetyl]-Peg3-Peg3)-AAQAFIEWLLAQGPSSGAPPPS-NH$_2$ |

Synthesis of Compound No. 9

Solid phase peptide synthesis was performed on a CEM Liberty Peptide Synthesizer using standard Fmoc chemistry. TentaGel S Ram S resin (1.05 g; 0.23 mmol/g) was swelled in DMF (10 ml) prior to use and transferred between tube and reaction vessel using DCM and DMF.

Coupling

An Fmoc-amino acid in DMF/DCM (2:1; 0.2 M; 5 ml) was added to the resin in a CEM Discover microwave unit together with COMU/DMF (0.5 M; 2 ml) and DIPEA-DMF/DCM (2:1) (2.0 M; 1 ml). The coupling mixture was heated to 75° C. for 5 min while nitrogen was bubbled through the mixture. The resin was then washed with DMF (4×10 ml). Fmoc-Tyr(OtBu)-Ser(Psi Me,Me)-OH pseudoproline was used for amino acid number 29 and 30 counting from the C-terminal. Lys17 was incorporated as Fmoc-Lys(Dde)-OH for orthogonal coupling. The first 9 amino acids and amino acid number 24 (counting from the C-terminal) was double couple meaning the building block was coupled twice before deprotection. Boc-Tyr(tBu)-OH was incorporated as the final building block in the N-terminal.

Deprotection

Piperidine/DMF (20%; 10 ml) was added to the resin for initial deprotection and the mixture was heated by microwaves (30 sec; 40° C.). The reaction vessel was drained and a second portion of piperidine/DMF (20%; 10 ml) was added and heated (75° C.; 3 min.) again. The resin was then washed with DMF (6×10 ml).

Side Chain Acylation

While the peptide was still attached to the resin, the orthogonal side chain protective group was selectively cleaved using freshly prepared hydrazine hydrate (24%) in NMP for 2×15 min. The unprotected lysine side chain was first coupled with Fmoc-Glu-OtBu and the two Peg3 building blocks using standard coupling and deprotection conditions as explained above. Lastly the lipophilic moiety was incorporated as a 19-carboxy-nonadecanoic acid mono tert butyl ester again using standard coupling conditions.

Cleavage

The resin was washed with EtOH (3×10 ml) and Et2O (3×10 ml) and dried to constant weight at room temperature (r.t.). The crude peptide was cleaved from the resin by treatment with TFA/TIS/H$_2$O (95/2.5/2.5; 60 ml, 2 h; r.t.). Most of the TFA was removed at reduced pressure and the crude peptide was precipitated and washed three times with diethylether and dried to constant weight at room temperature.

HPLC Purification of the Crude Peptide

The crude peptide was first purified from 30% by preparative reverse phase HPLC using a Gilson 331 pump with a Gilson GX281 fraction collector equipped with a Gemini NX 5µ C-18 110 A, 10×250 mm column and run at 47 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. A second purification was performed using the same method to obtain the product in 96% purify (53 mg) as characterized by HPLC and MS. Calculated monoisotopic mass=5025.54 found 5025.72.

Example 2

Human GIP Receptor (GIP R) Activity Assay

In vitro effects of peptide conjugates of the invention were assessed by measuring the induction of cAMP following stimulation of the respective receptor by GIP or analogues of these, as outlined in the invention, using the AlphaSceen® cAMP kit from Perkin-Elmer according to instructions. Briefly, HEK293 cells expressing the human GIP R (stable cell lines generated through transfection of the cDNA for human GIP R and selection of stable clones) were seeded at 30,000 cells/well in 96-well microtiter plates coated with 0.01% poly-L-lysine, and grown for 1 day in culture in 200 µl growth medium (DMEM, 10% FCS, Penicillin (100 IU/ml), Streptomycin (100 µg/ml)). On the day of analysis, growth medium was removed and the cells were washed once with 150 µl Tyrode's buffer (Tyrode's Salts (9.6 g/l), 10 mM HEPES, pH 7.4). Cells were then incubated in 100 µl Assay buffer (0.1% W/V Alkali-treated Casein and 100 µM IBMX in Tyrode's Buffer) containing increasing concentrations of control and test compounds for 15 min at 37° C. The Assay buffer was removed and cells are lysed in 80 µl Lysis buffer (0.1% w/v BSA, 5 mM HEPES, 0.3% v/v Tween-20) per well. From each well 10 µl lysed cells was transferred to a 384-well plate and mixed with 15 µl bead-mix (1 Unit/15 µl anti-cAMP Acceptor Beads, 1 Unit/15 µl Donor Beads, and 1 Unit/15 µl Biotinylated cAMP in Assay Buffer). The plates were mixed and incubated in the dark for an hour at room temperature before measuring using an Envision™ plate reader (Perkin-Elmer).

Results were converted into cAMP concentrations using a cAMP standard curve prepared in KRBH buffer containing 0.1% (v/v) DMSO. The resulting cAMP curves were plotted as absolute cAMP concentrations (nM) over log (test compound concentration) and analyzed using the curve fitting program XLfit.

Parameter calculated to describe both the potency as well as the agonistic activity of each test compound on the receptors were:

EC50, a concentration resulting in a half-maximal elevation of cAMP levels, reflecting the potency of the test compound. The results are summarized in Table 2.

TABLE 2

EC$_{50}$ average values of the compounds on the GIP-R compared to control peptide.

| Compound | hGIP-R level of cAMP (nM) |
|---|---|
| hGIP | 0.003 |
| 1 | 0.008 |
| 2 | 0.013 |

TABLE 2-continued

EC$_{50}$ average values of the compounds on the GIP-R compared to control peptide.

| Compound | hGIP-R level of cAMP (nM) |
|---|---|
| 3 | 0.014 |
| 4 | 0.013 |
| 5 | 0.014 |
| 6 | 0.032 |
| 7 | 0.018 |
| 8 | 0.009 |
| 9 | 0.008 |
| 10 | 0.007 |
| 11 | 0.009 |
| 12 | 0.009 |
| 13 | 0.014 |
| 14 | 0.024 |
| 15 | 0.012 |
| 16 | 0.016 |
| 17 | 0.007 |
| 18 | 0.006 |
| 19 | 0.006 |
| 20 | 0.007 |
| 21 | 0.007 |
| 22 | 0.005 |
| 23 | 0.010 |
| 24 | 0.008 |
| 25 | 0.032 |
| 26 | 0.017 |
| 27 | 0.013 |
| 28 | 0.007 |
| 29 | 0.014 |
| 30 | 0.009 |
| 31 | 0.012 |
| 32 | 0.020 |
| 33 | 0.014 |
| 34 | 0.011 |
| 35 | 0.008 |
| 36 | 0.006 |
| 37 | 0.016 |
| 38 | 0.001 |
| 39 | 0.007 |
| 40 | 0.010 |
| 41 | 0.014 |

Example 3

Activity Assays at Human GIP Receptor (GIP R) and Human GLP-1 Receptor (GLP-1R)

In vitro effects of peptide conjugates were assessed by measuring the induction of cAMP following stimulation of the respective receptor using the AlphaScreen® cAMP kit from Perkin-Elmer according to instructions. Briefly, HEK293 cells expressing the GIP R or the GLP-1R (stable cell lines generated through transfection of expression vector containing the cDNA for the receptor in question and selection of stable clones) were seeded at 30,000 cells/well in 96-well microtiter plates coated with 0.01% poly-L-lysine, and grown for 1 day in culture in 200 µl growth medium (DMEM, 10% FCS, Penicillin (100 IU/ml), Streptomycin (100 µg/ml)). On the day of analysis, growth medium was removed and the cells were washed once with 150 µl Tyrode's buffer (Tyrode's Salts (9.6 g/l), 10 mM HEPES, pH 7.4). Cells were then incubated in 100 µl Assay buffer (0.05% W/V Alkali-treated Casein and 100 µM IBMX in Tyrode's Buffer) containing increasing concentrations of control and test compounds for 15 min at 37° C. The Assay buffer was removed and cells are lysed in 80 µl Lysis buffer (0.1% w/v BSA, 5 mM HEPES, 0.3% v/v Tween-20) per well. From each well 10 µl lysed cells was transferred to a 384-well plate and mixed with 15 µl bead-mix (1 Unit/15 µl anti-cAMP Acceptor Beads, 1 Unit/15 µl Donor Beads, and 1 Unit/15 µl Biotinylated cAMP in Assay Buffer). The plates were mixed and incubated in the dark for an hour at room temperature before measuring using an Envision™ plate reader (Perkin-Elmer).

The cAMP response was normalized relative to a positive and negative control (reference agonist (0.1 nM human GIP or 1 nM Exendin-4) and assay buffer, respectively) to calculate the EC50 and maximal response from the concentration response curve using 4 parameter logistic (4PL) nonlinear regression model for curve fitting.

The EC50s, a concentration resulting in a half-maximal elevation of cAMP levels, reflecting the potencies of the test agonist compounds are summarized in Table 2a.

TABLE 2a

EC$_{50}$ average values of the compounds compared to control peptides.

| Compound | EC50 hGIP R (nM) | EC50 hGLP1 R (nM) |
|---|---|---|
| Exendin-4 | NT | 0.004 |
| hGIP | NT | >100 |
| 1 | 0.003 | NA |
| 2 | 0.008 | NT |
| 3 | 0.014 | NA |
| 4 | 0.014 | NT |
| 5 | 0.014 | NT |
| 6 | 0.014 | NT |
| 7 | 0.032 | NA |
| 8 | 0.019 | >10 |
| 9 | 0,009 | >3 |
| 10 | 0.008 | >10 |
| 11 | 0.008 | >3 |
| 12 | 0.009 | >3 |
| 13 | 0.008 | >10 |
| 14 | 0.014 | >10 |
| 15 | 0.024 | >100 |
| 16 | 0.012 | >10 |
| 17 | 0.016 | >3 |
| 18 | 0.007 | >3 |
| 19 | 0.005 | >3 |
| 20 | 0.006 | >3 |
| 21 | 0.006 | >3 |
| 22 | 0.007 | >10 |
| 23 | 0.005 | >10 |
| 24 | 0.010 | >10 |
| 25 | 0.008 | >100 |
| 26 | 0.032 | >10 |
| 27 | 0.017 | >10 |
| 28 | 0.013 | >3 |
| 29 | 0.007 | >100 |
| 30 | 0.014 | >10 |
| 31 | 0.009 | >100 |
| 32 | 0.012 | >100 |
| 33 | 0.020 | >10 |
| 34 | 0.017 | >10 |
| 35 | 0.011 | >3 |
| 36 | 0.006 | >10 |
| 37 | 0.006 | >10 |
| 38 | 0.017 | >100 |
| 39 | 0.001 | >100 |
| 40 | 0.007 | >10 |
| 41 | 0.010 | >10 |

NT = Not tested,
NA = No activity

Example 4

Pharmacokinetics of Selected Compounds in Mice
Method

C57BL/6J mice (males with a body weight of approximately 25 g) were given either a single subcutaneous (s.c.) bolus or a single intravenous (i.v.) bolus of each peptide to be tested.

Following s.c. administration of the selected compounds (50, 100 or 200 nmol/kg), blood samples were drawn at 8 (eight) timepoints up to 96 hours post-dose. Following i.v. administration of the selected compounds (50, 100 or 200 nmol/kg), blood samples were drawn at 8 (eight) timepoints up to 72 hours post-dose. Blood samples were drawn by sublingual bleeding. The dosing vehicle was a phosphate buffer containing mannitol (pH 7.5).

At each sampling time point, samples from two mice were drawn, i.e. 16 mice were included for each compound and each administration route. The mice were euthanized immediately after blood sampling by cervical dislocation. Plasma samples were analyzed after solid phase extraction (SPE) or protein precipitation followed by liquid chromatography mass spectrometry (LC-MS/MS). Mean plasma concentrations were used for calculation of the pharmacokinetic parameters using the non-compartmental approach in Phoenix WinNonlin 6.3. Plasma terminal elimination half-life (T½) was determined as $\ln(2)/\lambda z$ where $\lambda z$ is the magnitude of the slope of the log linear regression of the log concentration versus time profile during the terminal phase. Bioavailability was determined as $AUC_{inf}$ (s.c.)/$AUC_{inf}$(i.v.)×100, where $AUC_{inf}$ is the area under the plasma concentration–time curve extrapolated to infinity ($AUC_{inf}=AUC_{last}+C_{last}/\lambda z$, where $C_{last}$ is the last observed plasma concentration). $T_{max}$ is the post-dose time where the maximal plasma concentration was observed. The results are summarized in Table 3.

TABLE 3

Terminal elimination half-life (h) and bioavailability in mice following s.c. and i.v. administration of selected compounds.

| Compound | T½ (h.) i.v. | T½ (h.) s.c. | Tmax (h.) s.c. | Bioavailability s.c. |
|---|---|---|---|---|
| hGIP | 0.1 | — | — | — |
| 10 | 16.9 | 21.1 | 4 | 100%*^ |
| 12 | 14.7 | 16.8 | 8 | 77%^ |
| 15 | 19.2 | 16.7 | 8 | 87% |
| 16 | 23.3 | 23.6 | 8 | 81% |
| 13 | 14.4 | 13.7 | 8 | 75% |
| 16 | 19.2 | 16.7 | 8 | 88% |
| 17 | 16.3 | 19.9 | 8 | 56% |
| 18 | 17.6 | 15.1 | 4 | 78% |
| 21 | 24.8 | 21.0 | 8 | 67% |
| 33 | 21.7 | 18.7 | 8 | 78% |
| 35 | 14.5 | 14.5 | 4 | 73% |
| 41 | 17.6 | 16.5 | 8 | 70% |

*The bioavailability was capped to 100%
^In a repeated test the bioavalability of Compound 10 was 77% and the bioavailability of Compound 12 was 98%.

Example 5

OGTT (Oral Glucose Tolerance Test) in Normal Mice.

Figure 1D:
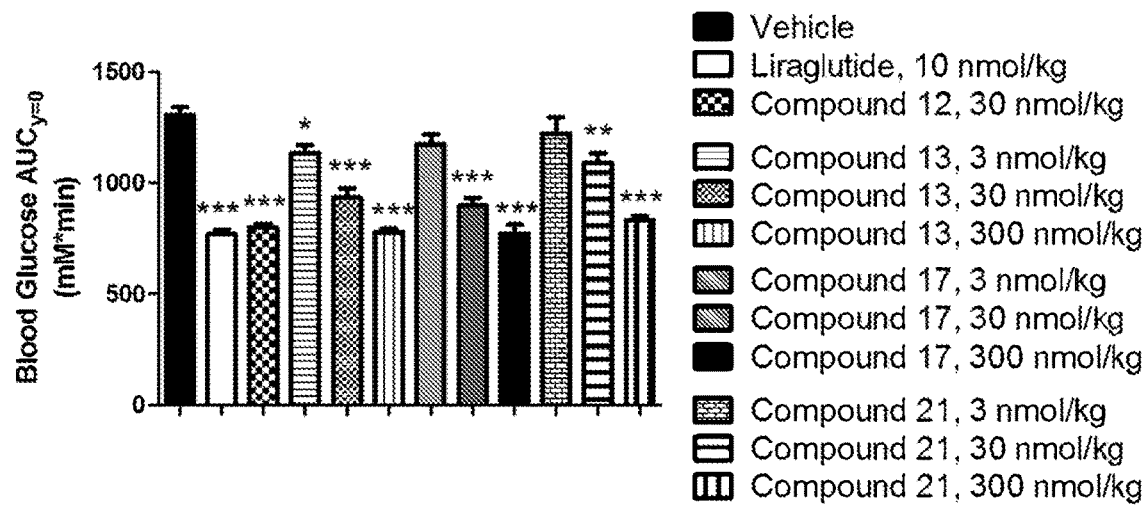
Figure 2C:
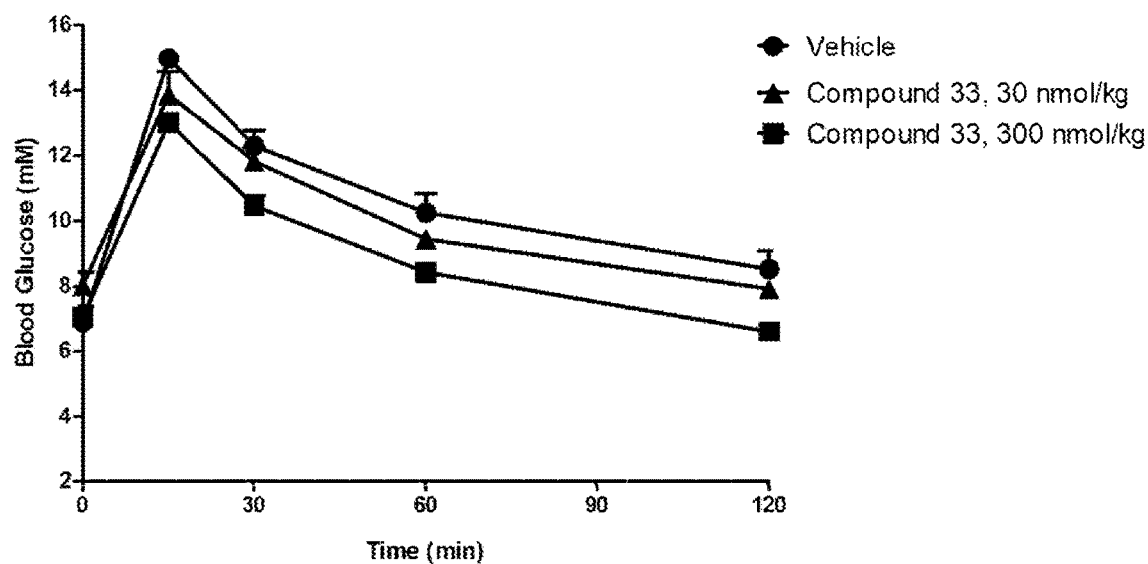
Figure 2D:
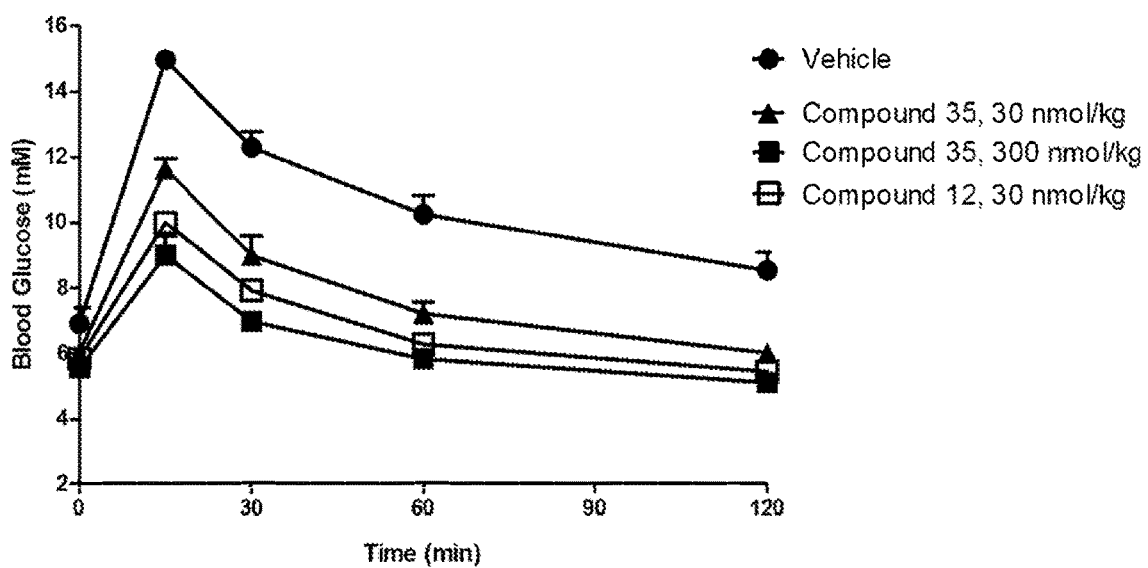
Figure 2E:
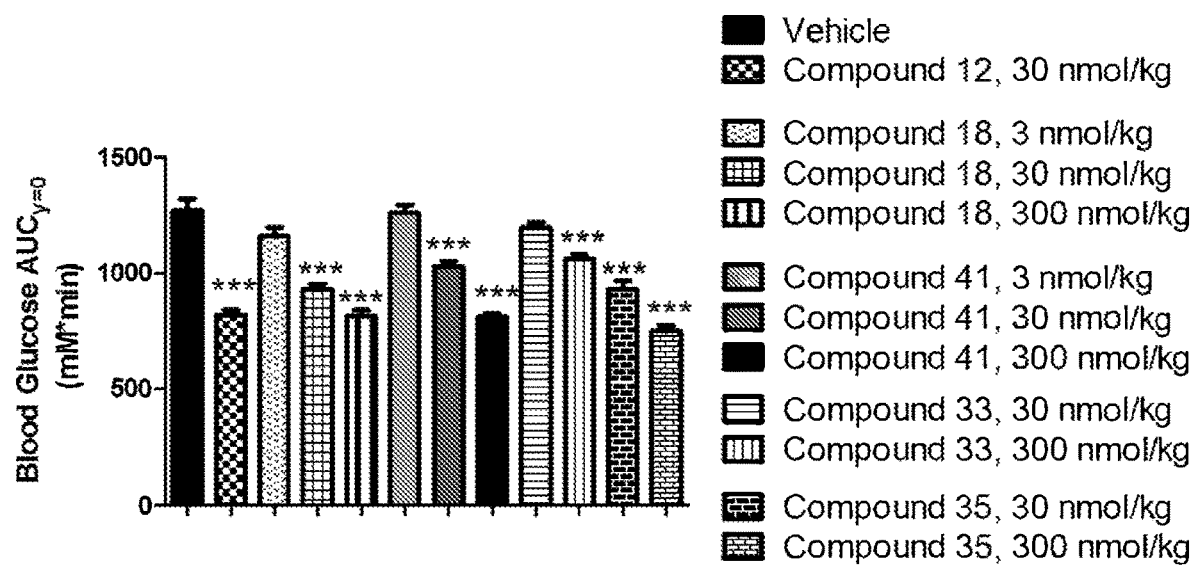

Male C57BL/6J mice (Charles River, Germany) were maintained on normal chow (Altromin 1324, Brogaarden A/S, Gentofte, Denmark) and domestic quality water with added citric acid to pH ~3.6. The animals were housed in groups of n=3 in a light-, temperature-, and humidity-controlled room (12:12 h light-dark cycle, with lights on at 06.0018.00 hr; 21±1° C.; 5080% relative humidity). Mice, 1012 weeks old, were fasted 5 hours before the OGTT. GIP receptor agonists (3300 nmol/kg), the GLP-1 analogue liraglutide (10 nmol/kg) and vehicle were administered (5 mL/kg) subcutaneously (s.c.) 4 hours before the oral gavage of glucose (t=0 min; 2 g/kg; 5 mL/kg). Tail vein blood was sampled at time t=0 (before glucose administration), 15, 30, 60, and 120 min for measurements of blood glucose. Results (blood glucose levels and area under the blood glucose curves (AUC). Data are means±SEM; n=6) from 2 experiments are shown in FIGS. 1 (A-D) and 2 (A-E).

Statistical analyses were performed using Graph Pad Prism version 5. The blood glucose AUCs were compared using one-way ANOVA followed by Dunnett's Multiple Comparison Tests vs. vehicle group. Differences were considered statistically significant at p<0.05. Statistical differences vs vehicle: *p<0.05, p<0.01, *p<0.001.

Example 6

Figure 3:
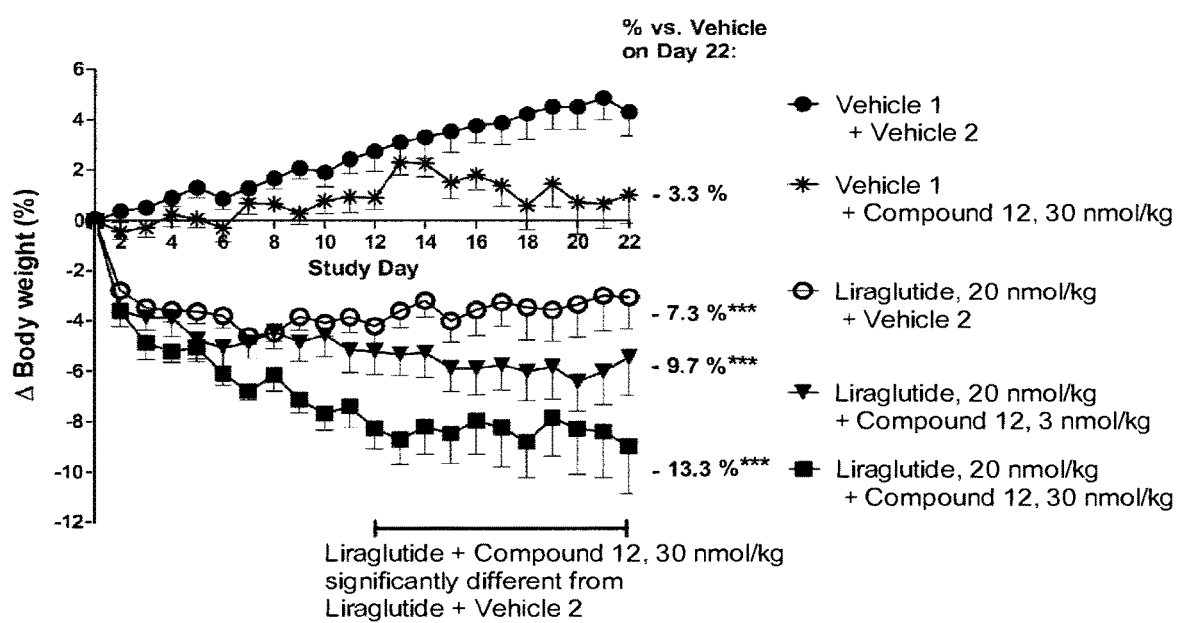
FIG. 3: Relative body weight changes (delta Δ bodyweight=body weight at each study day–body weight at day 1) in DIO mice during three weeks of treatment. Animals were treated once daily with two separate s.c. injections. The first injection was with vehicle 1 or GLP-1 analogue liraglutide (20 nmol/kg). The second injection was with vehicle 2 or Compound 12 (3 and 30 nmol/kg). The GIP agonist was only dosed every third day of the study (starting on day 1). On other days, GIP agonist was replaced with vehicle 2. Data are means±SEM; n=89. Statistical differences vs vehicle on day 22: ***p<0.001. Statistical difference (p<0.05) between liraglutide and liraglutide co-treated GIP agonist is shown with a line.

Sub-Chronic Effects of Co-Treatment of Gip Receptor Agonist and Glp-1 Receptor Agonist on Body Weight in Diet-Induced Obese (DIO) C57BL/6J Mice Male C57BL/6J (JAX) mice (Charles River, UK) fed high-fat diet (45% of total energy from fat, D12451 Research Diet Inc.) for approximately 4 months were used. The animals were housed in groups of n=3 in a light-, temperature-, and humidity-controlled room (12:12 h light-dark cycle, with lights on at 07.0019.00 hr; 21±2° C.; 55±20% relative humidity). Mice were single-housed two weeks prior to start of the mock phase. All mice were mock-treated (once daily s.c. injection of vehicle) for a week to acclimatize the animals to handling and injections. Subsequently, the mice were stratified according to body weight into treatment groups (n=8-9). The average starting body weight was 39-40 grams. Animals were thereafter treated once daily with two separate s.c. injections (3 mL/kg of each injection) from day 1 to day 22. The first injection was with vehicle 1 (25 mM phosphate, 125 mM sodium chloride buffer, pH 7.4) or GLP-1 analogue liraglutide (20 nmol/kg). The second injection was with vehicle 2 (25 mM phosphate, 205 mM D-Mannitol, pH 7.5) or GIP agonist (3 and 30 nmol/kg). The GIP agonist was only dosed every third day of the study (starting on day 1). On other days, GIP agonist was replaced with vehicle 2. The daily injections were given in the morning (at 9.00-10.00). Body weight was determined daily throughout the study. Changes in body weight during the study are shown in FIG. 3 (delta Δ=body weight at each study day–body weight at day 1. Data are means±SEM).

Statistical analyses were performed using Graph Pad Prism version 5. The change in body weight of liraglutide-treated mice was compared with mice co-administered liraglutide and GIP agonist by two-way ANOVA followed by Bonferroni posttests. P<0.05 was considered statistically significant. The change in body weight of vehicle-treated control mice was compared with compound-treated mice by two-way ANOVA followed by Bonferroni posttests; ***p<0.001 vs. vehicle. Statistical differences vs vehicle are shown for day 22 in FIG. 3.

Example 7

Figure 4C:
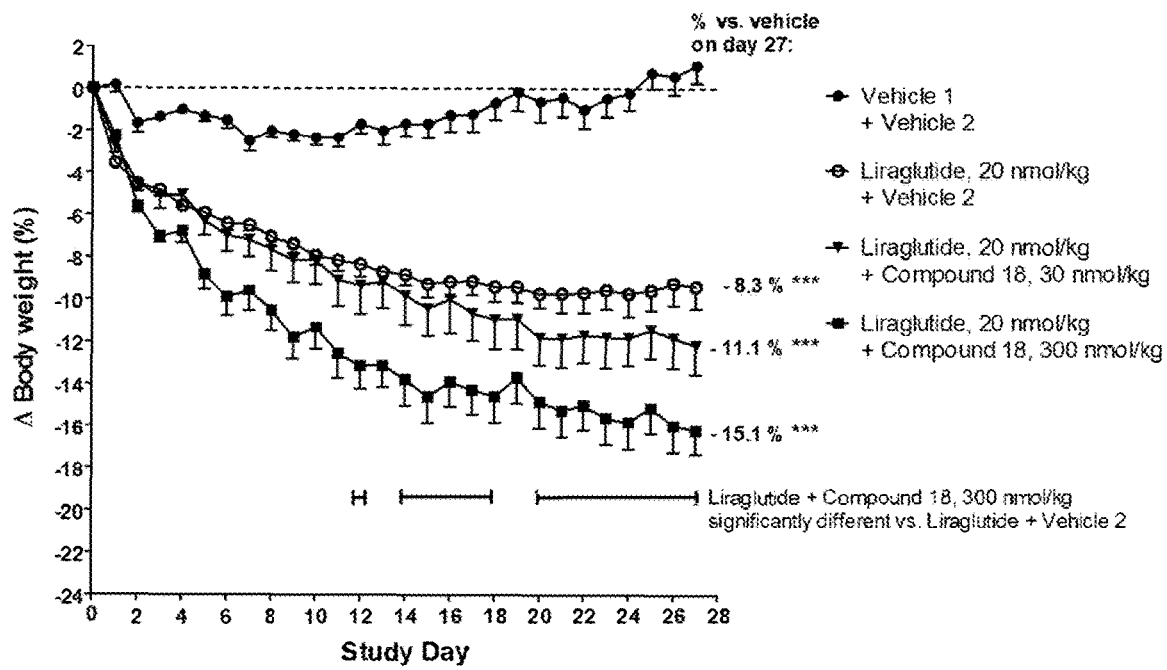
Figure 4D:
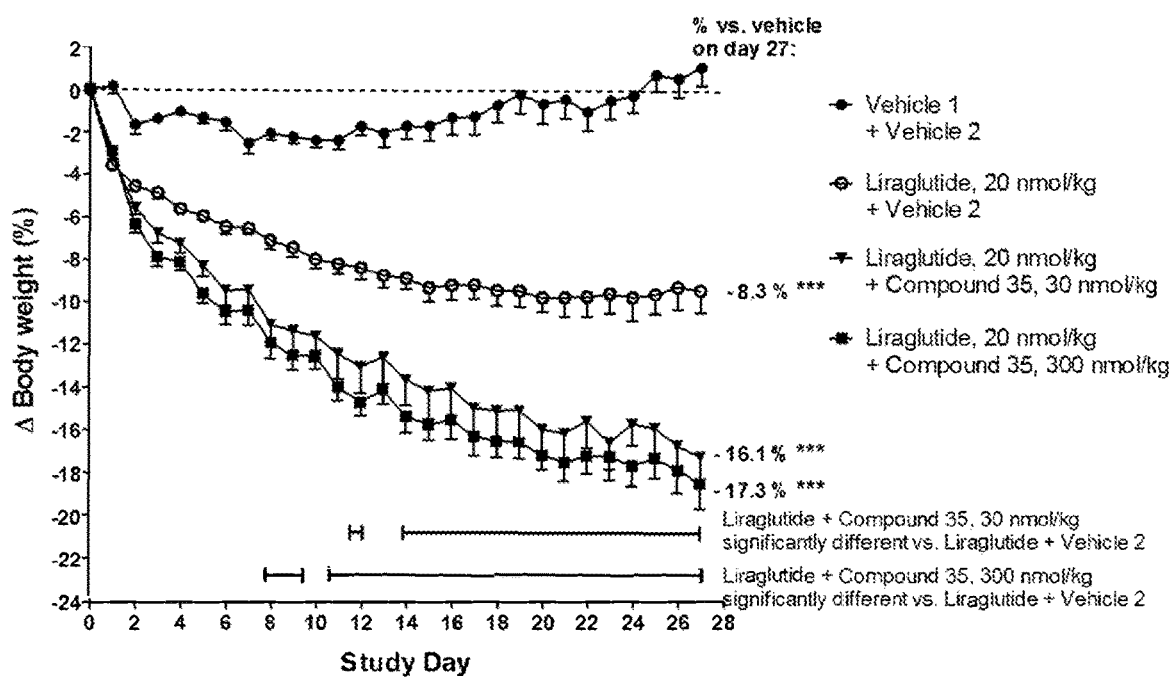
Figure 4E:
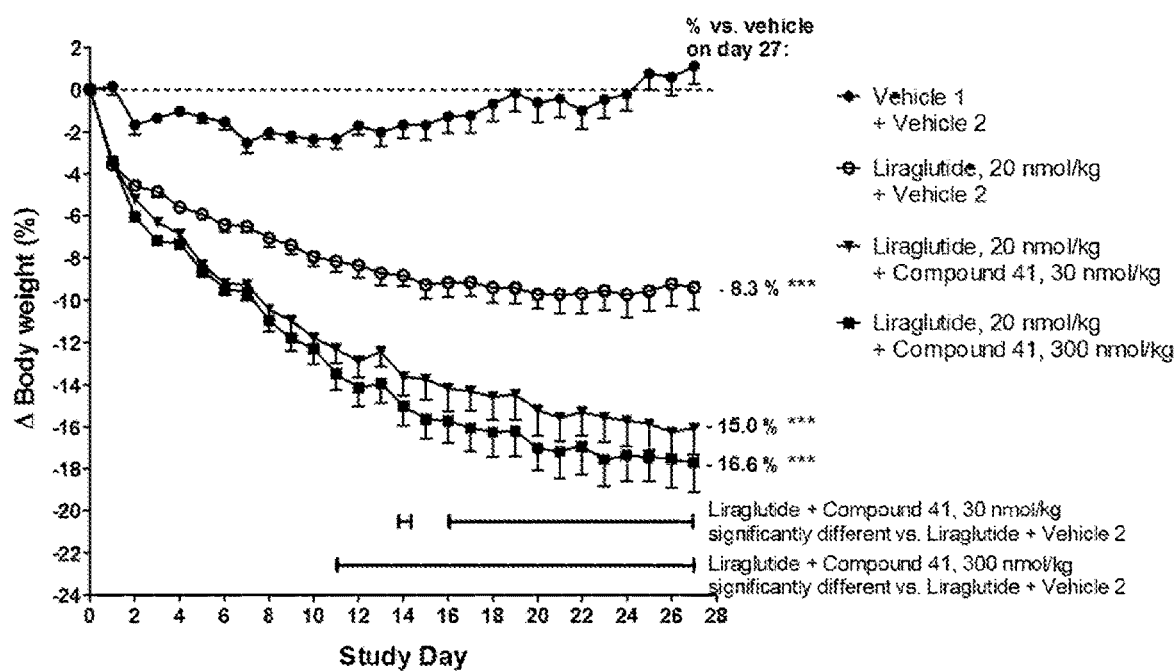

Sub-Chronic Effects of Co-Treatment of GIP Receptor Agonists and GLP-1 Receptor Agonist on Body Weight in Diet-Induced Obese (DIO) C57BL/6J Mice Male C57BL/6J mice (Charles River, Germany) fed high-fat diet (60% of total energy from fat, DIO Rodent Purified 58Y1-58126 from TestDiet) for approximately 5 months were used. The animals were housed in groups of n=3 in a light-, temperature-, and humidity-controlled room (12:12 h light-dark cycle, with lights on at 06.00-18.00 hr; 21±1° C.; 65±15% relative humidity). All mice were mock-treated (once daily s.c. injection of vehicle) for a week to acclimatize the animals to handling and injections. Subsequently, the mice were stratified according to body weight into treatment groups (n=9). The average starting body weight was 40-41 grams. Animals were thereafter treated once daily with two separate s.c. injections (5 ml_/kg of each injection) from day 0 to day 27. The first injection was with vehicle 1 (25 mM phosphate, 125 mM sodium chloride buffer, pH 7.4) or GLP-1 analogue liraglutide (20 nmol/kg). The second injection was with vehicle 2 (25 mM phosphate, 205 mM D-Mannitol, pH 7.5) or GIP agonist (30 and/or 300 nmol/kg). The GIP agonist was only dosed every third day of the study (starting on day 0). On other days, GIP agonist was replaced with vehicle 2. The daily injections were given in the morning (at 9.00-10.00). Body weight was determined daily throughout the study. Changes in body weight during the study (delta Δ body weight=body weight at each study day−body weight at day 0. Data are means±SEM) are shown in FIG. 4 A (Compound 10 and 12), B (Compound 17), C (Compound 18), D (compound 35) and E (Compound 41).

Statistical analyses were performed for using Graph Pad Prism version 5. The change in body weight of liraglutide-treated mice was compared with mice co-administered liraglutide and GIP agonist by two-way ANOVA followed by Bonferroni posttests. $P<0.05$ was considered statistically significant (illustrated with lines below the body weight curves). The change in body weight of vehicle-treated control mice was compared with compound-treated mice by two-way ANOVA followed by Bonferroni posttests; *$p<0.001$ vs. vehicle. Statistical differences vs vehicle are shown for day 27 (FIG. 4** A-E).

---

SEQUENCE LISTING

```
<160> NUMBER OF SEQ ID NOS: 88

<210> SEQ ID NO 1
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 1

Tyr Ala Glu Gly Thr Phe Ile Ser Asp Tyr Ser Ile Glu Leu Asp Lys
1               5                   10                  15

Lys His Gln Gln Asp Phe Val Asn Trp Leu Leu Ala Gln Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Lys(Hexadecanoyl-isoGlu)

<400> SEQUENCE: 2

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Gly Pro Ser
            20                  25                  30

Ser Gly Ala Pro Pro Pro Ser
        35

<210> SEQ ID NO 3
<211> LENGTH: 39
```

```
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 3

Tyr Ala Glu Gly Thr Phe Ile Ser Asp Tyr Ser Ile Glu Leu Glu Lys
1               5                   10                  15

Lys His Gln Gln Asp Phe Val Asn Trp Leu Leu Ala Gln Gly Pro Ser
            20                  25                  30

Ser Gly Ala Pro Pro Pro Ser
            35

<210> SEQ ID NO 4
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (40)..(40)
<223> OTHER INFORMATION: Lys((19-carboxy-nonadecanoyl)-isoGlu-Peg3-Peg3)

<400> SEQUENCE: 4

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Gly Pro Ser
            20                  25                  30

Ser Gly Ala Pro Pro Pro Ser Lys
            35                  40

<210> SEQ ID NO 5
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (40)..(40)
<223> OTHER INFORMATION: Lys(Hexadecanoyl-isoGlu)

<400> SEQUENCE: 5

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Gly Pro Ser
            20                  25                  30

Ser Gly Ala Pro Pro Pro Ser Lys
            35                  40
```

```
<210> SEQ ID NO 6
<211> LENGTH: 30
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (30)..(30)
<223> OTHER INFORMATION: Lys(Hexadecanoyl-isoGlu)

<400> SEQUENCE: 6

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Lys
            20                  25                  30

<210> SEQ ID NO 7
<211> LENGTH: 32
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (32)..(32)
<223> OTHER INFORMATION: Lys(Hexadecanoyl-isoGlu)

<400> SEQUENCE: 7

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Lys Gly Lys
            20                  25                  30

<210> SEQ ID NO 8
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 8

Tyr Ala Glu Gly Thr Phe Ile Ser Asp Tyr Ser Ile Glu Leu Asp Lys
1               5                   10                  15

Lys His Gln Gln Asp Phe Val Asn Tyr Leu Leu Ala Gln Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial sequence
```

```
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 9

Tyr Ala Glu Gly Thr Phe Ile Ser Asp Tyr Ser Ile Glu Leu Asp Lys
1               5                   10                  15

Lys His Gln Gln Asp Phe Val Asn Trp Leu Leu Ala Gln Gly Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 10

Tyr Ala Glu Gly Thr Phe Ile Ser Asp Tyr Ser Ile Glu Leu Asp Lys
1               5                   10                  15

Lys Ala Ala Gln Asp Phe Val Asn Trp Leu Leu Ala Gln Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 11

Tyr Ala Glu Gly Thr Phe Ile Ser Asp Tyr Ser Ile Glu Leu Glu Lys
1               5                   10                  15

Lys Ala Ala Lys Glu Phe Val Asn Trp Leu Leu Ala Gln Gly Pro Ser
            20                  25                  30

Ser Gly Ala Pro Pro Pro Ser
        35

<210> SEQ ID NO 12
<211> LENGTH: 39
```

```
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 12

Tyr Ala Glu Gly Thr Phe Ile Ser Asp Tyr Ser Ile Glu Leu Glu Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 13
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (40)..(40)
<223> OTHER INFORMATION: Lys((19-carboxy-nonadecanoyl)-isoGlu-Peg3-Peg3)

<400> SEQUENCE: 13

Tyr Ala Glu Gly Thr Phe Ile Ser Asp Tyr Ser Ile Glu Leu Glu Lys
1               5                   10                  15

Ile Ala Gln Arg Ala Phe Val Glu Trp Leu Leu Ala Gln Gly Pro Ser
            20                  25                  30

Ser Gly Ala Pro Pro Pro Ser Lys
        35                  40

<210> SEQ ID NO 14
<211> LENGTH: 30
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (30)..(30)
<223> OTHER INFORMATION: Lys((19-carboxy-nonadecanoyl)-isoGlu-Peg3-Peg3)

<400> SEQUENCE: 14

Tyr Ala Glu Gly Thr Phe Ile Ser Asp Tyr Ser Ile Glu Leu Glu Lys
1               5                   10                  15

Ile Ala Gln Arg Ala Phe Val Glu Trp Leu Leu Ala Gln Lys
            20                  25                  30

<210> SEQ ID NO 15
<211> LENGTH: 38
<212> TYPE: PRT
```

```
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 15

Tyr Ala Glu Gly Thr Phe Ile Ser Asp Tyr Ser Ile Glu Leu Asp Lys
1               5                   10                  15

Lys Ala Ala Gln Asp Phe Val Asn Trp Leu Leu Ala Gly Pro Ser Ser
            20                  25                  30

Gly Ala Pro Pro Pro Ser
        35

<210> SEQ ID NO 16
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (39)..(39)
<223> OTHER INFORMATION: Lys((19-carboxy-nonadecanoyl)-isoGlu-Peg3-Peg3)

<400> SEQUENCE: 16

Tyr Ala Glu Gly Thr Phe Ile Ser Asp Tyr Ser Ile Glu Leu Asp Lys
1               5                   10                  15

Ile Ala Ala Gln Asp Phe Val Asn Trp Leu Leu Ala Gly Pro Ser Ser
            20                  25                  30

Gly Ala Pro Pro Pro Ser Lys
        35

<210> SEQ ID NO 17
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 17

Tyr Ala Glu Gly Thr Phe Ile Ser Asp Tyr Ser Ile Glu Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 18
```

```
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 18

Tyr Ala Glu Gly Thr Phe Ile Ser Asp Tyr Ser Ile Glu Leu Asp Lys
1               5                   10                  15

Lys Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-((Piperazine-1-
      yl)-acetyl)-Peg3-Peg3)

<400> SEQUENCE: 19

Tyr Ala Glu Gly Thr Phe Ile Ser Asp Tyr Ser Ile Glu Leu Asp Lys
1               5                   10                  15

Lys Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-((Piperazine-1-
      yl)-acetyl)-Peg3-Peg3)

<400> SEQUENCE: 20

Tyr Ala Glu Gly Thr Phe Ile Ser Asp Tyr Ser Ile Glu Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
```

<210> SEQ ID NO 21
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-((Piperazine-1-yl)-acetyl)-Peg3-Peg3)

<400> SEQUENCE: 21

Tyr Ala Glu Gly Thr Phe Ile Ser Asp Tyr Ser Ile Glu Leu Asp Lys
1               5                   10                  15

Lys Ala Gln Lys Glu Phe Val Glu Trp Leu Leu Ala Ala Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 22

Tyr Ala Glu Gly Thr Phe Ile Ser Asp Tyr Ser Ile Glu Leu Asp Lys
1               5                   10                  15

Lys Ala Gln Lys Glu Phe Val Glu Trp Leu Leu Ala Ala Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (39)..(39)
<223> OTHER INFORMATION: Lys((19-carboxy-nonadecanoyl)-isoGlu-Peg3-Peg3)

<400> SEQUENCE: 23

Tyr Ala Glu Gly Thr Phe Ile Ser Asp Tyr Ser Ile Glu Leu Asp Lys
1               5                   10                  15

Ile Ala Gln Arg Ala Phe Ile Glu Trp Leu Leu Ala Gly Pro Ser Ser

Gly Ala Pro Pro Pro Ser Lys
        35

<210> SEQ ID NO 24
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (39)..(39)
<223> OTHER INFORMATION: Lys((19-carboxy-nonadecanoyl)-isoGlu-Peg3-Peg3)

<400> SEQUENCE: 24

Tyr Ala Glu Gly Thr Phe Ile Ser Asp Tyr Ser Ile Glu Leu Asp Lys
1               5                   10                  15

Ile Ala Gln Lys Glu Phe Ile Glu Trp Leu Leu Ala Gly Pro Ser Ser
            20                  25                  30

Gly Ala Pro Pro Pro Ser Lys
        35

<210> SEQ ID NO 25
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (39)..(39)
<223> OTHER INFORMATION: Lys((19-carboxy-nonadecanoyl)-isoGlu-Peg3-Peg3)

<400> SEQUENCE: 25

Tyr Ala Glu Gly Thr Phe Ile Ser Asp Tyr Ser Ile Glu Leu Asp Lys
1               5                   10                  15

Ile Ala Ala Gln Asp Phe Ile Glu Trp Leu Leu Ala Gly Pro Ser Ser
            20                  25                  30

Gly Ala Pro Pro Pro Ser Lys
        35

<210> SEQ ID NO 26
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (39)..(39)
<223> OTHER INFORMATION: Lys((19-Carboxy-nonadecanoyl)-((Piperazine-1-
      yl)-acetyl)-Peg3-Peg3)

<400> SEQUENCE: 26

Tyr Ala Glu Gly Thr Phe Ile Ser Asp Tyr Ser Ile Glu Leu Asp Lys

```
1               5                   10                  15

Ile Ala Ala Gln Asp Phe Ile Glu Trp Leu Leu Ala Gly Pro Ser Ser
                20                  25                  30

Gly Ala Pro Pro Pro Ser Lys
        35

<210> SEQ ID NO 27
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (39)..(39)
<223> OTHER INFORMATION: Lys((19-carboxy-nonadecanoyl)-isoGlu-Peg3-Peg3)

<400> SEQUENCE: 27

Tyr Ala Glu Gly Thr Phe Ile Ser Asp Tyr Ser Ile Glu Leu Asp Lys
1               5                   10                  15

Ile Ala Ala Gln Asp Phe Val Glu Trp Leu Leu Ala Gly Pro Ser Ser
                20                  25                  30

Gly Ala Pro Pro Pro Ser Lys
        35

<210> SEQ ID NO 28
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (40)..(40)
<223> OTHER INFORMATION: Lys((19-carboxy-nonadecanoyl)-isoGlu-Peg3-Peg3)

<400> SEQUENCE: 28

Tyr Ala Glu Gly Thr Phe Ile Ser Asp Tyr Ser Ile Glu Leu Asp Lys
1               5                   10                  15

Ile Ala Gln Arg Ala Phe Ile Glu Trp Leu Leu Ala Gln Gly Pro Ser
                20                  25                  30

Ser Gly Ala Pro Pro Pro Ser Lys
        35                  40

<210> SEQ ID NO 29
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 29
```

```
Tyr Ala Glu Gly Thr Phe Ile Ser Asp Tyr Ser Ile Glu Leu Asp Lys
1               5                   10                  15

Lys Ala Ala Gln Ala Phe Val Asn Trp Leu Leu Ala Gly Pro Ser Ser
            20                  25                  30

Gly Ala Pro Pro Pro Ser
        35

<210> SEQ ID NO 30
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 30

Tyr Ala Glu Gly Thr Phe Ile Ser Asp Tyr Ser Ile Glu Leu Asp Lys
1               5                   10                  15

Lys Ala Ala Gln Asp Phe Val Asn Trp Leu Leu Ala Ala Gly Pro Ser
            20                  25                  30

Ser Gly Ala Pro Pro Pro Ser
        35

<210> SEQ ID NO 31
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 31

Tyr Ala Glu Gly Thr Phe Ile Ser Asp Tyr Ser Ile Glu Leu Asp Lys
1               5                   10                  15

Lys Ala Ala Gln Asp Phe Ile Asn Trp Leu Leu Ala Gly Pro Ser Ser
            20                  25                  30

Gly Ala Pro Pro Pro Ser
        35

<210> SEQ ID NO 32
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)
```

```
<400> SEQUENCE: 32

Tyr Ala Glu Gly Thr Phe Ile Ser Asp Tyr Ser Ile Glu Leu Asp Lys
1               5                   10                  15

Lys Ala Ala Gln Asp Phe Ile Glu Trp Leu Leu Ala Gly Pro Ser Ser
            20                  25                  30

Gly Ala Pro Pro Ser
        35

<210> SEQ ID NO 33
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-((Piperazine-1-
      yl)-acetyl)-Peg3-Peg3)

<400> SEQUENCE: 33

Tyr Ala Glu Gly Thr Phe Ile Ser Asp Tyr Ser Ile Glu Leu Asp Lys
1               5                   10                  15

Lys Ala Ala Gln Asp Phe Ile Glu Trp Leu Leu Ala Gly Pro Ser Ser
            20                  25                  30

Gly Ala Pro Pro Ser
        35

<210> SEQ ID NO 34
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Lys((19-carboxy-nonadecanoyl)-isoGlu-Peg3-Peg3)

<400> SEQUENCE: 34

Tyr Ala Glu Gly Thr Phe Ile Ser Asp Tyr Ser Ile Glu Leu Asp Lys
1               5                   10                  15

Ile Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
```

```
<221> NAME/KEY: SITE
<222> LOCATION: (12)..(12)
<223> OTHER INFORMATION: Lys((19-carboxy-nonadecanoyl)-isoGlu-Peg3-Peg3)

<400> SEQUENCE: 35

Tyr Ala Glu Gly Thr Phe Ile Ser Asp Tyr Ser Lys Glu Leu Asp Lys
1               5                   10                  15

Ile Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 36

Tyr Xaa Glu Gly Thr Phe Ile Ser Asp Tyr Ser Ile Glu Leu Asp Lys
1               5                   10                  15

Lys Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: SITE
<222> LOCATION: (39)..(39)
<223> OTHER INFORMATION: Lys((19-Carboxy-nonadecanoyl)-((Piperazine-1-
      yl)-acetyl)-Peg3-Peg3)

<400> SEQUENCE: 37

Tyr Xaa Glu Gly Thr Phe Ile Ser Asp Tyr Ser Ile Glu Leu Asp Lys
1               5                   10                  15

Ile Ala Ala Gln Asp Phe Ile Glu Trp Leu Leu Ala Gly Pro Ser Ser
            20                  25                  30

Gly Ala Pro Pro Pro Ser Lys
        35

<210> SEQ ID NO 38
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
```

```
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 38

Tyr Ala Glu Gly Thr Phe Ile Ser Asp Tyr Ser Ile Glu Leu Asp Lys
1               5                   10                  15

Lys Ala Ala Gln Asp Phe Ile Glu Trp Leu Leu Ala Gln Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 39

Tyr Ala Glu Gly Thr Phe Ile Ser Asp Tyr Ser Ile Glu Leu Asp Lys
1               5                   10                  15

Lys Ala Ala Gln Asp Phe Ile Asn Trp Leu Leu Ala Gln Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-carboxy-nonadecanoyl)-isoGlu-Peg3-Peg3)

<400> SEQUENCE: 40

Tyr Ala Glu Gly Thr Phe Ile Ser Asp Tyr Ser Ile Glu Leu Asp Lys
1               5                   10                  15

Lys Ala Ala Gln Ala Phe Ile Glu Trp Leu Leu Ala Gln Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial sequence
<220> FEATURE:
<223> OTHER INFORMATION: Synthetic GIP analogue
```

```
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-((Piperazine-1-
      yl)-acetyl)-Peg3-Peg3)

<400> SEQUENCE: 41

Tyr Ala Glu Gly Thr Phe Ile Ser Asp Tyr Ser Ile Glu Leu Asp Lys
1               5                   10                  15

Lys Ala Ala Gln Ala Phe Ile Glu Trp Leu Leu Ala Gln Gly Pro Ser
            20                  25                  30

Ser Gly Ala Pro Pro Pro Ser
        35

<210> SEQ ID NO 42
<211> LENGTH: 42
<212> TYPE: PRT
<213> ORGANISM: Artificial sequence
<220> FEATURE:
<223> OTHER INFORMATION: Synthetic GIP analogue of general Formula I
<220> FEATURE:
<221> NAME/KEY: SITE
<222> LOCATION: (1)..(1)
<223> OTHER INFORMATION: Linked to R1, wherein R1 is H-, Ac or pGlu
<220> FEATURE:
<221> NAME/KEY: VARIANT
<222> LOCATION: (1)..(42)
<223> OTHER INFORMATION: The GIP analogue contains one and only one
      residue Psi; wherein Psi is a residue independently selected from
      Lys, Arg, Orn and Cys and wherein the side chain of said residue
      is conjugated to a lipophilic substituent
<220> FEATURE:
<221> NAME/KEY: VARIANT
<222> LOCATION: (2)..(2)
<223> OTHER INFORMATION: Xaa is Aib, Ala, D-Ala, Gly, Ser, N-Me-Ser,
      Ac3c, Ac4c or Ac5c
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (12)..(12)
<223> OTHER INFORMATION: Xaa is Lys, Psi or Ile; wherein Psi is a
      residue independently selected from Lys, Arg, Orn and Cys and
      wherein the side chain of said residue is conjugated to a
      lipophilic substituent
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Ser, Glu, Lys or Psi; wherein Psi is a
      residue independently selected from Lys, Arg, Orn and Cys and
      wherein the side chain of said residue is conjugated to a
      lipophilic substituent
<220> FEATURE:
<221> NAME/KEY: VARIANT
<222> LOCATION: (17)..(17)
<223> OTHER INFORMATION: Xaa is Ile, Lys, Gln, Arg or Psi; wherein Psi
      is a residue independently selected from Lys, Arg, Orn and Cys and
      wherein the side chain of said residue is conjugated to a
      lipophilic substituent
<220> FEATURE:
<221> NAME/KEY: VARIANT
```

```
<222> LOCATION: (18)..(18)
<223> OTHER INFORMATION: Xaa is His, Arg or Ala
<220> FEATURE:
<221> NAME/KEY: VARIANT
<222> LOCATION: (19)..(19)
<223> OTHER INFORMATION: Xaa is Gln, Lys, Ala or Glu
<220> FEATURE:
<221> NAME/KEY: VARIANT
<222> LOCATION: (20)..(20)
<223> OTHER INFORMATION: Xaa is Gln, Lys, Ala, His or Arg
<220> FEATURE:
<221> NAME/KEY: VARIANT
<222> LOCATION: (21)..(21)
<223> OTHER INFORMATION: Xaa is Ala, Leu, Asp or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Asn or Glu
<220> FEATURE:
<221> NAME/KEY: VARIANT
<222> LOCATION: (25)..(25)
<223> OTHER INFORMATION: Xaa is Tyr or Trp
<220> FEATURE:
<221> NAME/KEY: VARIANT
<222> LOCATION: (27)..(27)
<223> OTHER INFORMATION: Xaa is Leu, Glu, Ser, Lys or Val
<220> FEATURE:
<221> NAME/KEY: VARIANT
<222> LOCATION: (28)..(28)
<223> OTHER INFORMATION: Xaa is Ala, Ser or Arg
<220> FEATURE:
<221> NAME/KEY: VARIANT
<222> LOCATION: (29)..(29)
<223> OTHER INFORMATION: Xaa is Aib, Gly, Ala, Gln, Thr, Ser or Lys or
      is absent
<220> FEATURE:
<221> NAME/KEY: VARIANT
<222> LOCATION: (30)..(41)
<223> OTHER INFORMATION: Xaa, starting at pos. 30, is: Lys Gly (pos.
      30-31); Gly Pro Ser Ser Gly Ala Pro Pro Pro Ser; Gly Pro Ser Ser
      Gly Ala Pro Pro Ser; Pro Ser Ser Gly Ala Pro Pro Ser; Pro Ser
      Ser Gly Ala Pro Pro Ser; Gly Lys Lys Asn Asp Trp Lys His Asn lle
      Thr Gln; or absent.
<220> FEATURE:
<221> NAME/KEY: VARIANT
<222> LOCATION: (30)..(42)
<223> OTHER INFORMATION: Xaa is Psi (as defined in 'VARIANT' for
      positions 12, 16 and 17) or absent; This applies to positions 30,
      32, 38, 39, 40 or 42, dependent upon which chain of amino acids
      starts at pos. 30 as noted in the 'VARIANT' for positions 30-41
      (listed above).

<400> SEQUENCE: 42

Tyr Xaa Glu Gly Thr Phe Ile Ser Asp Xaa Xaa Xaa Glu Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 43
<211> LENGTH: 10
<212> TYPE: PRT
<213> ORGANISM: Artificial sequence
<220> FEATURE:
<223> OTHER INFORMATION: Synthetic sequence Y1 in SEQ ID NOs: 42, 50,
      87, & 89

<400> SEQUENCE: 43

Gly Pro Ser Ser Gly Ala Pro Pro Pro Ser
```

```
1               5                  10
```

<210> SEQ ID NO 44
<211> LENGTH: 9
<212> TYPE: PRT
<213> ORGANISM: Artificial sequence
<220> FEATURE:
<223> OTHER INFORMATION: Synthetic sequence Y1 in SEQ ID NOs: 42, 48,
      50, & 87 - 89

<400> SEQUENCE: 44

Gly Pro Ser Ser Gly Ala Pro Pro Ser
1               5

<210> SEQ ID NO 45
<211> LENGTH: 9
<212> TYPE: PRT
<213> ORGANISM: Artificial sequence
<220> FEATURE:
<223> OTHER INFORMATION: Synthetic sequence Y1 in SEQ ID NOs: 42, 48,
      50, & 87 - 89

<400> SEQUENCE: 45

Pro Ser Ser Gly Ala Pro Pro Pro Ser
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic sequence Y1 in SEQ ID NOs: 42, 48,
      50, & 87 - 89

<400> SEQUENCE: 46

Pro Ser Ser Gly Ala Pro Pro Ser
1               5

<210> SEQ ID NO 47
<211> LENGTH: 12
<212> TYPE: PRT
<213> ORGANISM: Artificial sequence
<220> FEATURE:
<223> OTHER INFORMATION: Synthetic sequence Y1 in SEQ ID NOs: 42, 48,
      50, & 87 - 89

<400> SEQUENCE: 47

Gly Lys Lys Asn Asp Trp Lys His Asn Ile Thr Gln
1               5                  10

<210> SEQ ID NO 48
<211> LENGTH: 42
<212> TYPE: PRT
<213> ORGANISM: Artificial sequence
<220> FEATURE:
<223> OTHER INFORMATION: Synthetic GIP analogue of general Formula II
<220> FEATURE:
<221> NAME/KEY: SITE
<222> LOCATION: (1)..(1)
<223> OTHER INFORMATION: Linked to R1, wherein R1 is H-, Ac or pGlu
<220> FEATURE:
<221> NAME/KEY: VARIANT
<222> LOCATION: (1)..(42)
<223> OTHER INFORMATION: The GIP analogue contains one and only one
      residue Psi; wherein Psi is a Lys residue wherein the side chain
      of said Lys residue is conjugated to a lipophilic substituent
<220> FEATURE:
<221> NAME/KEY: VARIANT
<222> LOCATION: (2)..(2)
<223> OTHER INFORMATION: Xaa is Aib, Ala, D-Ala, Gly

```
<220> FEATURE:
<221> NAME/KEY: VARIANT
<222> LOCATION: (12)..(12)
<223> OTHER INFORMATION: Xaa is Lys, Psi or Ile; wherein Psi is a Lys
      residue wherein the side chain of said Lys residue is conjugated
      to a lipophilic substituent
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Ser, Glu, Lys or Psi; wherein Psi is a
      Lys residue wherein the side chain of said Lys residue is
      conjugated to a lipophilic substituent
<220> FEATURE:
<221> NAME/KEY: VARIANT
<222> LOCATION: (17)..(17)
<223> OTHER INFORMATION: Xaa is Ile, Lys, Gln, Arg or Psi; wherein Psi
      is a Lys residue wherein the side chain of said Lys residue is
      conjugated to a lipophilic substituent
<220> FEATURE:
<221> NAME/KEY: VARIANT
<222> LOCATION: (18)..(18)
<223> OTHER INFORMATION: Xaa is His, Arg or Ala
<220> FEATURE:
<221> NAME/KEY: VARIANT
<222> LOCATION: (19)..(19)
<223> OTHER INFORMATION: Xaa is Gln or Ala
<220> FEATURE:
<221> NAME/KEY: VARIANT
<222> LOCATION: (20)..(20)
<223> OTHER INFORMATION: Xaa is Gln, Lys, Ala, His or Arg
<220> FEATURE:
<221> NAME/KEY: VARIANT
<222> LOCATION: (21)..(21)
<223> OTHER INFORMATION: Xaa is Ala, Asp or Glu
<220> FEATURE:
<221> NAME/KEY: VARIANT
<222> LOCATION: (23)..(23)
<223> OTHER INFORMATION: Xaa is Ile or Val
<220> FEATURE:
<221> NAME/KEY: VARIANT
<222> LOCATION: (24)..(24)
<223> OTHER INFORMATION: Xaa is Asn or Glu
<220> FEATURE:
<221> NAME/KEY: VARIANT
<222> LOCATION: (25)..(25)
<223> OTHER INFORMATION: Xaa is Tyr or Trp
<220> FEATURE:
<221> NAME/KEY: VARIANT
<222> LOCATION: (27)..(27)
<223> OTHER INFORMATION: Xaa is Leu, Glu, Ser, Lys or Val
<220> FEATURE:
<221> NAME/KEY: VARIANT
<222> LOCATION: (28)..(28)
<223> OTHER INFORMATION: Xaa is Ala, Ser or Arg
<220> FEATURE:
<221> NAME/KEY: VARIANT
<222> LOCATION: (29)..(29)
<223> OTHER INFORMATION: Xaa is Aib, Gly, Ala, Gln, Thr, Ser or Lys or
      is absent
<220> FEATURE:
<221> NAME/KEY: VARIANT
<222> LOCATION: (30)..(41)
<223> OTHER INFORMATION: Xaa, starting at position 30, is: Lys Gly (pos.
      30-31); Gly Pro Ser Ser Gly Ala Pro Pro Pro; Gly Pro Ser Ser Gly
      Ala Pro Pro Ser; Pro Ser Ser Gly Ala Pro Pro Pro Ser; Pro Ser Ser
      Gly Ala Pro Pro Ser; Gly Lys Lys Asn Asp Trp Lys His Asn Ile Thr
      Gln; or absent.
<220> FEATURE:
<221> NAME/KEY: VARIANT
<222> LOCATION: (30)..(42)
<223> OTHER INFORMATION: Xaa is Psi (as defined in 'VARIANT' for
      positions 12, 16 and 17) or absent; This applies to positions 30,
      32, 38, 39, or 42, dependent upon which chain of amino acids
      starts at position 30 as noted in the 'VARIANT' for positions
      30-41 (listed above).
```

<400> SEQUENCE: 48

Tyr Xaa Glu Gly Thr Phe Ile Ser Asp Tyr Ser Xaa Glu Leu Xaa Xaa
1               5                   10                  15

Xaa Xaa Xaa Xaa Xaa Phe Xaa Xaa Xaa Leu Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 49
<211> LENGTH: 9
<212> TYPE: PRT
<213> ORGANISM: Artificial sequence
<220> FEATURE:
<223> OTHER INFORMATION: Synthetic sequence Y1 in SEQ ID NOs: 48 & 88

<400> SEQUENCE: 49

Gly Pro Ser Ser Gly Ala Pro Pro Pro
1               5

<210> SEQ ID NO 50
<211> LENGTH: 42
<212> TYPE: PRT
<213> ORGANISM: Artificial sequence
<220> FEATURE:
<223> OTHER INFORMATION: Synthetic GIP analogue of general Formula III
<220> FEATURE:
<221> NAME/KEY: VARIANT
<222> LOCATION: (1)..(42)
<223> OTHER INFORMATION: The GIP analogue contains one and only one
      residue Psi; wherein Psi is a residue independently selected from
      Lys, Arg, Orn and Cys and wherein the side chain of said residue
      is conjugated to a lipophilic substituent
<220> FEATURE:
<221> NAME/KEY: SITE
<222> LOCATION: (1)..(1)
<223> OTHER INFORMATION: Linked to R1, wherein R1 is H-, Ac or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys or Psi; wherein Psi is a residue
      independently selected from Lys, Arg, Orn and Cys and wherein the
      side chain of said residue is conjugated to a lipophilic
      substituent
<220> FEATURE:
<221> NAME/KEY: VARIANT
<222> LOCATION: (17)..(17)
<223> OTHER INFORMATION: Xaa is Ile or Psi; wherein Psi is a residue
      independently selected from Lys, Arg, Orn and Cys and wherein the
      side chain of said residue is conjugated to a lipophilic
      substituent
<220> FEATURE:
<221> NAME/KEY: VARIANT
<222> LOCATION: (18)..(18)
<223> OTHER INFORMATION: Xaa is His or Ala
<220> FEATURE:
<221> NAME/KEY: VARIANT
<222> LOCATION: (19)..(19)
<223> OTHER INFORMATION: Xaa is Gln or Ala
<220> FEATURE:
<221> NAME/KEY: VARIANT
<222> LOCATION: (20)..(20)
<223> OTHER INFORMATION: Xaa is Gln, Lys or Arg
<220> FEATURE:
<221> NAME/KEY: VARIANT

```
<222> LOCATION: (21)..(21)
<223> OTHER INFORMATION: Xaa is Ala, Asp or Glu
<220> FEATURE:
<221> NAME/KEY: VARIANT
<222> LOCATION: (24)..(24)
<223> OTHER INFORMATION: Xaa is Asn or Glu
<220> FEATURE:
<221> NAME/KEY: VARIANT
<222> LOCATION: (25)..(25)
<223> OTHER INFORMATION: Xaa is Tyr or Trp
<220> FEATURE:
<221> NAME/KEY: VARIANT
<222> LOCATION: (29)..(29)
<223> OTHER INFORMATION: Xaa is Gln or is absent
<220> FEATURE:
<221> NAME/KEY: VARIANT
<222> LOCATION: (30)..(41)
<223> OTHER INFORMATION: Xaa, starting at pos. 30, is: Lys Gly (pos.
      30-31); Gly Pro Ser Ser Gly Ala Pro Pro Pro Ser; Gly Pro Ser Ser
      Gly Ala Pro Pro Ser; Pro Ser Ser Gly Ala Pro Pro Pro Ser; Pro Ser
      Ser Gly Ala Pro Pro Ser; Gly Lys Lys Asn Asp Trp Lys His Asn lle
      Thr Gln; or absent.
<220> FEATURE:
<221> NAME/KEY: VARIANT
<222> LOCATION: (30)..(42)
<223> OTHER INFORMATION: Xaa is Psi (as defined in 'VARIANT' for
      positions 16 and 17) or absent; This applies to positions 30, 32,
      38, 39, 40 or 42, dependent upon which chain of amino acids starts
      at pos. 30 as noted in the 'VARIANT' for positions 30-41 (listed
      above).

<400> SEQUENCE: 50

Tyr Ala Glu Gly Thr Phe Ile Ser Asp Tyr Ser Ile Glu Leu Xaa Xaa
1               5                   10                  15

Xaa Xaa Xaa Xaa Xaa Phe Val Xaa Xaa Leu Leu Ala Xaa Xaa Xaa Xaa
            20                  25                  30

Xaa Xaa Xaa Xaa Xaa Xaa Xaa Xaa Xaa Xaa
        35                  40

<210> SEQ ID NO 51
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 51

Tyr Ala Glu Gly Thr Phe Ile Ser Asp Tyr Ser Ile Glu Leu Asp Lys
1               5                   10                  15

Xaa His Gln Gln Asp Phe Val Asn Trp Leu Leu Ala Gln Gly Pro Ser
            20                  25                  30

Ser Gly Ala Pro Pro Pro Ser
        35

<210> SEQ ID NO 52
<211> LENGTH: 39
<212> TYPE: PRT
<213> ORGANISM: Artificial sequence
<220> FEATURE:
<223> OTHER INFORMATION: Synthetic GIP analogue
```

```
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (16)..(16)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 52

Tyr Ala Glu Gly Thr Phe Ile Ser Asp Tyr Ser Ile Glu Leu Asp Xaa
1               5                   10                  15

Ile His Gln Gln Asp Phe Val Asn Trp Leu Leu Ala Gln Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 53

Tyr Ala Glu Gly Thr Phe Ile Ser Asp Tyr Ser Ile Glu Leu Glu Lys
1               5                   10                  15

Xaa His Gln Gln Asp Phe Val Asn Trp Leu Leu Ala Gln Gly Pro Ser
            20                  25                  30

Ser Gly Ala Pro Pro Pro Ser
        35

<210> SEQ ID NO 54
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (40)..(40)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 54

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Gly Pro Ser
            20                  25                  30
```

```
Ser Gly Ala Pro Pro Ser Xaa
        35                  40

<210> SEQ ID NO 55
<211> LENGTH: 30
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(30)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 55

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Xaa
            20                  25                  30

<210> SEQ ID NO 56
<211> LENGTH: 32
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (32)..(32)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 56

Tyr Ala Glu Gly Thr Phe Ile Ser Asp Tyr Ser Ile Glu Leu Asp Lys
1               5                   10                  15

Ile His Gln Gln Asp Phe Val Asn Trp Leu Leu Ala Gln Lys Gly Xaa
            20                  25                  30

<210> SEQ ID NO 57
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 57
```

Tyr Ala Glu Gly Thr Phe Ile Ser Asp Tyr Ser Ile Glu Leu Asp Lys
1               5                   10                  15

Xaa His Gln Gln Asp Phe Val Asn Tyr Leu Leu Ala Gln Gly Pro Ser
            20                  25                  30

Ser Gly Ala Pro Pro Ser
        35

<210> SEQ ID NO 58
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 58

Tyr Ala Glu Gly Thr Phe Ile Ser Asp Tyr Ser Ile Glu Leu Asp Lys
1               5                   10                  15

Xaa His Gln Gln Asp Phe Val Asn Trp Leu Leu Ala Gln Gly Pro Ser
            20                  25                  30

Ser Gly Ala Pro Pro Ser
        35

<210> SEQ ID NO 59
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 59

Tyr Ala Glu Gly Thr Phe Ile Ser Asp Tyr Ser Ile Glu Leu Asp Lys
1               5                   10                  15

Xaa Ala Ala Gln Asp Phe Val Asn Trp Leu Leu Ala Gln Gly Pro Ser
            20                  25                  30

Ser Gly Ala Pro Pro Ser
        35

<210> SEQ ID NO 60
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)

```
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 60

Tyr Ala Glu Gly Thr Phe Ile Ser Asp Tyr Ser Ile Glu Leu Glu Lys
1               5                   10                  15

Xaa Ala Ala Lys Glu Phe Val Asn Trp Leu Leu Ala Gln Gly Pro Ser
            20                  25                  30

Ser Gly Ala Pro Pro Pro Ser
        35

<210> SEQ ID NO 61
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 61

Tyr Ala Glu Gly Thr Phe Ile Ser Asp Tyr Ser Ile Glu Leu Glu Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 62
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (40)..(40)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 62

Tyr Ala Glu Gly Thr Phe Ile Ser Asp Tyr Ser Ile Glu Leu Glu Lys
1               5                   10                  15

Ile Ala Gln Arg Ala Phe Val Glu Trp Leu Leu Ala Gln Gly Pro Ser
            20                  25                  30

Ser Gly Ala Pro Pro Pro Ser Xaa
        35                  40
```

```
<210> SEQ ID NO 63
<211> LENGTH: 30
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(30)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 63

Tyr Ala Glu Gly Thr Phe Ile Ser Asp Tyr Ser Ile Glu Leu Glu Lys
1               5                   10                  15

Ile Ala Gln Arg Ala Phe Val Glu Trp Leu Leu Ala Gln Xaa
            20                  25                  30

<210> SEQ ID NO 64
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 64

Tyr Ala Glu Gly Thr Phe Ile Ser Asp Tyr Ser Ile Glu Leu Asp Lys
1               5                   10                  15

Xaa Ala Ala Gln Asp Phe Val Asn Trp Leu Leu Ala Gly Pro Ser Ser
            20                  25                  30

Gly Ala Pro Pro Pro Ser
            35

<210> SEQ ID NO 65
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (39)..(39)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 65
```

```
Tyr Ala Glu Gly Thr Phe Ile Ser Asp Tyr Ser Ile Glu Leu Asp Lys
1               5                   10                  15

Ile Ala Ala Gln Asp Phe Val Asn Trp Leu Leu Ala Gly Pro Ser Ser
            20                  25                  30

Gly Ala Pro Pro Pro Ser Xaa
        35

<210> SEQ ID NO 66
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 66

Tyr Ala Glu Gly Thr Phe Ile Ser Asp Tyr Ser Ile Glu Leu Asp Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 67
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 67

Tyr Ala Glu Gly Thr Phe Ile Ser Asp Tyr Ser Ile Glu Leu Asp Lys
1               5                   10                  15

Xaa Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 68
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
```

```
<223> OTHER INFORMATION: Aib
<220> FEATURE:
<221> NAME/KEY: VARIANT
<222> LOCATION: (40)..(40)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 68

Tyr Ala Glu Gly Thr Phe Ile Ser Asp Tyr Ser Ile Glu Leu Asp Lys
1               5                   10                  15

Ile Ala Gln Arg Ala Phe Ile Glu Trp Leu Leu Ala Gly Pro Ser Ser
            20                  25                  30

Gly Ala Pro Pro Pro Ser Lys Xaa
        35                  40

<210> SEQ ID NO 69
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (40)..(40)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 69

Tyr Ala Glu Gly Thr Phe Ile Ser Asp Tyr Ser Ile Glu Leu Asp Lys
1               5                   10                  15

Ile Ala Gln Lys Glu Phe Ile Glu Trp Leu Leu Ala Gly Pro Ser Ser
            20                  25                  30

Gly Ala Pro Pro Pro Ser Lys Xaa
        35                  40

<210> SEQ ID NO 70
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (40)..(40)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 70

Tyr Ala Glu Gly Thr Phe Ile Ser Asp Tyr Ser Ile Glu Leu Asp Lys
1               5                   10                  15

Ile Ala Ala Gln Asp Phe Ile Glu Trp Leu Leu Ala Gly Pro Ser Ser
            20                  25                  30

Gly Ala Pro Pro Pro Ser Lys Xaa
        35                  40
```

```
<210> SEQ ID NO 71
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (40)..(40)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 71

Tyr Ala Glu Gly Thr Phe Ile Ser Asp Tyr Ser Ile Glu Leu Asp Lys
1               5                   10                  15

Ile Ala Ala Gln Asp Phe Val Glu Trp Leu Leu Ala Gly Pro Ser Ser
            20                  25                  30

Gly Ala Pro Pro Pro Ser Lys Xaa
        35                  40

<210> SEQ ID NO 72
<211> LENGTH: 41
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (41)..(41)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 72

Tyr Ala Glu Gly Thr Phe Ile Ser Asp Tyr Ser Ile Glu Leu Asp Lys
1               5                   10                  15

Ile Ala Gln Arg Ala Phe Ile Glu Trp Leu Leu Ala Gln Gly Pro Ser
            20                  25                  30

Ser Gly Ala Pro Pro Pro Ser Lys Xaa
        35                  40

<210> SEQ ID NO 73
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent
```

-continued

```
<400> SEQUENCE: 73

Tyr Ala Glu Gly Thr Phe Ile Ser Asp Tyr Ser Ile Glu Leu Asp Lys
1               5                   10                  15

Xaa Ala Ala Gln Ala Phe Val Asn Trp Leu Leu Ala Gly Pro Ser Ser
            20                  25                  30

Gly Ala Pro Pro Pro Ser
        35

<210> SEQ ID NO 74
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 74

Tyr Ala Glu Gly Thr Phe Ile Ser Asp Tyr Ser Ile Glu Leu Asp Lys
1               5                   10                  15

Xaa Ala Ala Gln Asp Phe Val Asn Trp Leu Leu Ala Ala Gly Pro Ser
            20                  25                  30

Ser Gly Ala Pro Pro Pro Ser
        35

<210> SEQ ID NO 75
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 75

Tyr Ala Glu Gly Thr Phe Ile Ser Asp Tyr Ser Ile Glu Leu Asp Lys
1               5                   10                  15

Xaa Ala Ala Gln Asp Phe Ile Asn Trp Leu Leu Ala Gly Pro Ser Ser
            20                  25                  30

Gly Ala Pro Pro Pro Ser
        35

<210> SEQ ID NO 76
<211> LENGTH: 38
<212> TYPE: PRT
<213> ORGANISM: Artificial sequence
<220> FEATURE:
<223> OTHER INFORMATION: Synthetic GIP analogue
```

```
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 76

Tyr Ala Glu Gly Thr Phe Ile Ser Asp Tyr Ser Ile Glu Leu Asp Lys
1               5                   10                  15

Xaa Ala Ala Gln Asp Phe Ile Glu Trp Leu Leu Ala Gly Pro Ser Ser
            20                  25                  30

Gly Ala Pro Pro Pro Ser
        35

<210> SEQ ID NO 77
<211> LENGTH: 38
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 77

Tyr Ala Glu Gly Thr Phe Ile Ser Asp Tyr Ser Ile Glu Leu Asp Lys
1               5                   10                  15

Xaa Ala Ala Gln Asp Phe Ile Glu Trp Leu Leu Ala Gly Pro Ser Ser
            20                  25                  30

Gly Ala Pro Pro Pro Ser
        35

<210> SEQ ID NO 78
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 78

Tyr Ala Glu Gly Thr Phe Ile Ser Asp Tyr Ser Ile Glu Leu Asp Lys
1               5                   10                  15

Xaa Ile Ala Gln Arg Ala Phe Ile Glu Trp Leu Leu Ala Gln Gly Pro
            20                  25                  30
```

Ser Ser Gly Ala Pro Pro Ser
        35              40

<210> SEQ ID NO 79
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (12)..(12)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 79

Tyr Ala Glu Gly Thr Phe Ile Ser Asp Tyr Ser Xaa Glu Leu Asp Lys
1               5                   10                  15

Ile Ala Gln Arg Ala Phe Ile Glu Trp Leu Leu Ala Gln Gly Pro Ser
            20                  25                  30

Ser Gly Ala Pro Pro Ser
        35

<210> SEQ ID NO 80
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 80

Tyr Xaa Glu Gly Thr Phe Ile Ser Asp Tyr Ser Ile Glu Leu Asp Lys
1               5                   10                  15

Xaa Ala Gln Arg Ala Phe Ile Glu Trp Leu Leu Ala Gln Gly Pro Ser
            20                  25                  30

Ser Gly Ala Pro Pro Ser
        35

<210> SEQ ID NO 81
<211> LENGTH: 40
<212> TYPE: PRT
<213> ORGANISM: Artificial sequence
<220> FEATURE:
<223> OTHER INFORMATION: Synthetic GIP analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: SITE
<222> LOCATION: (40)..(40)
<223> OTHER INFORMATION: Xaa is Psi, wherein Psi is a residue

```
            independently selected from Lys, Arg, Orn and Cys and wherein the
            side chain of said residue is conjugated to a lipophilic
            substituent

<400> SEQUENCE: 81

Tyr Xaa Glu Gly Thr Phe Ile Ser Asp Tyr Ser Ile Glu Leu Asp Lys
 1               5                  10                  15

Ile Ala Ala Gln Asp Phe Ile Glu Trp Leu Leu Ala Gly Pro Ser Ser
            20                  25                  30

Gly Ala Pro Pro Pro Ser Lys Xaa
         35                  40

<210> SEQ ID NO 82
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 82

Tyr Ala Glu Gly Thr Phe Ile Ser Asp Tyr Ser Ile Glu Leu Asp Lys
 1               5                  10                  15

Xaa Ala Ala Gln Asp Phe Ile Glu Trp Leu Leu Ala Gln Gly Pro Ser
            20                  25                  30

Ser Gly Ala Pro Pro Pro Ser
         35

<210> SEQ ID NO 83
<211> LENGTH: 39
<212> TYPE: PRT
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 83

Tyr Ala Glu Gly Thr Phe Ile Ser Asp Tyr Ser Ile Glu Leu Asp Lys
 1               5                  10                  15

Xaa Ala Ala Gln Asp Phe Ile Asn Trp Leu Leu Ala Gln Gly Pro Ser
            20                  25                  30

Ser Gly Ala Pro Pro Pro Ser
         35

<210> SEQ ID NO 84
<211> LENGTH: 39
<212> TYPE: PRT
```

```
<213> ORGANISM: Artificial sequence
<220> FEATURE:
<223> OTHER INFORMATION: Synthetic GIP analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue
      independently selected from Lys, Arg, Orn and Cys and wherein the
      side chain of said residue is conjugated to a lipophilic
      substituent

<400> SEQUENCE: 84

Tyr Ala Glu Gly Thr Phe Ile Ser Asp Tyr Ser Ile Glu Leu Asp Lys
1               5                   10                  15

Xaa Ala Ala Gln Ala Phe Ile Glu Trp Leu Leu Ala Gln Gly Pro Ser
            20                  25                  30

Ser Gly Ala Pro Pro Pro Ser
        35

<210> SEQ ID NO 85
<211> LENGTH: 6
<212> TYPE: PRT
<213> ORGANISM: Artificial sequence
<220> FEATURE:
<223> OTHER INFORMATION: Synthetic linker

<400> SEQUENCE: 85

Gly Ser Gly Ser Gly Gly
1               5

<210> SEQ ID NO 86
<211> LENGTH: 43
<212> TYPE: PRT
<213> ORGANISM: Artificial sequence
<220> FEATURE:
<223> OTHER INFORMATION: Synthetic GIP analogue of general Formula I
<220> FEATURE:
<221> NAME/KEY: VARIANT
<222> LOCATION: (1)..(1)
<223> OTHER INFORMATION: Xaa is H-, Ac or pGlu
<220> FEATURE:
<221> NAME/KEY: VARIANT
<222> LOCATION: (1)..(43)
<223> OTHER INFORMATION: The GIP analogue contains one and only one
      residue Psi; wherein Psi is a residue independently selected from
      Lys, Arg, Orn and Cys and wherein the side chain of said residue
      is conjugated to a lipophilic substituent
<220> FEATURE:
<221> NAME/KEY: VARIANT
<222> LOCATION: (3)..(3)
<223> OTHER INFORMATION: Xaa is Aib, Ala, D-Ala, Gly, Ser, N-Me-Ser,
      Ac3c, Ac4c or Ac5c
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Lys, Psi or Ile; wherein Psi is a
      residue independently selected from Lys, Arg, Orn and Cys and
      wherein the side chain of said residue is conjugated to a
      lipophilic substituent
<220> FEATURE:
<221> NAME/KEY: VARIANT
```

-continued

```
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ser, Glu, Lys or Psi; wherein Psi is a
      residue independently selected from Lys, Arg, Orn and Cys and
      wherein the side chain of said residue is conjugated to a
      lipophilic substituent
<220> FEATURE:
<221> NAME/KEY: VARIANT
<222> LOCATION: (18)..(18)
<223> OTHER INFORMATION: Xaa is Ile, Lys, Gln, Arg or Psi; wherein Psi
      is a residue independently selected from Lys, Arg, Orn and Cys
      and wherein the side chain of said residue is conjugated to a
      lipophilic substituent
<220> FEATURE:
<221> NAME/KEY: VARIANT
<222> LOCATION: (19)..(19)
<223> OTHER INFORMATION: Xaa is His, Arg or Ala
<220> FEATURE:
<221> NAME/KEY: VARIANT
<222> LOCATION: (20)..(20)
<223> OTHER INFORMATION: Xaa is Gln, Lys, Ala or Glu
<220> FEATURE:
<221> NAME/KEY: VARIANT
<222> LOCATION: (21)..(21)
<223> OTHER INFORMATION: Xaa is Gln, Lys, Ala, His or Arg
<220> FEATURE:
<221> NAME/KEY: VARIANT
<222> LOCATION: (22)..(22)
<223> OTHER INFORMATION: Xaa is Ala, Leu, Asp or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (25)..(25)
<223> OTHER INFORMATION: Xaa is Asn or Glu
<220> FEATURE:
<221> NAME/KEY: VARIANT
<222> LOCATION: (26)..(26)
<223> OTHER INFORMATION: Xaa is Tyr or Trp
<220> FEATURE:
<221> NAME/KEY: VARIANT
<222> LOCATION: (28)..(28)
<223> OTHER INFORMATION: Xaa is Leu, Glu, Ser, Lys or Val
<220> FEATURE:
<221> NAME/KEY: VARIANT
<222> LOCATION: (29)..(29)
<223> OTHER INFORMATION: Xaa is Ala, Ser or Arg
<220> FEATURE:
<221> NAME/KEY: VARIANT
<222> LOCATION: (30)..(30)
<223> OTHER INFORMATION: Xaa is Aib, Gly, Ala, Gln, Thr, Ser or Lys or
      is absent
<220> FEATURE:
<221> NAME/KEY: VARIANT
<222> LOCATION: (31)..(42)
<223> OTHER INFORMATION: Xaa, starting at pos. 31, is: Lys Gly (pos.
      31-32); Gly Pro Ser Ser Gly Ala Pro Pro Pro Ser; Gly Pro Ser Ser
      Gly Ala Pro Pro Ser; Pro Ser Ser Gly Ala Pro Pro Pro Ser; Pro Ser
      Ser Gly Ala Pro Pro Ser; Gly Lys Lys Asn Asp Trp Lys His Asn Ile
      Thr Gln; or absent.
<220> FEATURE:
<221> NAME/KEY: VARIANT
<222> LOCATION: (31)..(43)
<223> OTHER INFORMATION: Xaa is Psi (as defined in 'VARIANT' for
      positions 13, 17 and 18) or absent; This applies to positions 31,
      33, 39, 40, 41 or 43, dependent upon which chain of amino acids
      starts at pos. 31 as noted in the 'VARIANT' for positions 31-42
      (listed above).

<400> SEQUENCE: 86

Xaa Tyr Xaa Glu Gly Thr Phe Ile Ser Asp Xaa Xaa Xaa Glu Leu Xaa
1               5                   10                  15
```

```
Xaa Xaa Xaa Xaa Xaa Xaa Phe Xaa Xaa Xaa Leu Xaa Xaa Xaa Xaa
                    20                  25                  30

Xaa Xaa Xaa Xaa Xaa Xaa Xaa Xaa Xaa Xaa Xaa
        35                  40

<210> SEQ ID NO 87
<211> LENGTH: 43
<212> TYPE: PRT
<213> ORGANISM: Artificial sequence
<220> FEATURE:
<223> OTHER INFORMATION: Synthetic GIP analogue of general Formula II
<220> FEATURE:
<221> NAME/KEY: VARIANT
<222> LOCATION: (1)..(1)
<223> OTHER INFORMATION: Xaa is H-, Ac or pGlu
<220> FEATURE:
<221> NAME/KEY: VARIANT
<222> LOCATION: (1)..(43)
<223> OTHER INFORMATION: The GIP analogue contains one and only one
      residue Psi; wherein Psi is a Lys residue wherein the side chain
      of said Lys residue is conjugated to a lipophilic substituent
<220> FEATURE:
<221> NAME/KEY: VARIANT
<222> LOCATION: (3)..(3)
<223> OTHER INFORMATION: Xaa is Aib, Ala, D-Ala, Gly
<220> FEATURE:
<221> NAME/KEY: VARIANT
<222> LOCATION: (13)..(13)
<223> OTHER INFORMATION: Xaa is Lys, Psi or Ile; wherein Psi is a Lys
      residue wherein the side chain of said Lys residue is conjugated
      to a lipophilic substituent
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ser, Glu, Lys or Psi; wherein Psi is a
      Lys residue wherein the side chain of said Lys residue is
      conjugated to a lipophilic substituent
<220> FEATURE:
<221> NAME/KEY: VARIANT
<222> LOCATION: (18)..(18)
<223> OTHER INFORMATION: Xaa is Ile, Lys, Gln, Arg or Psi; wherein Psi
      is a Lys residue wherein the side chain of said Lys residue is
      conjugated to a lipophilic substituent
<220> FEATURE:
<221> NAME/KEY: VARIANT
<222> LOCATION: (19)..(19)
<223> OTHER INFORMATION: Xaa is His, Arg or Ala
<220> FEATURE:
<221> NAME/KEY: VARIANT
<222> LOCATION: (20)..(20)
<223> OTHER INFORMATION: Xaa is Gln or Ala
<220> FEATURE:
<221> NAME/KEY: VARIANT
<222> LOCATION: (21)..(21)
<223> OTHER INFORMATION: Xaa is Gln, Lys, Ala, His or Arg
<220> FEATURE:
<221> NAME/KEY: VARIANT
<222> LOCATION: (22)..(22)
<223> OTHER INFORMATION: Xaa is Ala, Asp or Glu
<220> FEATURE:
<221> NAME/KEY: VARIANT
<222> LOCATION: (24)..(24)
<223> OTHER INFORMATION: Xaa is Ile or Val
<220> FEATURE:
<221> NAME/KEY: VARIANT
<222> LOCATION: (25)..(25)
<223> OTHER INFORMATION: Xaa is Asn or Glu
<220> FEATURE:
<221> NAME/KEY: VARIANT
<222> LOCATION: (26)..(26)
<223> OTHER INFORMATION: Xaa is Tyr or Trp
<220> FEATURE:
<221> NAME/KEY: VARIANT
```

```
<222> LOCATION: (28)..(28)
<223> OTHER INFORMATION: Xaa is Leu, Glu, Ser, Lys or Val
<220> FEATURE:
<221> NAME/KEY: VARIANT
<222> LOCATION: (29)..(29)
<223> OTHER INFORMATION: Xaa is Ala, Ser or Arg
<220> FEATURE:
<221> NAME/KEY: VARIANT
<222> LOCATION: (30)..(30)
<223> OTHER INFORMATION: Xaa is Aib, Gly, Ala, Gln, Thr, Ser or Lys or
      is absent
<220> FEATURE:
<221> NAME/KEY: VARIANT
<222> LOCATION: (31)..(42)
<223> OTHER INFORMATION: Xaa, starting at position 31, is: Lys Gly (pos.
      31-32); Gly Pro Ser Ser Gly Ala Pro Pro Pro; Gly Pro Ser Ser Gly
      Ala Pro Pro Ser; Pro Ser Ser Gly Ala Pro Pro Pro Ser; Pro Ser Ser
      Gly Ala Pro Pro Pro Ser; Gly Lys Lys Asn Asp Trp Lys His Asn Ile Thr
      Gln; or absent.
<220> FEATURE:
<221> NAME/KEY: VARIANT
<222> LOCATION: (31)..(43)
<223> OTHER INFORMATION: Xaa is Psi (as defined in 'VARIANT' for
      positions 13, 17 and 18) or absent; This applies to positions 31,
      33, 39, 40, or 43, dependent upon which chain of amino acids
      starts at pos. 31 as noted in the 'VARIANT' for positions 31-42
      (listed above).

<400> SEQUENCE: 87

Xaa Tyr Xaa Glu Gly Thr Phe Ile Ser Asp Tyr Ser Xaa Glu Leu Xaa
1               5                   10                  15

Xaa Xaa Xaa Xaa Xaa Xaa Phe Xaa Xaa Xaa Leu Xaa Xaa Xaa Xaa Xaa
            20                  25                  30

Xaa Xaa Xaa Xaa Xaa Xaa Xaa Xaa Xaa Xaa Xaa
        35                  40

<210> SEQ ID NO 88
<211> LENGTH: 43
<212> TYPE: PRT
<213> ORGANISM: Artificial sequence
<220> FEATURE:
<223> OTHER INFORMATION: Synthetic GIP analogue of general Formula III
<220> FEATURE:
<221> NAME/KEY: VARIANT
<222> LOCATION: (1)..(1)
<223> OTHER INFORMATION: Xaa is H-, Ac or pGlu
<220> FEATURE:
<221> NAME/KEY: VARIANT
<222> LOCATION: (1)..(43)
<223> OTHER INFORMATION: The GIP analogue contains one and only one
      residue Psi; wherein Psi is a residue independently selected from
      Lys, Arg, Orn and Cys and wherein the side chain of said residue
      is conjugated to a lipophilic substituent
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys or Psi; wherein Psi is a residue
      independently selected from Lys, Arg, Orn and Cys and wherein the
      side chain of said residue is conjugated to a lipophilic
      substituent
<220> FEATURE:
<221> NAME/KEY: VARIANT
<222> LOCATION: (18)..(18)
<223> OTHER INFORMATION: Xaa is Ile or Psi; wherein Psi is a residue
      independently selected from Lys, Arg, Orn and Cys and wherein the
      side chain of said residue is conjugated to a lipophilic
      substituent
```

```
<220> FEATURE:
<221> NAME/KEY: VARIANT
<222> LOCATION: (19)..(19)
<223> OTHER INFORMATION: Xaa is His or Ala
<220> FEATURE:
<221> NAME/KEY: VARIANT
<222> LOCATION: (20)..(20)
<223> OTHER INFORMATION: Xaa is Gln or Ala
<220> FEATURE:
<221> NAME/KEY: VARIANT
<222> LOCATION: (21)..(21)
<223> OTHER INFORMATION: Xaa is Gln, Lys or Arg
<220> FEATURE:
<221> NAME/KEY: VARIANT
<222> LOCATION: (22)..(22)
<223> OTHER INFORMATION: Xaa is Ala, Asp or Glu
<220> FEATURE:
<221> NAME/KEY: VARIANT
<222> LOCATION: (25)..(25)
<223> OTHER INFORMATION: Xaa is Asn or Glu
<220> FEATURE:
<221> NAME/KEY: VARIANT
<222> LOCATION: (26)..(26)
<223> OTHER INFORMATION: Xaa is Tyr or Trp
<220> FEATURE:
<221> NAME/KEY: VARIANT
<222> LOCATION: (30)..(30)
<223> OTHER INFORMATION: Xaa is Gln or is absent
<220> FEATURE:
<221> NAME/KEY: VARIANT
<222> LOCATION: (31)..(42)
<223> OTHER INFORMATION: Xaa, starting at pos. 31, is: Lys Gly (pos.
      31-32); Gly Pro Ser Ser Gly Ala Pro Pro Pro Ser; Gly Pro Ser Ser
      Gly Ala Pro Pro Ser; Pro Ser Ser Gly Ala Pro Pro Pro Ser; Pro Ser
      Ser Gly Ala Pro Pro Ser; Gly Lys Lys Asn Asp Trp Lys His Asn Ile
      Thr Gln; or absent.
<220> FEATURE:
<221> NAME/KEY: VARIANT
<222> LOCATION: (31)..(43)
<223> OTHER INFORMATION: Xaa is Psi (as defined in 'VARIANT' for
      positions 17 and 18) or absent; This applies to positions 31, 33,
      39, 40, 41 or 43, dependent upon which chain of amino acids starts
      at pos. 31 as noted in the 'VARIANT' for positions 31-42 (listed
      above).

<400> SEQUENCE: 88

Xaa Tyr Ala Glu Gly Thr Phe Ile Ser Asp Tyr Ser Ile Glu Leu Xaa
1               5                   10                  15

Xaa Xaa Xaa Xaa Xaa Xaa Phe Val Xaa Xaa Leu Leu Ala Xaa Xaa Xaa
            20                  25                  30

Xaa Xaa Xaa Xaa Xaa Xaa Xaa Xaa Xaa Xaa Xaa
            35                  40
```

The invention claimed is:

1. A method of treating a metabolic disorder in an individual in need thereof, comprising administering to said individual (i) a GIP analogue in combination with (ii) a GLP-1 agonist;

whrerein the GIP analog is represented by the general Formula I:

(SEQ ID NO: 42)

$R^1$-Tyr-X2-Glu-Gly-Thr-Phe-Ile-Ser-Asp-X10-

X11-X12-Glu-Leu-X15-X16-X17-X18-X19-X20-X21-

Phe-X23-X24-X25-Leu-X27-X28-X29-Y1-Y2-$R^2$ (I)

wherein $R^1$ is H-, Ac or pGlu;

X2 is Aib, Ala, D-Ala, Gly, Ser, N-Me-Ser, Ac3c, Ac4c or Ac5c;

X10 is Tyr, Leu or Ser;

X11 is Ser or Leu;

X12 is Lys, ψ or Ile;

X15 is Asp or Glu;

X16 is Ser, Glu, Lys or ψ;

X17 is Ile, Lys, Gln, Arg or ψ;

X18 is His, Arg or Ala;

X19 is Gln, Lys, Ala or Glu;

X20 is Gln, Lys, Ala, His or Arg;

X21 is Ala, Leu, Asp or Glu;

X23 is Val or Ile;

X24 is Asn or Glu;

X25 is Tyr or Trp;

X27 is Leu, Glu, Ser, Lys or Val;

X28 is Ala, Ser or Arg;
X29 is Aib, Gly, Ala, Gln, Thr, Ser or Lys or is absent;
Y1 is Lys-Gly, Gly-Pro-Ser-Ser-Gly-Ala-Pro-Pro-Pro-Ser (SEQ ID NO: 43), Gly-Pro-Ser-Ser-Gly-Ala-Pro-Pro-Ser (SEQ ID NO: 44), Pro-Ser-Ser-Gly-Ala-Pro-Pro-Pro-Ser (SEQ ID NO: 45), Pro-Ser-Ser-Gly-Ala-Pro-Pro-Ser (SEQ ID NO: 46), Gly-Lys-Lys-Asn-Asp-Trp-Lys-His-Asn-Ile-Thr-Gln (SEQ ID NO: 47) or absent;
Y2 is ψ or is absent;
R² is —NH₂ or —OH;
wherein ψ is a residue independently selected from Lys, Arg, Orn and Cys and wherein the side chain of said residue is conjugated to a lipophilic substituent;
and wherein the GIP analogue contains one and only one residue ψ;
or a pharmaceutically acceptable salt thereof.

2. A method according to claim 1 wherein the metabolic disorder is diabetes or a diabetes related disorder, obesity, or an obesity related disorder.

3. A method according to claim 2 wherein the diabetes related disorder is selected from the group consisting of insulin resistance, glucose intolerance, increased fasting glucose, hypoglycemia, pre-diabetes, type 1 diabetes, type 2 diabetes, gestational diabetes hypertension, dyslipidemia, atherosclerosis, arteriosclerosis, coronary heart disease, peripheral artery disease, stroke; or is a condition associated with atherogenic dyslipidemia, a blood fat disorder, elevated blood pressure, hypertension, a prothrombotic state, a proinflammatory state, hypoglycemia induced by insulin treatment, and combinations thereof.

4. A method according to claim 2 wherein the diabetes related disorder is osteoporosis including increased risk of bone fractures.

5. A method according to claim 3 wherein the blood fat disorder is high triglycerides, low HDL cholesterol, high LDL cholesterol, plaque buildup in artery walls; wherein the prothrombotic state comprises high fibrinogen levels in the blood or high plasminogen activator inhibitor-1 levels in the blood; or wherein the proinflammatory state comprises an elevated C-reactive protein level in the blood.

6. A method according to claim 2 wherein the obesity related disorder is selected from the group consisting of obesity linked inflammation, obesity linked gallbladder disease or obesity induced sleep apnea, atherogenic dyslipidemia, blood fat disorders, elevated blood pressure, hypertension, a prothrombotic state, and a proinflammatory state, and combinations thereof.

7. A method of treating osteoporosis in a subject in need thereof, comprising administering to the subject an effective amount of a GIP analogue, wherein the GIP analogue is represented by the general Formula I:

(SEQ ID NO: 42)
R¹-Tyr-X2-Glu-Gly-Thr-Phe-Ile-Ser-Asp-X10-X11-X12-

Glu-Leu-X15-X16-X17-X18-X19-X20-X21-Phe-X23-X24-

X25-Leu-X27-X28-X29-Y1-Y2-R² (I)

wherein
R¹ is H—, Ac or pGlu;
X2 is Aib, Ala, D-Ala, Gly, Ser, N-Me-Ser, Ac3c, Ac4c or Ac5c;
X10 is Tyr, Leu or Ser;
X11 is Ser or Leu;
X12 is Lys, ψ or Ile;
X15 is Asp or Glu;
X16 is Ser, Glu, Lys or ψ;
X17 is Ile, Lys, Gln, Arg or ψ;
X18 is His, Arg or Ala;
X19 is Gln, Lys, Ala or Glu;
X20 is Gln, Lys, Ala, His or Arg;
X21 is Ala, Leu, Asp or Glu;
X23 is Val or Ile;
X24 is Asn or Glu;
X25 is Tyr or Trp;
X27 is Leu, Glu, Ser, Lys or Val;
X28 is Ala, Ser or Arg;
X29 is Aib, Gly, Ala, Gln, Thr, Ser or Lys or is absent;
Y1 is Lys-Gly, Gly-Pro-Ser-Ser-Gly-Ala-Pro-Pro-Pro-Ser (SEQ ID NO: 43), Gly-Pro-Ser-Ser-Gly-Ala-Pro-Pro-Ser (SEQ ID NO: 44), Pro-Ser-Ser-Gly-Ala-Pro-Pro-Pro-Ser (SEQ ID NO: 45), Pro-Ser-Ser-Gly-Ala-Pro-Pro-Ser (SEQ ID NO: 46), Gly-Lys-Lys-Asn-Asp-Trp-Lys-His-Asn-Ile-Thr-Gln (SEQ ID NO: 47) or absent;
Y2 is ψ or is absent;
R² is —NH₂ or —OH;
wherein ψ is a residue independently selected from Lys, Arg, Orn and Cys and wherein the side chain of said residue is conjugated to a lipophilic substituent;
and wherein the GIP analogue contains one and only one residue ψ;
or a pharmaceutically acceptable salt thereof.

8. A method according to claim 1, wherein the GIP analogue is represented by the general Formula III:

(SEQ ID NO: 50)
R¹-Tyr-Aib-Glu-Gly-Thr-Phe-Ile-Ser-Asp-

Tyr-Ser-Ile-Glu-Leu-X15-X16-X17-X18-X19-

X20-X21-Phe-Val-X24-X25-Leu-Leu-Ala-X29-

Y1-Y2-R²
(III)

wherein
R¹ is H-, Ac or pGlu;
X15 is Asp or Glu;
X16 is Lys or ψ;
X17 is Ile or ψ;
X18 is His or Ala X19 is Gln or Ala;
X20 is Gln, Lys or Arg;
X21 is Ala, Asp or Glu;
X24 is Asn or Glu;
X25 is Tyr or Trp
X29 is Gln or is absent;
Y1 is Lys-Gly, Gly-Pro-Ser-Ser-Gly-Ala-Pro-Pro-Pro-Ser (SEQ ID NO: 43), Gly-Pro-Ser-Ser-Gly-Ala-Pro-Pro-Ser (SEQ ID NO: 44), Pro-Ser-Ser-Gly-Ala-Pro-Pro-Pro-Ser (SEQ ID NO: 45), Pro-Ser-Ser-Gly-Ala-Pro-Pro-Ser (SEQ ID NO: 46), Gly-Lys-Lys-Asn-Asp-Trp-Lys-His-Asn-Ile-Thr-Gln (SEQ ID NO: 47) or absent;
Y2 is ψ or is absent;
R² is —NH₂ or —OH;
wherein ψ is a residue independently selected from Lys, Arg, Orn and Cys and wherein the side chain of said residue is conjugated to a lipophilic substituent;
and wherein the GIP analogue contains one and only one residue ψ;
or a pharmaceutically acceptable salt thereof.

9. A method according to claim 8, wherein the GIP analogue comprises one of the following residues or combinations of residues:

Asp15, Lys20;
Asp15, Arg20;
Asp15, Arg20, Glu24;
Asp15, Lys16;
Asp15, Lys16, Glu24;
Asp15, ψ16, Ala21;
Ala21, Glu24;
Asp15, Arg20, Gln29;
Asp15, Arg20, Gly29;
Asp15, Ile17, Arg20, Gly29;
Asp15, Ile17, Lys20, Gly29;
Asp15, Ala28;
Asp15, Ile17, Lys20, Ala28;
Asp15, Ile23, Glu24;
Asp15, ψ17, Lys20;
Asp15, ψ17, Arg20;
Asp15, ψ17, Arg20;
Asp15, ψ17, Arg20, Glu24;
Asp15, Lys 16, ψ17;
Asp15, Lys 16, ψ17, Glu24;
Asp15, ψ17, Ala21;
Ala21, ψ17, Glu24;
Asp15, Asp15, ψ17, Arg20, Gln29;
Asp15, ψ17, Arg20, Gly29;
Asp15, ψ17, Arg20, Gly29;
Asp15, Ile17, Lys20, Gly29;
Asp15; ψ17;
Asp15, ψ17, Ala28;
Asp15, Ile17, Lys20, Ala28;
Asp15, ψ17, Ile23, Glu24.

10. A method according to claim 8, wherein ψ of the GIP analogue is a residue of Lys, Arg, Orn or Cys in which the side chain is conjugated to a substituent having the formula —$Z^1$ or —$Z^2$—$Z^1$.

11. A method according to claim 10, wherein —$Z^1$ of the GIP analogue is a fatty chain having at a terminus a connection —X— to ψ or to $Z^2$;
wherein —X— is a bond, —CO—, —SO—, or —$SO_2$—; and, optionally, $Z^1$ has a polar group at the end of the chain distal from connection —X—; said polar group comprising a carboxylic acid or a carboxylic acid bioisostere, a phosphonic acid, or a sulfonic acid group.

12. A method according to claim 11, wherein $Z^1$ of the GIP analogue is a group of formula:
A—B—Alk—X— wherein
A is hydrogen or a carboxylic acid, a carboxylic acid bioisostere, a phosphonic acid, or a sulfonic acid group;
B is a bond or a linker;
X is a bond, acyl (—CO—), sulfinyl (—SO—), or sulfonyl (—$SO_2$—); and
Alk is a fatty chain that may be optionally substituted with one or more substituents.

13. A method according to claim 12, wherein $Z^1$ of the GIP analogue is:
A—B—$C_{16-20}$alkylene—(CO)— wherein A is H or —COOH and B is a bond.

14. A method according to claim 10, wherein $Z^2$ of the GIP analogue is a spacer bound at one terminus by Y, which is a nitrogen, oxygen or sulfur atom, and at the other terminus by X, which is a bond or an acyl (—CO—), sulfinyl (—SO—), sulfonyl (—$SO_2$—) or absent.

15. A method according to claim 10, wherein —$Z^1$-$Z^2$ of the GIP analogue is:

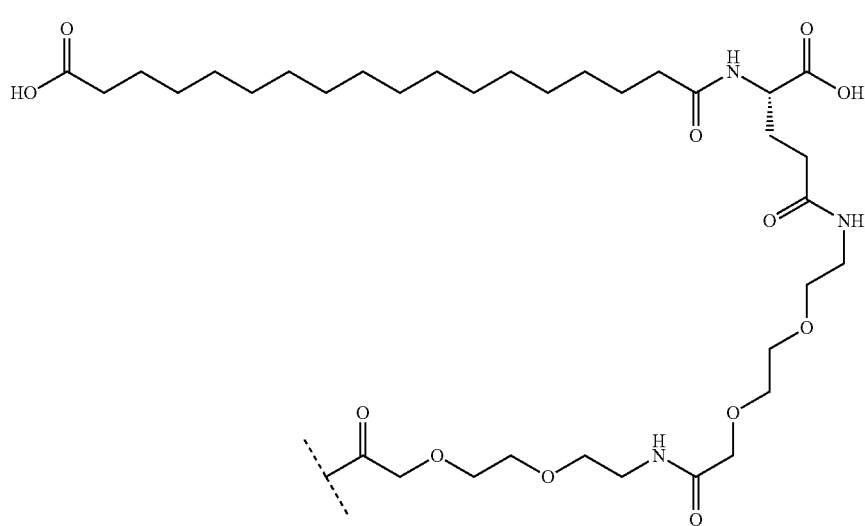

(i)

[17-carboxy-heptadecanoyl]-isoGlu-Peg3-Peg3

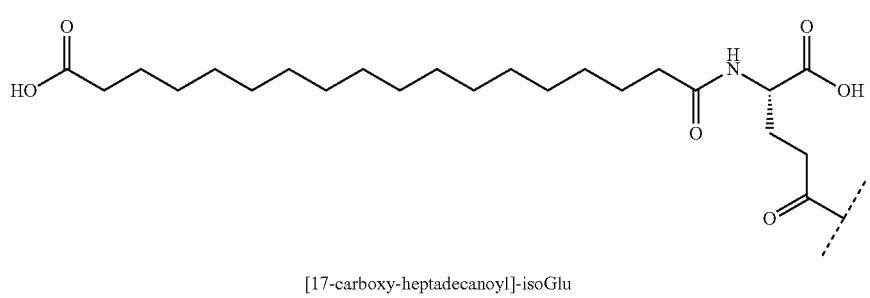

(ii)

[17-carboxy-heptadecanoyl]-isoGlu

-continued
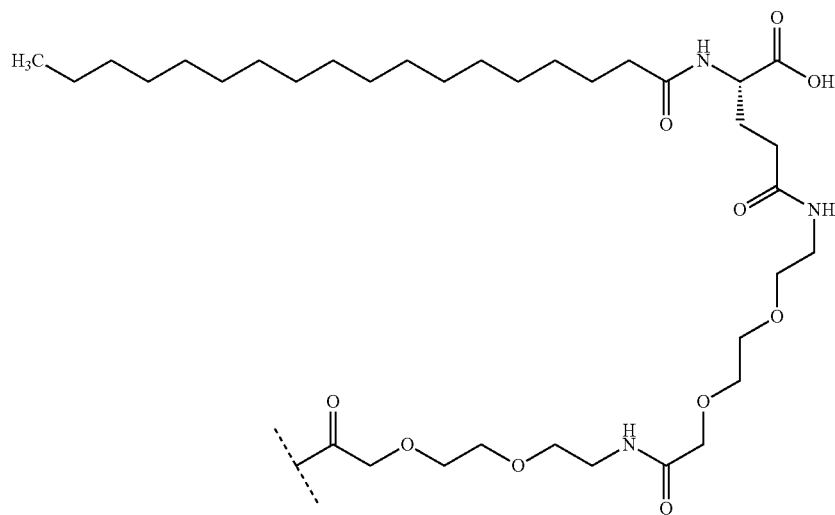
Octadecanoyl-isoGlu-Peg3-Peg3 (iii)
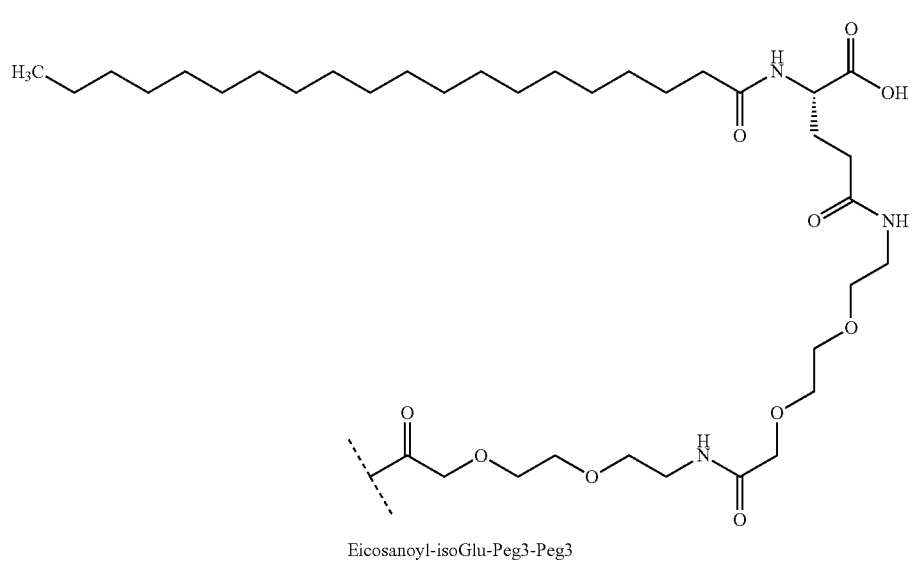
Eicosanoyl-isoGlu-Peg3-Peg3 (iv)
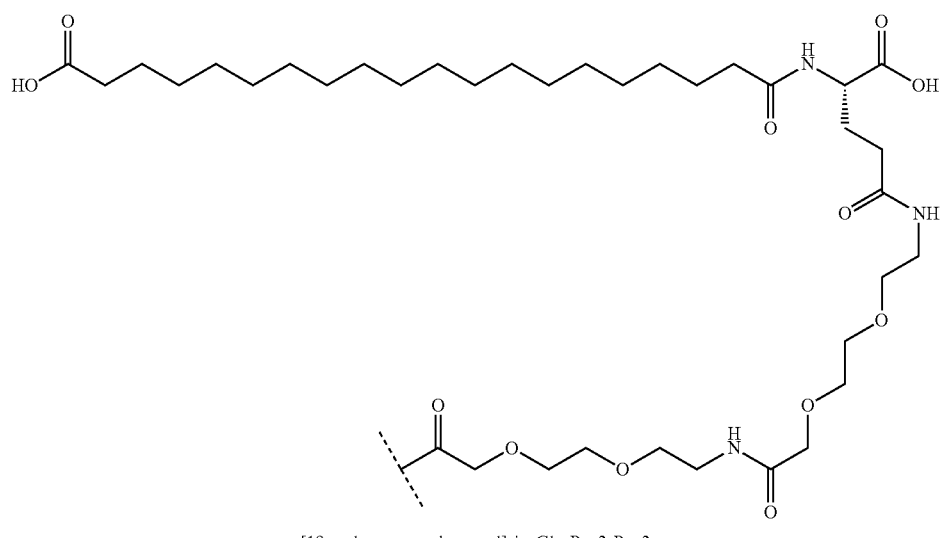
[19-carboxy-nonadecanoyl]-isoGlu-Peg3-Peg3 (v)

(vi)

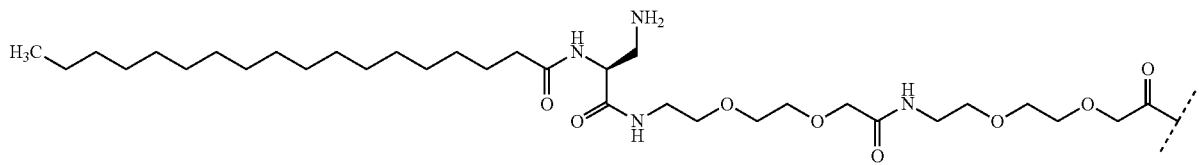

Octadecanoyl-Dapa-Peg3-Peg3

(vii)

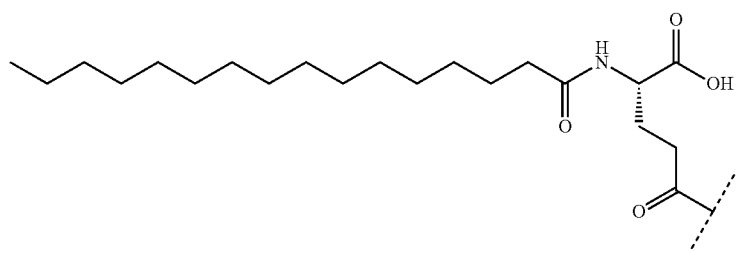

Hexadecanoyl-isoGlu (viii)

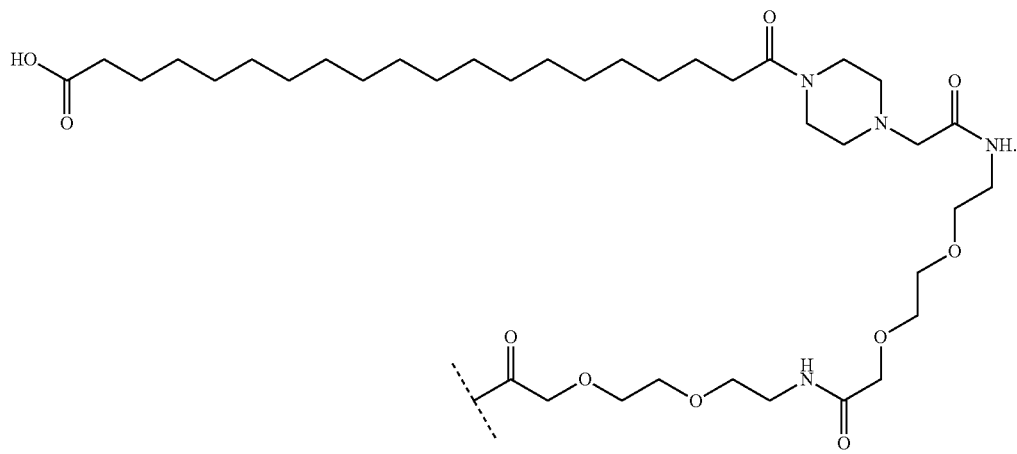

(19-Carboxy-nonadecanoyl)-[(Piperazine-1-yl)-acetyl]-Peg3-Peg3

16. A method according to claim 8, wherein the GIP analogue has the sequence:

```
                                              (SEQ ID NO: 51)
Y-Aib-EGTFISDYSIELDKΨHQQDFVNWLLAQGPSSGAPPPS;

(SEQ ID NO: 52)
Y-Aib-EGTFISDYSIELDΨIHQQDFVNWLLAQGPSSGAPPPS;

(SEQ ID NO: 53)
Y-Aib-EGTFISDYSIELEKΨHQQDFVNWLLAQGPSSGAPPPS;

(SEQ ID NO: 54)
Y-Aib-EGTFISDYSIELDKIHQQDFVNWLLAQGPSSGAPPPSΨ;

(SEQ ID NO: 55)
Y-Aib-EGTFISDYSIELDKIHQQDFVNWLLAQΨ;

(SEQ ID NO: 56)
Y-Aib-EGTFISDYSIELDKIHQQDFVNWLLAQKGΨ;

(SEQ ID NO:57)
Y-Aib-EGTFISDYSIELDKΨHQQDFVNYLLAQGPSSGAPPPS;

(SEQ ID NO: 58)
Y-Aib-EGTFISDYSIELDKΨHQQDFVNWLLAQGPSSGAPPPS;

(SEQ ID NO: 59)
Y-Aib-EGTFISDYSIELDKΨAAQDFVNWLLAQGPSSGAPPPS;

(SEQ ID NO: 60)
Y-Aib-EGTFISDYSIELEKΨAAKEFVNWLLAQGPSSGAPPPS;

(SEQ ID NO: 61)
Y-Aib-EGTFISDYSIELEKΨAQRAFVEWLLAQGPSSGAPPPS;

(SEQ ID NO: 62)
Y-Aib-EGTFISDYSIELEKIAQRAFVEWLLAQGPSSGAPPPSΨ;

(SEQ ID NO: 63)
Y-Aib-EGTFISDYSIELEKIAQRAFVEWLLAQΨ;

(SEQ ID NO: 64)
Y-Aib-EGTFISDYSIELDKΨAAQDFVNWLLAGPSSGAPPPS;

(SEQ ID NO: 65)
Y-Aib-EGTFISDYSIELDKIAAQDFVNWLLAGPSSGAPPPSΨ;

(SEQ ID NO: 66)
Y-Aib-EGTFISDYSIELDKKΨAQRAFVEWLLAQGPSSGAPPPS;

(SEQ ID NO: 67)
Y-Aib-EGTFISDYSIELDKKΨAQRAFIEWLLAQGPSSGAPPPS;
```

```
                                          (SEQ ID NO: 68)
Y-Aib-EGTFISDYSIELDKIAQRAFIEWLLAGPSSGAPPPSKΨ;

(SEQ ID NO: 69)
Y-Aib-EGTFISDYSIELDKIAQKEFIEWLLAGPSSGAPPPSKΨ;

(SEQ ID NO: 70)
Y-Aib-EGTFISDYSIELDKIAAQDFIEWLLAGPSSGAPPPSKΨ;

(SEQ ID NO: 71)
Y-Aib-EGTFISDYSIELDKIAAQDFVEWLLAGPSSGAPPPSKΨ;

(SEQ ID NO: 72)
Y-Aib-EGTFISDYSIELDKIAQRAFIEWLLAQGPSSGAPPPSKΨ;

(SEQ ID NO: 73)
Y-Aib-EGTFISDYSIELDKKΨAAQAFVNWLLAGPSSGAPPPS;

(SEQ ID NO: 74)
Y-Aib-EGTFISDYSIELDKKΨAAQDFVNWLLAAGPSSGAPPPS;

(SEQ ID NO: 75)
Y-Aib-EGTFISDYSIELDKKΨAAQDFINWLLAGPSSGAPPPS;

(SEQ ID NO: 76)
Y-Aib-EGTFISDYSIELDKKΨAAQDFIEWLLAGPSSGAPPPS;

(SEQ ID NO: 77)
Y-Aib-EGTFISDYSIELDKKΨAAQDFIEWLLAGPSSGAPPPS;

(SEQ ID NO: 78)
Y-Aib-EGTFISDYSIELDKΨIAQRAFIEWLLAQGPSSGAPPPS;

(SEQ ID NO: 79)
Y-Aib-EGTFISDYSKΨELDKIAQRAFIEWLLAQGPSSGAPPPS;

(SEQ ID NO: 80)
Y-DAla-EGTFISDYSIELDKKΨAQRAFIEWLLAQGPSSGAPPPS;

(SEQ ID NO: 81)
Y-DAla-EGTFISDYSIELDKIAAQDFIEWLLAGPSSGAPPPSKΨ;

(SEQ ID NO: 82)
Y-Aib-EGTFISDYSIELDKKΨAAQDFIEWLLAQGPSSGAPPPS;

(SEQ ID NO: 83)
Y-Aib-EGTFISDYSIELDKKΨAAQDFINWLLAQGPSSGAPPPS;
or (SEQ ID NO: 84)
Y-Aib-EGTFISDYSIELDKKΨAAQAFIEWLLAQGPSSGAPPPS.
```

17. A method according to claim 8, wherein the GIP analogue has the sequence:

```
                                          (SEQ ID NO: 1)
Y-Aib-EGTFISDYSIELDK-K(Hexadecanoyl-isoGlu)-
HQQDFVNWLLAQGPSSGAPPPS;

(SEQ ID NO: 2)
Y-Aib-EGTFISDYSIELD-K(Hexadecanoyl-isoGlu)-I
HQQDFVNWLLAQGPSSGAPPPS;

(SEQ ID NO: 3)
Y-Aib-EGTFISDYSIELEK-K(Hexadecanoyl-isoGlu)-
HQQDFVNWLLAQGPSSGAPPPS;

(SEQ ID NO: 4)
Y-Aib-EGTFISDYSIELDKIHQQDFVNWLLAQGPSSGAPPPS-
K([19-carboxy-nonadecanoyl]-isoGlu-
Peg3-Peg3);

(SEQ ID NO: 5)
Y-Aib-EGTFISDYSIELDKIHQQDFVNWLLAQGPSSGAPPPS-
K(Hexadecanoyl-isoGlu);

(SEQ ID NO: 6)
Y-Aib-EGTFISDYSIELDKIHQQDFVNWLLAQ-
K(Hexadecanoyl-isoGlu);

(SEQ ID NO: 7)
Y-Aib-EGTFISDYSIELDKIHQQDFVNWLLAQKG-K
(Hexadecanoyl-isoGlu);

(SEQ ID NO: 8)
Y-Aib-EGTFISDYSIELDK-K([19-carboxy-
nonadecanoyl]-isoGlu-Peg3-Peg3)-
HQQDFVNYLLAQGPSSGAPPPS;

(SEQ ID NO: 9)
Y-Aib-EGTFISDYSIELDK-K([19-carboxy-
nonadecanoyl]-isoGlu-Peg3-Peg3)-
HQQDFVNWLLAQGPSSGAPPPS;

(SEQ ID NO: 10)
Y-Aib-EGTFISDYSIELDK-K([19-carboxy-
nonadecanoyl]-isoGlu-Peg3-Peg3)-
AAQDFVNWLLAQGPSSGAPPPS;

(SEQ ID NO: 11)
Y-Aib-EGTFISDYSIELEK-K([19-carboxy-
nonadecanoyl]-isoGlu-Peg3-Peg3)-
AAKEFVNWLLAQGPSSGAPPPS;

(SEQ ID NO: 12)
Y-Aib-EGTFISDYSIELEK-K([19-carboxy-
nonadecanoyl]-isoGlu-Peg3-Peg3)-
AQRAFVEWLLAQGPSSGAPPPS;

(SEQ ID NO: 13)
Y-Aib-EGTFISDYSIELEKIAQRAFVEWLLAQ
GPSSGAPPPS-K([19-carboxy-
nonadecanoyl]-isoGlu-Peg3-Peg3);

(SEQ ID NO: 14)
[[H-]]Y-Aib-EGTFISDYSIELEKIAQRAFV
EWLLAQ-K([19-carboxy-nonadecanoyl]-
isoGlu-Peg3-Peg3);

(SEQ ID NO: 15)
[[H-]]Y-Aib-EGTFISDYSIELDK-K([19-
carboxy-nonadecanoyl]-isoGlu-Peg3-Peg3)-
AAQDFVNWLLAGPSSGAPPPS;

(SEQ ID NO: 16)
[[H-]]Y-Aib-EGTFISDYSIELDKIAAQDFVNWLL
AGPSSGAPPPS-K([19-carboxy-nonadecanoyl]-
isoGlu-Peg3-Peg3);
```

(SEQ ID NO: 17)
Y-Aib-EGTFISDYSIELDK-K([19-Carboxy-nonadecanoyl]-isoGlu-Peg3-Peg3)-AQRAFVEWLLAQGPSSGAPPPS;

(SEQ ID NO: 18)
Y-Aib-EGTFISDYSIELDK-K([19-Carboxy-nonadecanoyl]-isoGlu-Peg3-Peg3)-AQRAFIEWLLAQGPSSGAPPPS;

(SEQ ID NO: 19)
Y-Aib-EGTFISDYSIELDK-K((19-Carboxy-nonadecanoyl)-[(Piperazine-1-yl)-acetyl]-Peg3-Peg3)-AQRAFIEWLLAQGPSSGAPPPS;

(SEQ ID NO: 20)
Y-Aib-EGTFISDYSIELDK-K((19-Carboxy-nonadecanoyl)-[(Piperazine-1-yl)-acetyl]-Peg3-Peg3)-AQRAFVEWLLAQGPSSGAPPPS;

(SEQ ID NO: 21)
Y-Aib-EGTFISDYSIELDK-K((19-Carboxy-nonadecanoyl)-[(Piperazine-1-yl)-acetyl]-Peg3-Peg3)-AQKEFVEWLLAAGPSSGAPPPS (SEQ ID NO: 22)
Y-Aib-EGTFISDYSIELDK-K([19-Carboxy-nonadecanoyl]-isoGlu-Peg3-Peg3)-AQKEFVEWLLAAGPSSGAPPPS;

(SEQ ID NO: 23)
Y-Aib-EGTFISDYSIELDKIAQRAFIEWLLAGPSSGAPPPS-K([19-Carboxy-nonadecanoyl]-isoGlu-Peg3-Peg3);

(SEQ ID NO: 24)
Y-Aib-EGTFISDYSIELDKIAQKEFIEWLLAGPSSGAPPPS-K([19-Carboxy-nonadecanoyl]-isoGlu-Peg3-Peg3);

(SEQ ID NO: 25)
Y-Aib-EGTFISDYSIELDKIAAQDFIEWLLAGPSSGAPPPS-K([19-Carboxy-nonadecanoyl]-isoGlu-Peg3-Peg3);

(SEQ ID NO: 26)
Y-Aib-EGTFISDYSIELDKIAAQDFIEWLLAGPSSGAPPPS-K((19-Carboxy-nonadecanoyl)-[(Piperazine-1-yl)-acetyl]-Peg3-Peg3);

(SEQ ID NO: 27)
Y-Aib-EGTFISDYSIELDKIAAQDFVEWLLAGPSSGAPPPS-K([19-Carboxy-nonadecanoyl]-isoGlu-Peg3-Peg3);

(SEQ ID NO: 28)
Y-Aib-EGTFISDYSIELDKIAQRAFIEWLLAQGPSSGAPPPS-K([19-Carboxy-nonadecanoyl]-isoGlu-Peg3-Peg3);

(SEQ ID NO: 29)
Y-Aib-EGTFISDYSIELDK-K([19-Carboxy-nonadecanoyl]-isoGlu-Peg3-Peg3)-AAQAFVNWLLAGPSSGAPPPS;

(SEQ ID NO: 30)
Y-Aib-EGTFISDYSIELDK-K([19-Carboxy-nonadecanoyl]-isoGlu-Peg3-Peg3)-AAQDFVNWLLAAGPSSGAPPPS;

(SEQ ID NO: 31)
Y-Aib-EGTFISDYSIELDK-K([19-Carboxy-nonadecanoyl]-isoGlu-Peg3-Peg3)-AAQDFINWLLAGPSSGAPPPS;

(SEQ ID NO: 32)
Y-Aib-EGTFISDYSIELDK-K([19-Carboxy-nonadecanoyl]-isoGlu-Peg3-Peg3)-AAQDFIEWLLAGPSSGAPPPS;

(SEQ ID NO: 33)
Y-Aib-EGTFISDYSIELDK-K((19-Carboxy-nonadecanoyl)-[(Piperazine-1-yl)-acetyl]-Peg3-Peg3)-AAQDFIEWLLAGPSSGAPPPS;

(SEQ ID NO: 34)
Y-Aib-EGTFISDYSIELD-K([19-Carboxy-nonadecanoyl]-isoGlu-Peg3-Peg3)-IAQRAFIEWLLAQGPSSGAPPPS;

(SEQ ID NO: 35)
Y-Aib-EGTFISDYS-K([19-Carboxy-nonadecanoyl]-isoGlu-Peg3-Peg3)-ELDKIAQRAFIEWLLAQGPSSGAPPPS;

(SEQ ID NO: 36)
Y-DAla-EGTFISDYSIELDK-K([19-Carboxy-nonadecanoyl]-isoGlu-Peg3-Peg3)-AQRAFIEWLLAQGPSSGAPPPS;

(SEQ ID NO: 37)
Y-DAla-EGTFISDYSIELDKIAAQDFIEWLLAGPSSGAPPPS-K((19-Carboxy-nonadecanoyl)-[(Piperazine-1-yl)-acetyl]-Peg3-Peg3);

-continued (SEQ ID NO: 38)
Y-Aib-EGTFISDYSIELDK-K([19-Carboxy-nonadecanoyl]-isoGlu-Peg3-Peg3)-AAQDFIEWLLAQGPSSGAPPPS;

(SEQ ID NO: 39)
Y-Aib-EGTFISDYSIELDK-K([19-Carboxy-nonadecanoyl]-isoGlu-Peg3-Peg3)-AAQDFINWLLAQGPSSGAPPPS;

(SEQ ID NO: 40)
Y-Aib-EGTFISDYSIELDK-K([19-Carboxy-nonadecanoyl]-isoGlu-Peg3-Peg3)-AAQAFIEWLLAQGPSSGAPPPS;
or (SEQ ID NO: 41)
Y-Aib-EGTFISDYSIELDK-K((19-Carboxy-nonadecanoyl)-[(Piperazine-1-yl)-acetyl]-Peg3-Peg3)-AAQAFIEWLLAQGPSSGAPPPS.

18. A method according to claim 8, wherein the GIP analogue has the sequence:

(SEQ ID NO: 1)
H-Y-Aib-EGTFISDYSIELDK-K(Hexadecanoyl-isoGlu)-HQQDFVNWLLAQGPSSGAPPPS-NH$_2$ (SEQ ID NO: 2)
H-Y-Aib-EGTFISDYSIELD-K(Hexadecanoyl-isoGlu)-IHQQDFVNWLLAQGPSSGAPPPS-NH$_2$;

(SEQ ID NO: 3)
H-Y-Aib-EGTFISDYSIELEK-K(Hexadecanoyl-isoGlu)-HQQDFVNWLLAQGPSSGAPPPS-NH$_2$;

(SEQ ID NO: 4)
H-Y-Aib-EGTFISDYSIELDKIHQQDFVNWLLAQGPSSGAPPPS-K([19-carboxy-nonadecanoyl]-isoGlu-Peg3-Peg3)-NH$_2$;

(SEQ ID NO: 5)
H-Y-Aib-EGTFISDYSIELDKIHQQDFVNWLLAQGPSSGAPPPS-K(Hexadecanoyl-isoGlu)-NH$_2$;

(SEQ ID NO: 6)
H-Y-Aib-EGTFISDYSIELDKIHQQDFVNWLI_AQ-K(Hexadecanoyl-isoGlu)-NH$_2$;

(SEQ ID NO: 7)
H-Y-Aib-EGTFISDYSIELDKIHQQDFVNWLLAQKG-K(Hexadecanoyl-isoGlu)-NH$_2$;

(SEQ ID NO: 8)
H-Y-Aib-EGTFISDYSIELDK-K([19-carboxy-nonadecanoyl]-isoGlu-Peg3-Peg3)-HQQDFVNYLLAQGPSSGAPPPS-NH$_2$;

(SEQ ID NO: 9)
H-Y-Aib-EGTFISDYSIELDK-K([19-carboxy-nonadecanoyl]-isoGlu-Peg3-Peg3)-HQQDFVNWLLAQGPSSGAPPPS-NH$_2$ ;

(SEQ ID NO: 10)
H-Y-Aib-EGTFISDYSIELDK-K([19-carboxy-nonadecanoyl]-isoGlu-Peg3-Peg3)-AAQDFVNWLLAQGPSSGAPPPS-NH$_2$;

(SEQ ID NO: 11)
H-Y-Aib-EGTFISDYSIELEK-K([19-carboxy-nonadecanoyl]-isoGlu-Peg3-Peg3)-AAKEFVNWLLAQGPSSGAPPPS-NH$_2$;

(SEQ ID NO: 12)
H-Y-Aib-EGTFISDYSIELEK-K([19-carboxy-nonadecanoyl]-isoGlu-Peg3-Peg3)-AQRAFVEWLLAQGPSSGAPPPS-NH$_2$;

(SEQ ID NO: 13)
H-Y-Aib-EGTFISDYSIELEKIAQRAFVEWLLAQGPSSGAPPPS-K([19-carboxy-nonadecanoyl]-isoGlu-Peg3-Peg3)-NH$_2$;

(SEQ ID NO: 14)
H-Y-Aib-EGTFISDYSIELEKIAQRAFVEWLLAQ-K([19-carboxy-nonadecanoyl]-isoGlu-Peg3-Peg3)-NH$_2$;

(SEQ ID NO: 15)
H-Y-Aib-EGTFISDYSIELDK-K([19-carboxy-nonadecanoyl]-isoGlu-Peg3-Peg3)-AAQDFVNWLLAGPSSGAPPPS-NH$_2$;

(SEQ ID NO: 16)
H-Y-Aib-EGTFISDYSIELDKIAAQDFVNWLLAGPSSGAPPPS-K([19-carboxy-nonadecanoyl]-isoGlu-Peg3-Peg3)-NH$_2$;

(SEQ ID NO: 17)
H-Y-Aib-EGTFISDYSIELDK-K([19-Carboxy-nonadecanoyl]-isoGlu-Peg3-Peg3)-AQRAFVEWLLAQGPSSGAPPPS-NH$_2$;

(SEQ ID NO: 18)
H-Y-Aib-EGTFISDYSIELDK-K([19-Carboxy-nonadecanoyl]-isoGlu-Peg3-Peg3)-AQRAFIEWLLAQGPSSGAPPPS-NH$_2$;

(SEQ ID NO: 19)
H-Y-Aib-EGTFISDYSIELDK-K((19-Carboxy-nonadecanoyl)-[(Piperazine-1-yl)-acetyl]-Peg3-Peg3)-AQRAFIEWLLAQGPSSGAPPPS-NH$_2$;

(SEQ ID NO: 20)
H-Y-Aib-EGTFISDYSIELDK-K((19-Carboxy-nonadecanoyl)-[(Piperazine-1-yl)-acetyl]-Peg3-Peg3)-AQRAFVEWLLAQGPSSGAPPPS-NH$_2$;

(SEQ ID NO: 21)
H-Y-Aib-EGTFISDYSIELDK-K((19-Carboxy-nonadecanoyl)-[(Piperazine-1-yl)-acetyl]-Peg3-Peg3)-AQKEFVEWLLAAGPSSGAPPPS-NH$_2$;

(SEQ ID NO: 22)
H-Y-Aib-EGTFISDYSIELDK-K([19-Carboxy-nonadecanoyl]-isoGlu-Peg3-Peg3)-AQKEFVEWLLAAGPSSGAPPPS-NH$_2$;

(SEQ ID NO: 23)
H-Y-Aib-EGTFISDYSIELDKIAQRAFIEWLLAGPSSGAPPPS-K([19-Carboxy-nonadecanoyl]-isoGlu-Peg3-Peg3)-NH$_2$;

(SEQ ID NO: 24)
H-Y-Aib-EGTFISDYSIELDKIAQKEFIEWLLAGPSSGAPPPS-K([19-Carboxy-nonadecanoyl]-isoGlu-Peg3-Peg3)-NH$_2$;

(SEQ ID NO: 25)
H-Y-Aib-EGTFISDYSIELDKIAAQDFIEWLLAGPSSGAPPPS-K([19-Carboxy-nonadecanoyl]-isoGlu-Peg3-Peg3)-NH$_2$;

(SEQ ID NO: 26)
H-Y-Aib-EGTFISDYSIELDKIAAQDFIEWLLAGPSSGAPPPS-K((19-Carboxy-nonadecanoyl)-r(PiDerazine-1-yl)-acetyl]-Peg3-Peg3)-NH$_2$;

(SEQ ID NO: 27)
H-Y-Aib-EGTFISDYSIELDKIAAQDFVEWLLAGPSSGAPPPS-K([19-Carboxy-nonadecanoyl]-isoGlu-Peg3-Peg3)-NH$_2$;

(SEQ ID NO: 28)
H-Y-Aib-EGTFISDYSIELDKIAQRAFIEWLLAQGPSSGAPPPS-K([19-Carboxy-nonadecanoyl]-isoGlu-Peg3-Peg3)-NH$_2$;

(SEQ ID NO: 29)
H-Y-Aib-EGTFISDYSIELDK-K([19-Carboxy-nonadecanoyl]-isoGlu-Peg3-Peg3)-AAQAFVNWLLAGPSSGAPPPS-NH$_2$;

(SEQ ID NO: 30)
H-Y-Aib-EGTFISDYSIELDK-K([19-Carboxy-nonadecanoyl]-isoGlu-Peg3-Peg3)-AAQDFVNWLLAAGPSSGAPPPS-NH$_2$;

(SEQ ID NO: 31)
H-Y-Aib-EGTFISDYSIELDK-K([19-Carboxy-nonadecanoyl]-isoGlu-Peg3-Peg3)-AAQDFINWLLAGPSSGAPPPS-NH$_2$;

(SEQ ID NO: 32)
H-Y-Aib-EGTFISDYSIELDK-K([19-Carboxy-nonadecanoyl]-isoGlu-Peg3-Peg3)-AAQDFIEWLLAGPSSGAPPPS-NH$_2$;

(SEQ ID NO: 33)
H-Y-Aib-EGTFISDYSIELDK-K((19-Carboxy-nonadecanoyl)-[(Piperazine-1-yl)-acetyl]-Peg3-Peg3)-AAQDFIEWLLAGPSSGAPPPS-NH$_2$;

(SEQ ID NO: 34)
H-Y-Aib-EGTFISDYSIELD-K([19-Carboxy-nonadecanoyl]-isoGlu-Peg3-Peg3)-IAQRAFIEWLLAQGPSSGAPPPS-NH$_2$;

(SEQ ID NO: 35)
H-Y-Aib-EGTFISDYS-K([19-Carboxy-nonadecanoyl]-isoGlu-Peg3-Peg3)-ELDKIAQRAFIEWLLAQGPSSGAPPPS-NH$_2$;

(SEQ ID NO: 36)
H-Y-DAla-EGTFISDYSIELDK-K([19-Carboxy-nonadecanoyl]-isoGlu-Peg3-Peg3)-AQRAFIEWLLAQGPSSGAPPPS-NH$_2$;

(SEQ ID NO: 37)
H-Y-DAla-EGTFISDYSIELDKIAAQDFIEWLLAGPSSGAPPPS-K((19-Carboxy-nonadecanoyl)-[(PiDerazine-1-yl)-acetyl]-Peg3-Peg3)-NH$_2$;

(SEQ ID NO: 38)
H-Y-Aib-EGTFISDYSIELDK-K([19-Carboxy-nonadecanoyl]-isoGlu-Peg3-Peg3)-AAQDFIEWLLAQGPSSGAPPPS-NH$_2$;

(SEQ ID NO: 39)
H-Y-Aib-EGTFISDYSIELDK-K([19-Carboxy-nonadecanoyl]-isoGlu-Peg3-Peg3)-AAQDFINWLLAQGPSSGAPPPS-NH$_2$;

(SEQ ID NO: 40)
H-Y-Aib-EGTFISDYSIELDK-K([19-Carboxy-nonadecanoyl]-isoGlu-Peg3-Peg3)-AAQAFIEWLLAQGPSSGAPPPS-NH$_2$;
Or -continued (SEQ ID NO: 41)
H-Y-Aib-EGTFISDYSIELDK-K((19-Carboxy-nonadecanoyl)-[(Piperazine-1-yl)-acetyl]-Peg3-Peg3)-AAQAFIEWLLAQG PSSGAPPPS-NH$_2$.

19. A GIP analogue according to claim 1, comprising one of the following residues or combinations of residues:
Aib2, Asp15, Lys20;
Aib2, Asp15, Arg20;
Aib2, Asp15, Arg20, Ile23;
Aib2, Ile12, Asp15, Arg20, Ile23, Glu24;
Ile12, Asp15, Ile23;
Ile12, Asp15, Ile23 Glu24;
Ile12, Asp15, Ala21, Ile23;
Aib2, Ala21, Ile23, Glu24;
Aib2, Asp15, Ile23;
Aib2, Asp15, Arg20, 11e23, Gln29;
Aib2, Asp15, Arg20, Gly29;
Aib2, Asp15, Ile17, Arg20, Gly29;
Aib2, Asp15, Ile17, Lys20, Gly29;
DAla2, Asp15, Ile23;
DAla2, Asp15, Ile23, Ala28;
Aib2, Asp15, Ile17, Lys20, Ala28;
Asp15, Ile23, Glu24;
N-Me-Ser2, Asp15, Lys20;
N-Me-Ser2, Asp15, Arg20;
N-Me-Ser2, Asp15, Arg20, Ile23;
N-Me-Ser2, Ile12, Asp15, Arg20, Ile23, Glu24;
N-Me-Ser2, Ala21, Ile23, Glu24;
N-Me-Ser2, Asp15, Ile23;
N-Me-Ser2, Asp15, Arg20, 11e23, Gln29;
N-Me-Ser2, Asp15, Arg20, Gly29;
N-Me-Ser2, Asp15, Ile17, Arg20, Gly29;
N-Me-Ser2, Asp15, Ile17, Lys20, Gly29;
N-Me-Ser2, Asp15, Ile23;
N-Me-Ser2, Asp15, Ile23, Ala28;
Ac3c2, Asp15, Lys20;
Ac3c2, Asp15, Arg20;
Ac3c2, Asp15, Arg20, Ile23;
Ac3c2, Ile12, Asp15, Arg20, Ile23, Glu24;
Ac3c2, Ala21, Ile23, Glu24;
Ac3c2, Asp15, Ile23;
Ac3c2, Asp15, Arg20, Ile23, Gln29;
Ac3c2, Asp15, Arg20, Gly29;
Ac3c2, Asp15, 11e17, Arg20, Gly29;
Ac3c2, Asp15, 11e17, Lys20, Gly29;
Ac3c2, Asp15, Ile23;
Ac3c2, Asp15, Ile23, Ala28;
Ac4c2, Asp15, Lys20;
Ac4c2, Asp15, Arg20;
Ac4c2, Asp15, Arg20, Ile23;
Ac4c2, Ile12, Asp15, Arg20, Ile23, Glu24;
Ac4c2, Ala21, Ile23, Glu24;
Ac4c2, Asp15, 11e23;
Ac4c2, Asp15, Arg20, Ile23, Gln29;
Ac4c2, Asp15, Arg20, Gly29;
Ac4c2, Asp15, Ile17, Arg20, Gly29;
Ac4c2, Asp15, Ile17, Lys20, Gly29;
Ac4c2, Asp15, Ile23;
Ac4c2, Asp15, Ile23, Ala28;
Ac5c2, Asp15, Lys20;
Ac5c2, Asp15, Arg20;
Ac5c2, Asp15, Arg20, Ile23;
Ac5c2, Ile12, Asp15, Arg20, Ile23, Glu24;
Ac5c2, Ala21, Ile23, Glu24;
Ac5c2, Asp15, Ile23;
Ac5c2, Asp15, Arg20, Ile23, Gln29;
Ac5c2, Asp15, Arg20, Gly29;
Ac5c2, Asp15, Ile17, Arg20, Gly29;
Ac5c2, Asp15, Ile17, Lys20, Gly29;
Ac5c2, Asp15, Ile23; and
Ac5c2, Asp15, Ile23, Ala28.

20. A method according to claim 2, wherein the diabetes related disorder is hypoglycemia induced by insulin treatment.

21. A method according to claim 13, wherein $Z1$ of the GIP analogue is:
A—B—C$_{16-20}$alkylene—(CO)— wherein B is a bond, selected from:
17-carboxy-heptadecanoyl HOOC—(CH$_2$)$_{16}$—(CO)—;
19-carboxy-nonadecanoyl HOOC—(CH$_2$)$_{18}$—(CO)—;
Octadecanoyl H3C—(CH$_2$)$_{16}$—(CO)—; or Eicosanoyl H$_3$C—(CH$_2$)$_{18}$—(CO)—.

* * * * *